(12) United States Patent
Morein et al.

(10) Patent No.: US 9,907,846 B2
(45) Date of Patent: Mar. 6, 2018

(54) **NANOPARTICLES, COMPOSED OF STEROL AND SAPONIN FROM *QUILLAJA SAPONARIA MOLINA* FOR USE IN PHARMACEUTICAL COMPOSITIONS**

(71) Applicant: Moreinx AB, Enkoping (SE)

(72) Inventors: Bror Morein, Uppsala (SE); Saideh Berenjian, Uppsala (SE); Kefei Hu, Uppsala (SE)

(73) Assignee: MX ADJUVAC AB, Enkoping (SE)

( * ) Notice: Subject to any disclaimer, the term of this patent is extended or adjusted under 35 U.S.C. 154(b) by 0 days.

(21) Appl. No.: 14/781,761

(22) PCT Filed: Mar. 31, 2014

(86) PCT No.: PCT/SE2014/050380
§ 371 (c)(1),
(2) Date: Oct. 1, 2015

(87) PCT Pub. No.: WO2014/163558
PCT Pub. Date: Oct. 9, 2014

(65) Prior Publication Data
US 2016/0045595 A1    Feb. 18, 2016

(30) Foreign Application Priority Data
Apr. 1, 2013    (SE) .................................... 1350405

(51) Int. Cl.
| | | |
|---|---|---|
| *A61K 31/704* | (2006.01) | |
| *A61K 9/51* | (2006.01) | |
| *A61K 9/107* | (2006.01) | |
| *A61K 39/39* | (2006.01) | |
| *A61K 47/28* | (2006.01) | |
| *A61K 31/575* | (2006.01) | |
| *A61K 39/145* | (2006.01) | |

(Continued)

(52) U.S. Cl.
CPC ............ *A61K 39/39* (2013.01); *A61K 9/1075* (2013.01); *A61K 9/5123* (2013.01);
(Continued)

(58) Field of Classification Search
CPC ... A61K 31/704; A61K 9/5123; A61K 9/1075
See application file for complete search history.

(56) References Cited

U.S. PATENT DOCUMENTS 5,679,354 A    10/1997 Morein et al.

FOREIGN PATENT DOCUMENTS

| | | |
|---|---|---|
| CA | 2064911 A1 | 8/1990 |
| WO | 2013051994 | 4/2013 |

OTHER PUBLICATIONS

Bankefors, "Methods for Structural Characterisation of Quillaja Saponins by Electrospray Ionisation Ion Trap Multiple-Stage Mass Spectrometry," Doctoral Thesis, Swedish University of Agricultural Sciences, Uppsala, 2008.

(Continued)

*Primary Examiner* — Carlos Azpuru
(74) *Attorney, Agent, or Firm* — Andrus Intellectual Property Law, LLP

(57) ABSTRACT

A nanoparticle comprising at least one sterol, e.g. cholesterol and a component from *Quillaja Saponaria* Molina (QuilQ) selected from *quillaja* saponin, characterized in that said nanoparticles do not comprise a phospholipid and in that the sterol molecule is bound by a hydrophobic bond between a hydroxyl group of the sterol and terpene moieties in a Quil A micelle and by an hydrophilic ester bond between a sterol OH$^-$ and COOH$^-$ or aldehyde groups in the QuilA micelle. It also relates to a composition comprising the nanoparticles, and the use thereof as adjuvant, especially in vaccines, as carriers for amphipathic or hydrophobic molecules and as agents for treatment of cancer. Further, it regards a method for producing the phospholipid-free nanoparticles, a method for the treatment of cancer and a method for assessing the applicability of the cancer treating method.

25 Claims, 27 Drawing Sheets

(51) Int. Cl.
*G01N 33/50* (2006.01)
*A61K 9/00* (2006.01)

(52) U.S. Cl.
CPC .......... *A61K 31/575* (2013.01); *A61K 31/704* (2013.01); *A61K 39/145* (2013.01); *A61K 47/28* (2013.01); *G01N 33/5011* (2013.01); *A61K 9/0019* (2013.01); *G01N 2800/52* (2013.01)

(56) References Cited

OTHER PUBLICATIONS

Copland et al., "Hydration of lipid films with an aqueous solution of Quil A: a simple method for the preparation of immune-stimulating complexes", International Journal of Pharmaceutics, 2000, 196:135-139.
Mitra et al., "Cholesterol Solubilization in Aqueous Micellar Solutions of Quillaja Saponin, Bile Salts, or Nonionic Surfactants", J. Agric. Food Chem., 2001, 49:384-394.
International Search Report for PCT/SE2014/050380 dated Jul. 17, 2014.
Written Opinion for PCT/SE2014/050380 dated Jul. 24, 2014.
Kersten, et al., "On the structure of immune-stimulating saponin-lipid complexes (iscoms)", Biochimica et Biophysica Aca, 1062 (1991) 165-171.
Hu,Kefei, "Comparison of G3 and saponin-cholesterol ISCOM Matrix formulated with the dialysis method described by Kersten and ISCONOVA", Moreinx, Plan/ Onvaq International AB, pp. 1-14.

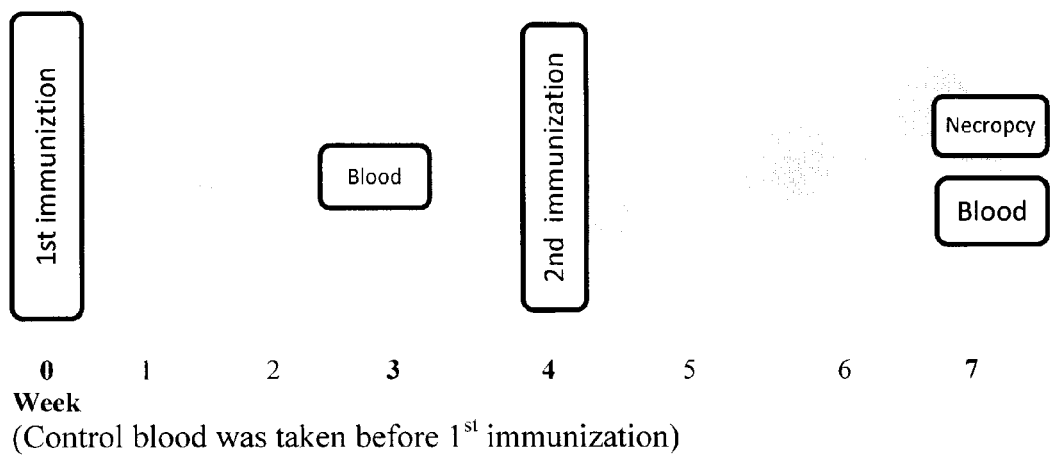
(Control blood was taken before 1st immunization)
Figure 13A1
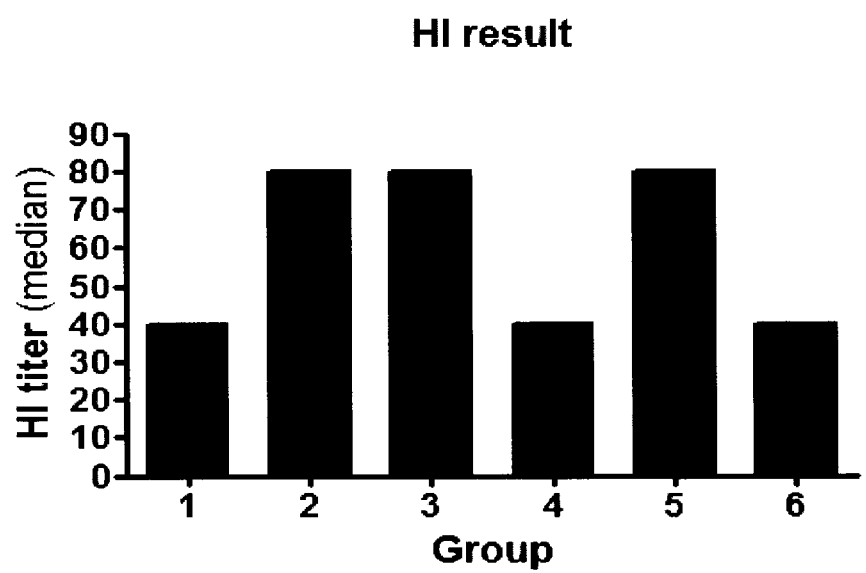
Figure 13A2

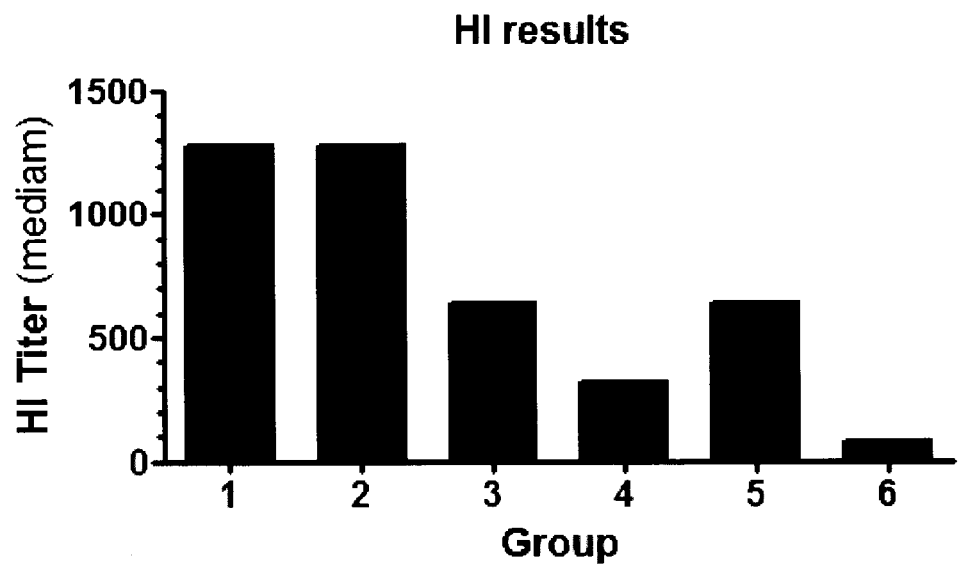
Figure 13A3
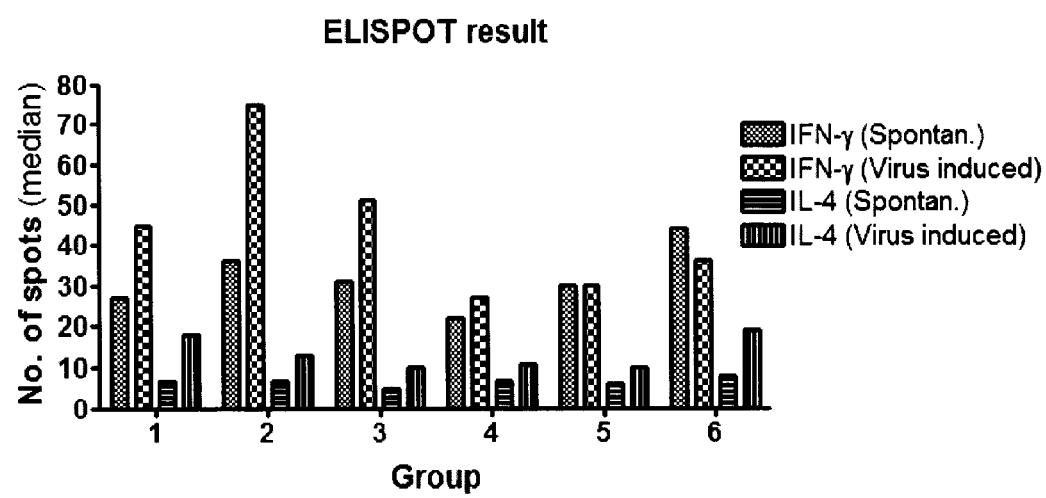
Figure 13A4

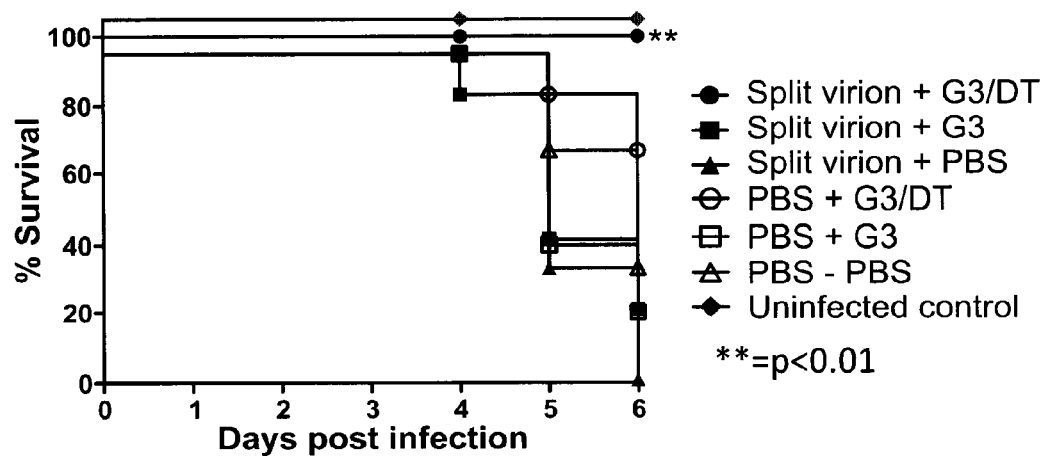
Figure 13B1

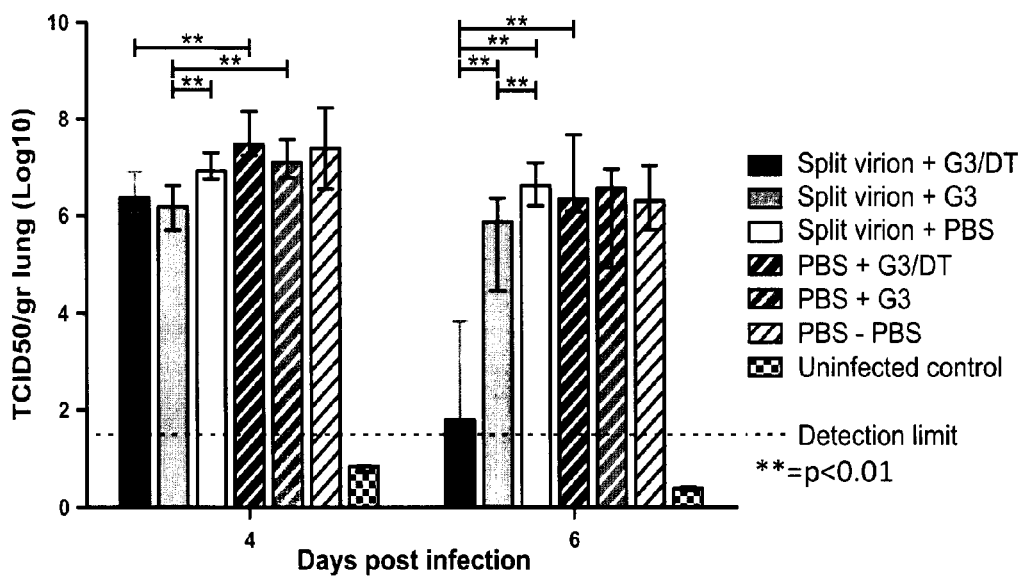
Figure 13B2

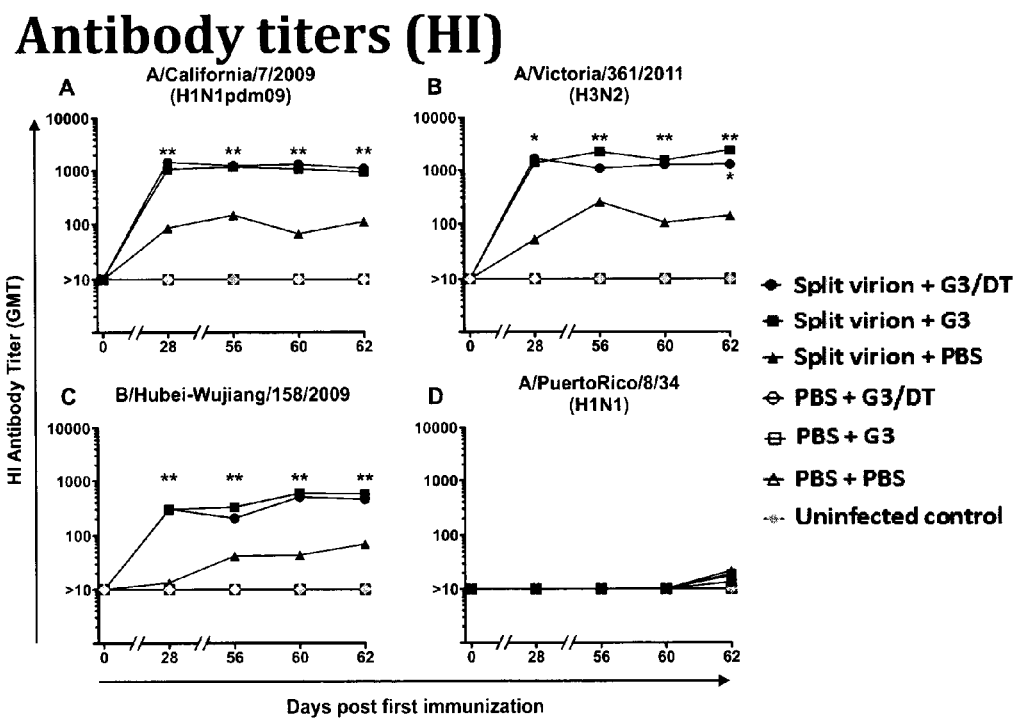
Figure 13B3

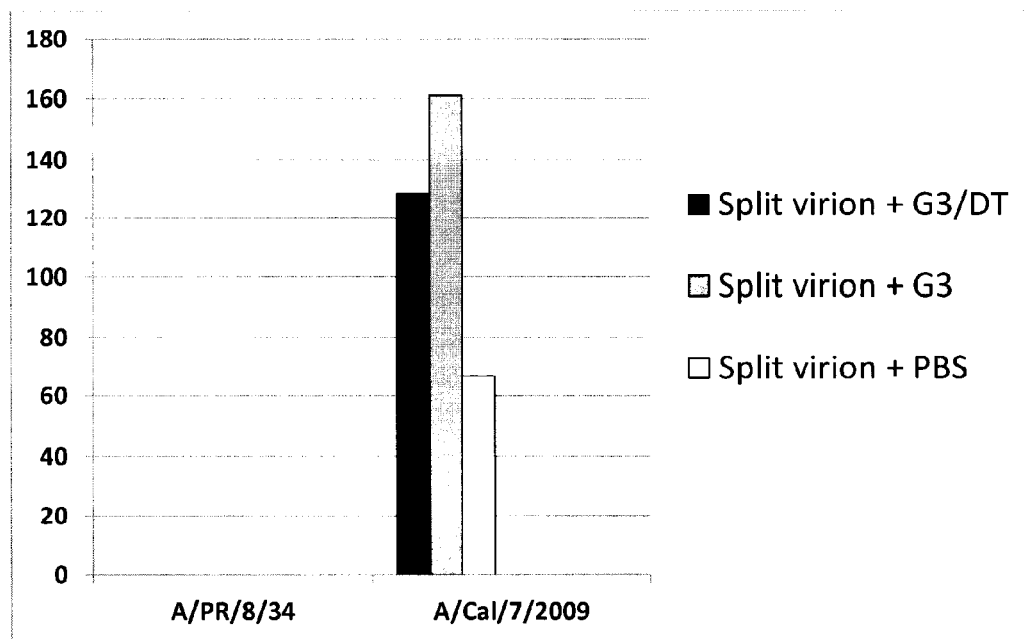
No cross neutralization of challenge strain A/PR/8/34
Figure 13B4

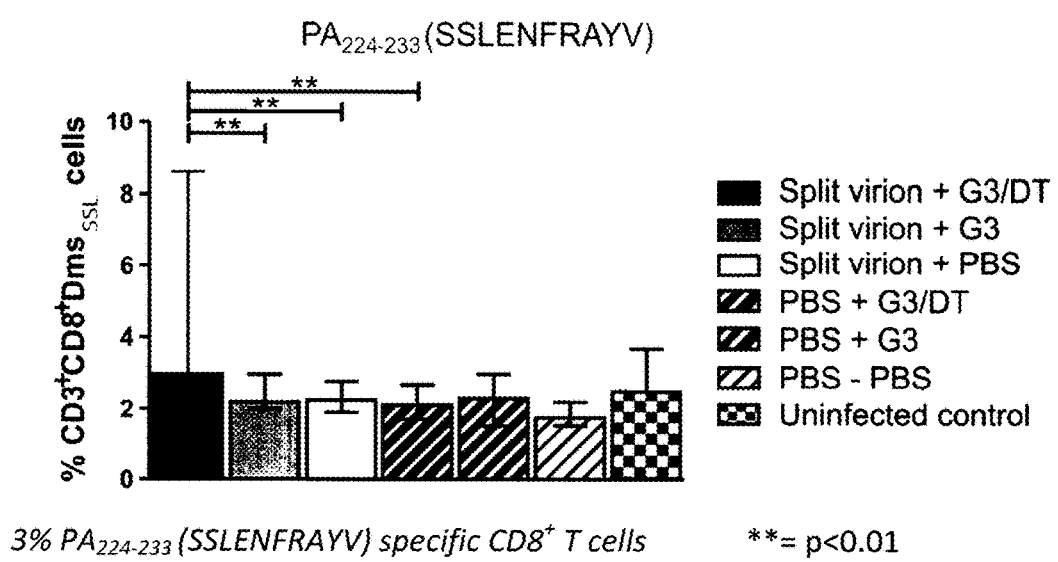
Figure 13B5

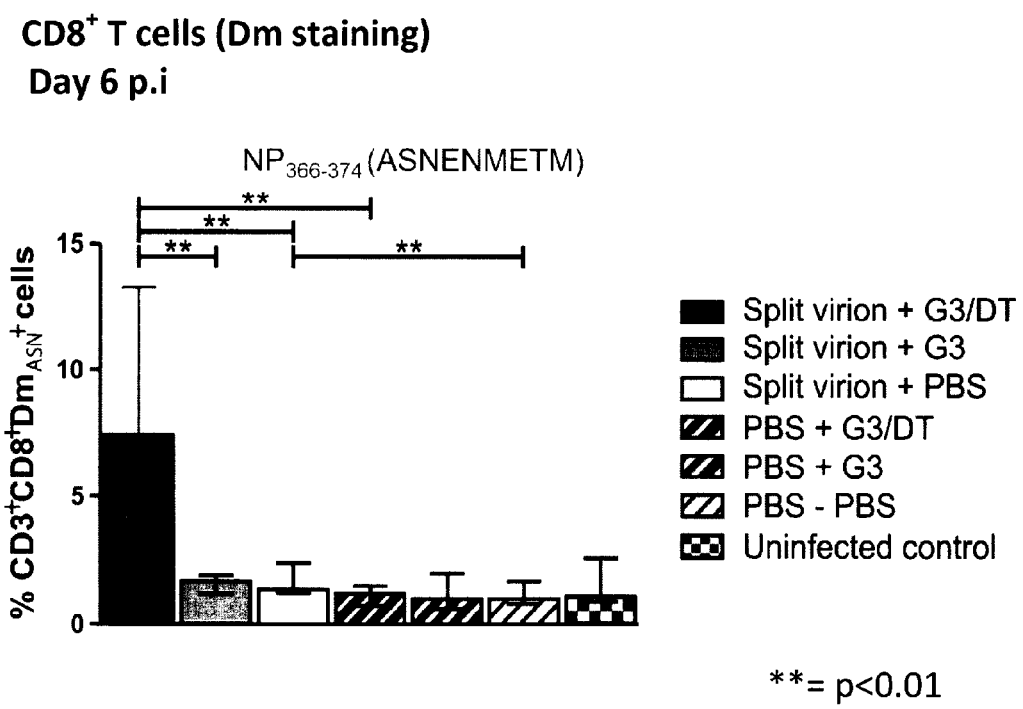
Figure 13B6

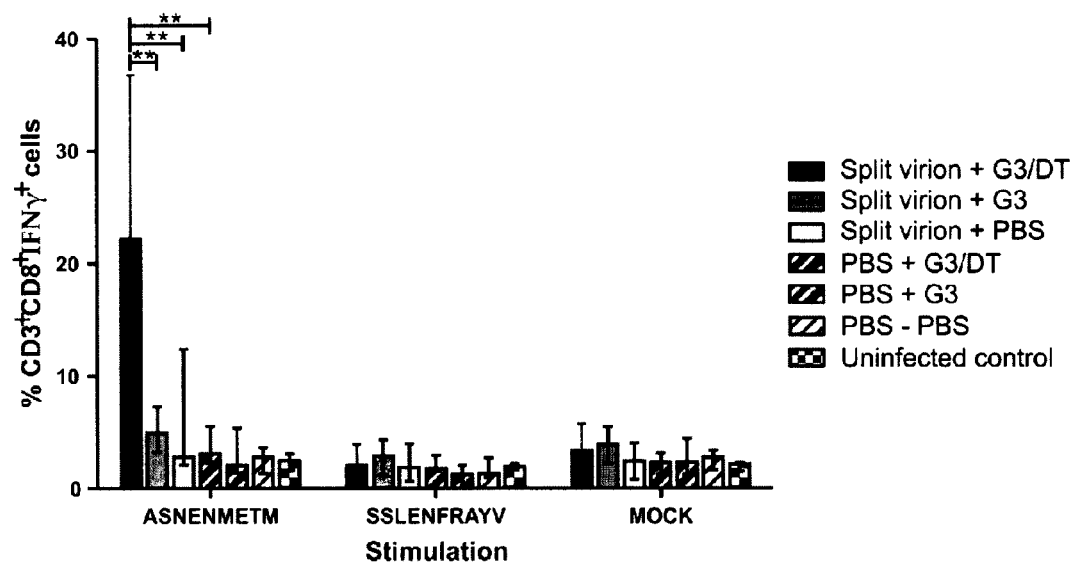
Figure 13B7

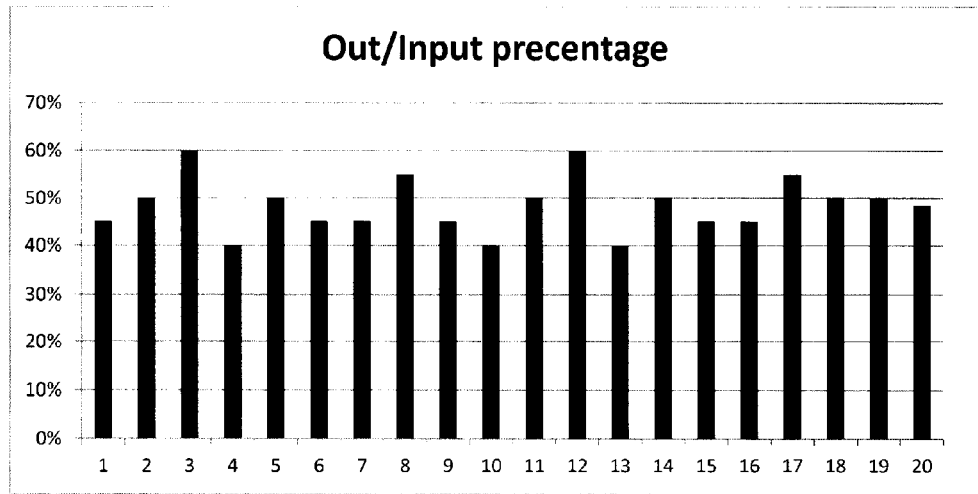
Figure 18:1
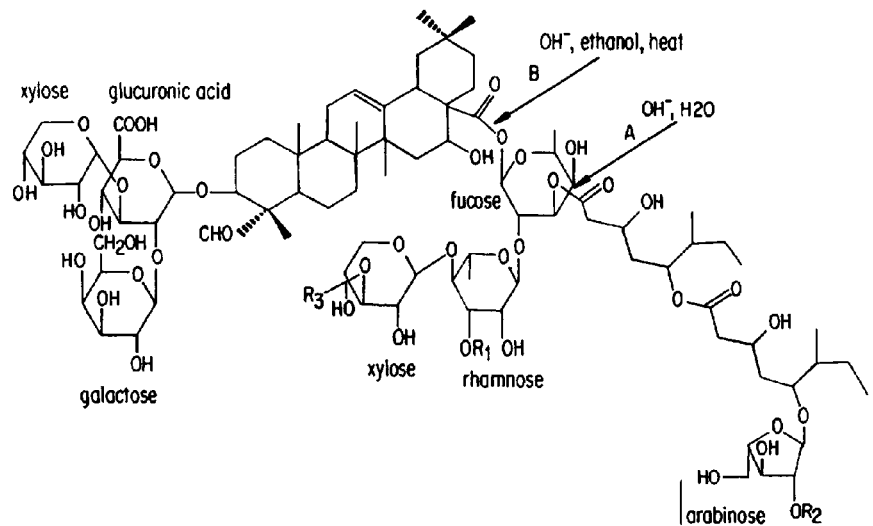
Figure 18:2A

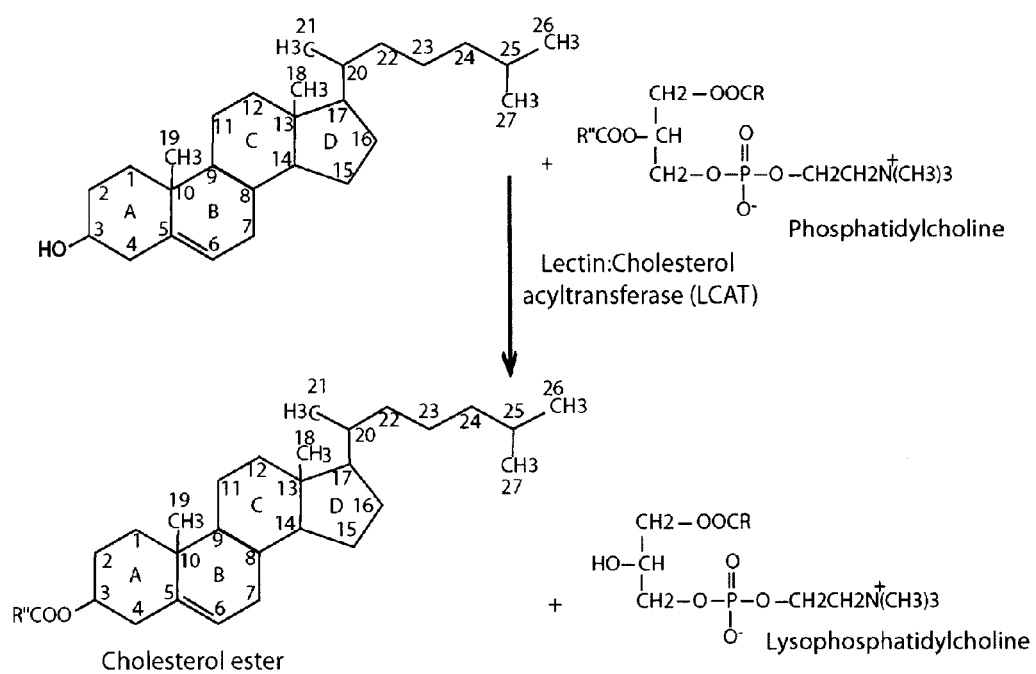
Figure 18:2B

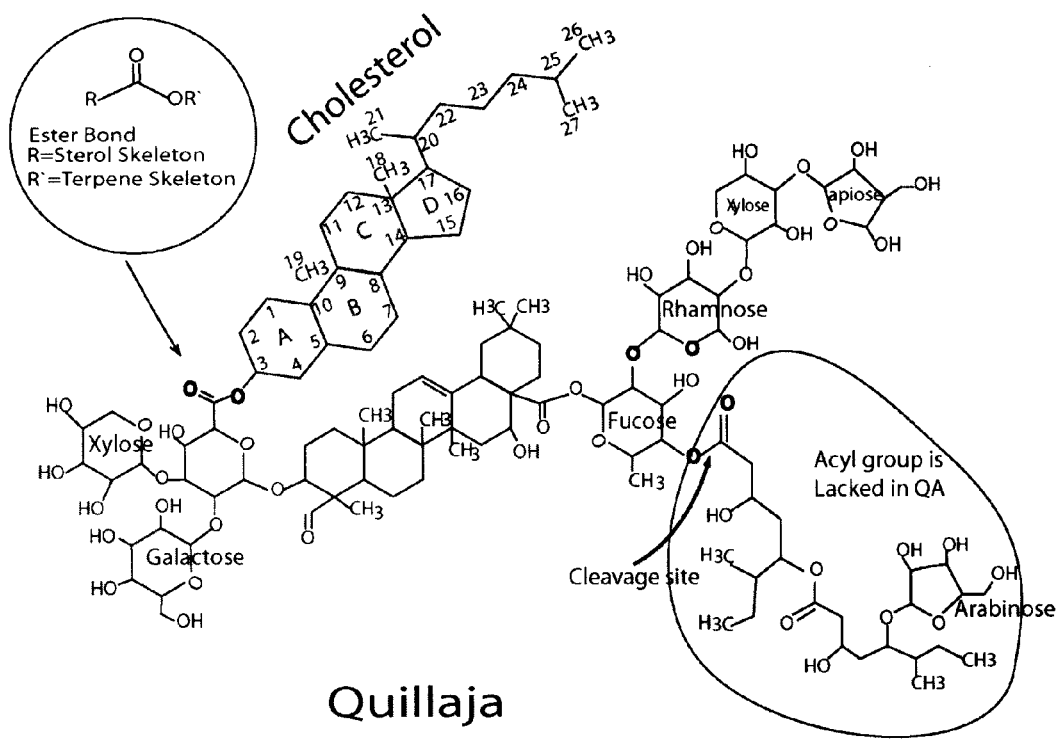
Figure 18:3

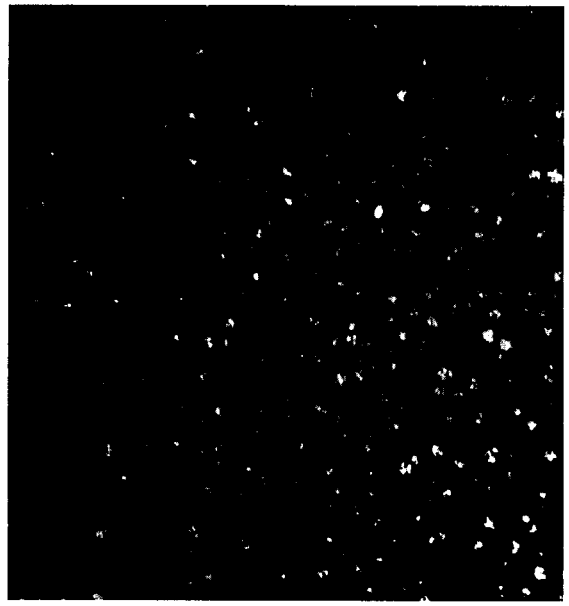
Figure 18:4A
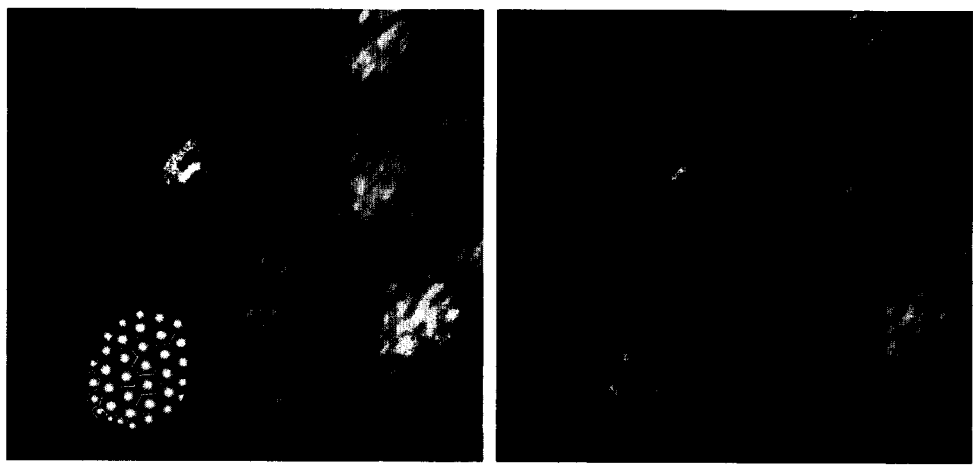
Figure 18:4B

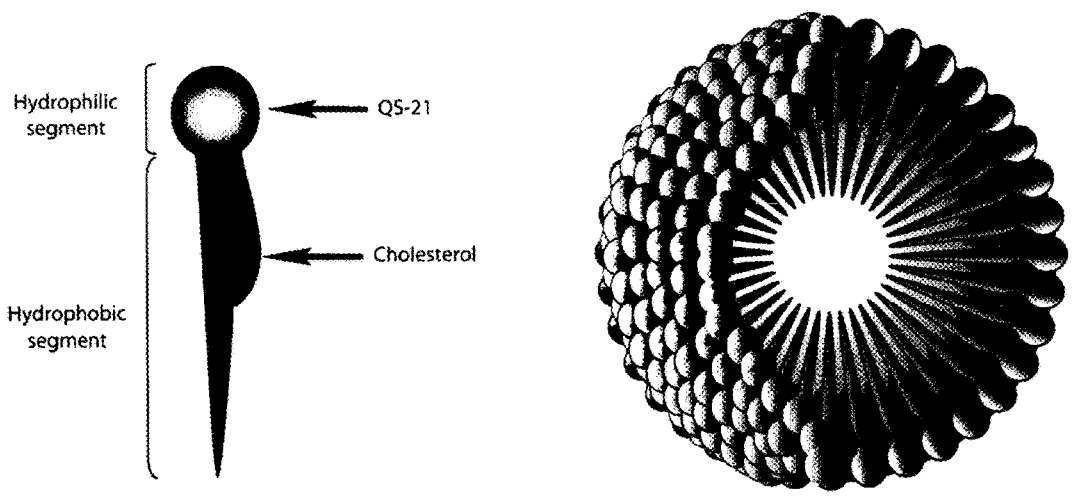
Figure 18:5
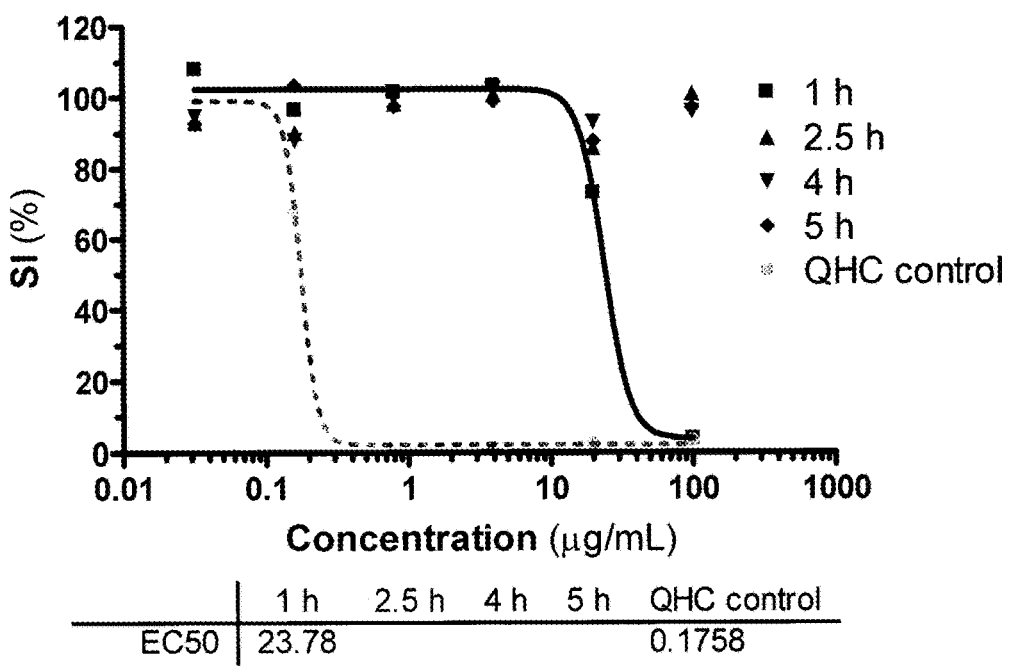
Figure 19:1

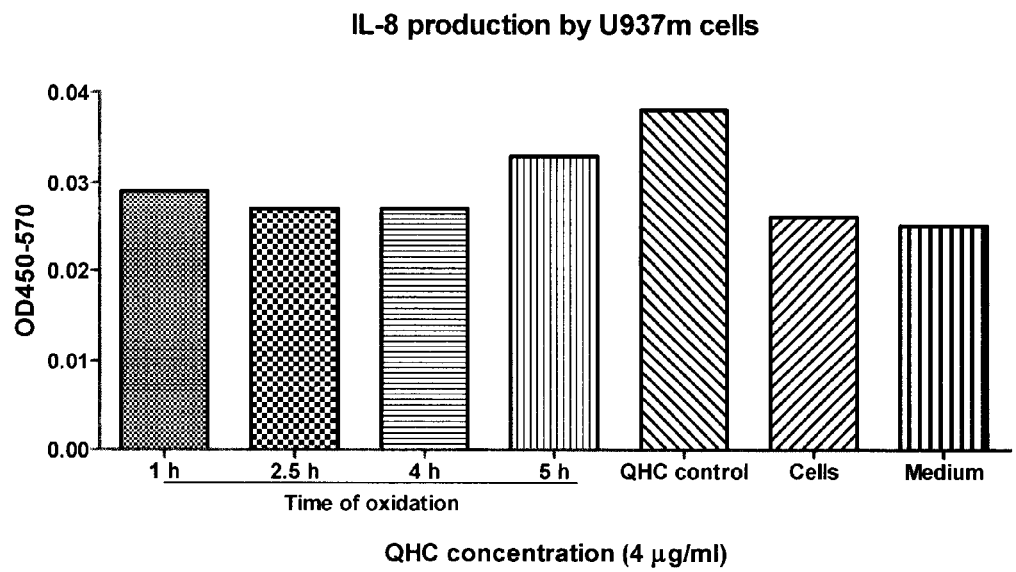
Figure 19:2
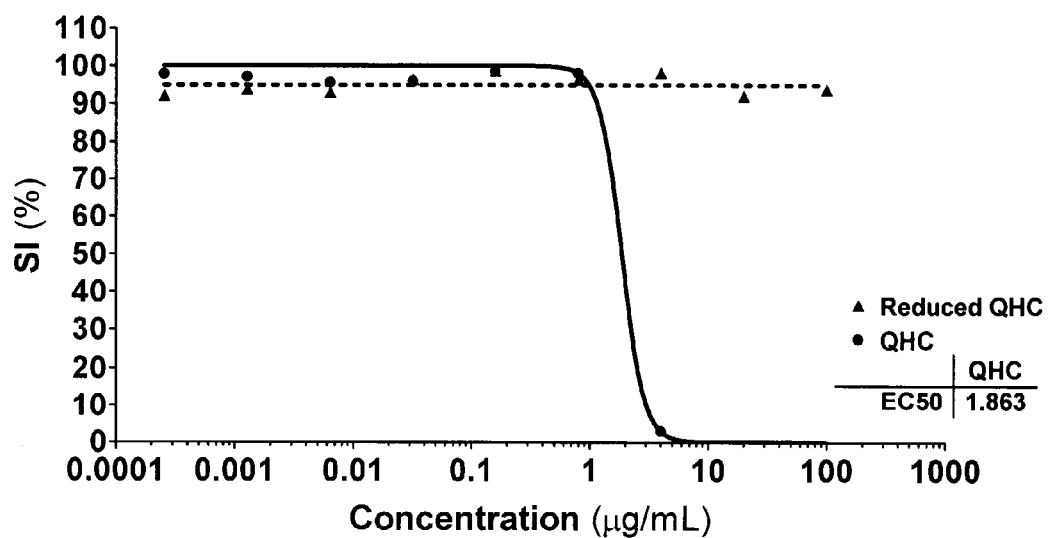
Figure 19:3

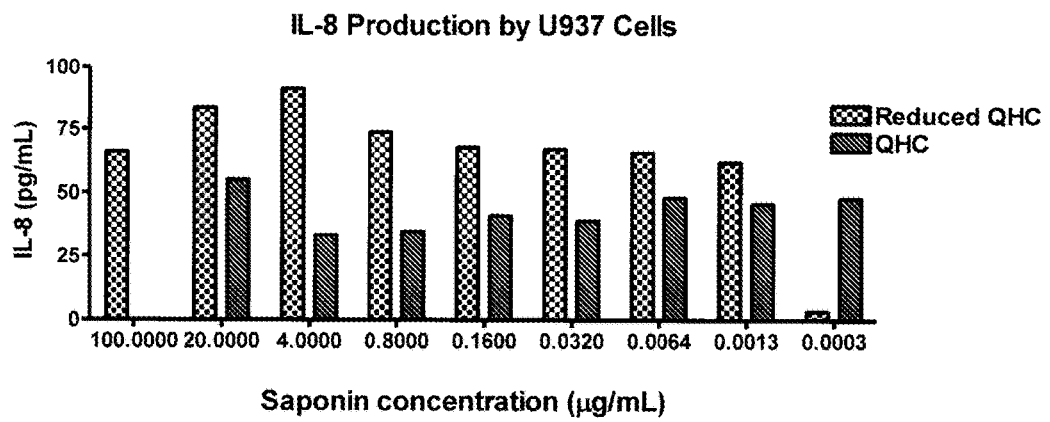
Figure 19:4
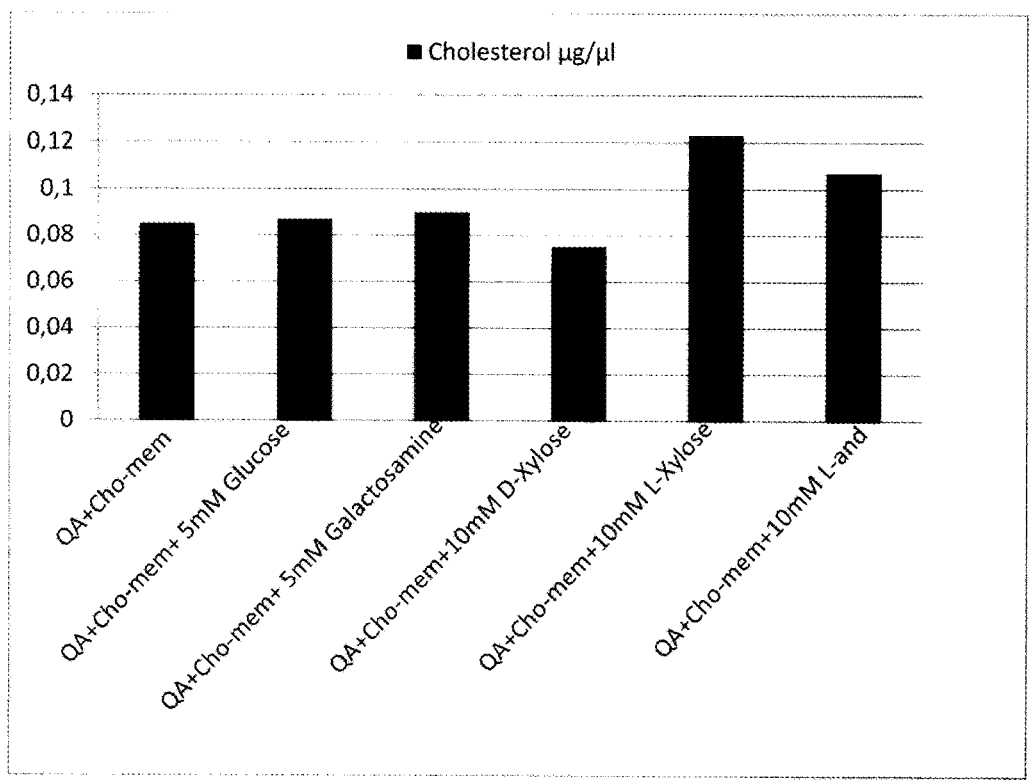
Figure 20:1

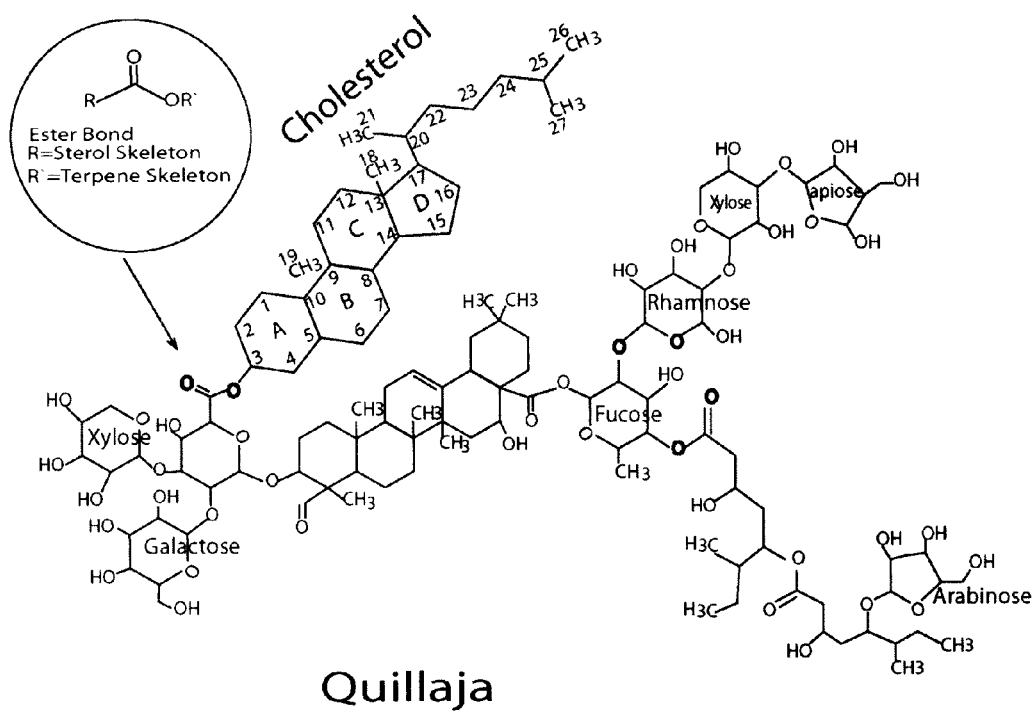
Figure 20:2

NANOPARTICLES, COMPOSED OF STEROL AND SAPONIN FROM *QUILLAJA SAPONARIA MOLINA* FOR USE IN PHARMACEUTICAL COMPOSITIONS

CROSS REFERENCE TO RELATED APPLICATION

The present application is the U.S. national stage of International Application PCT/SE2014/050380, filed Mar. 31, 2014, which international application was published on Oct. 9, 2014, as International Publication No, WO2014/163558. The International Application claims priority to Swedish Patent Application No. 1350405-5, filed Apr. 1, 2013, the contents of which are incorporated herein by reference in their entireties.

FIELD OF INVENTION

The present invention regards nanoparticles comprising sterol and a component derived from *Quillaja saponaria* Molina selected from *quillaja* acid and *quillaja* saponin, which nanoparticles do not comprise a phospholipid as an essential component. It also relates to a composition comprising the nanoparticles, and the use thereof, as adjuvant, especially in vaccines and as agents for treatment of cancer, as carriers for amphipathic or hydrophobic molecules in the medical field especially for treatment of cancer and for food related compounds. Further, it regards a method for producing the phospholipid-free nanoparticles, a method for the treatment of cancer and a method for assessing the applicability of the cancer treating method and for making food related compounds soluble in water to promote their uptake by the body.

PRIOR ART

The Immune Stimulating Complex (ISCOM) is a 40 nm particle composed by saponin from the tree *Quillaja saponaria* Molina that firmly associates with cholesterol to form hexagonal rings with 6 nm diameter. The third component is a lipid e.g. phosphatidyle choline that glues the rings to form a 40 nm spheres. This particle is used with the specific vaccine antigens incorporated into the particle or as an adjuvant particle without an antigen co-administered with the vaccine antigen in a separate particle. The ISCOM particles may be produced with the method described by Lövgren & Morein and in EP 0 436 620 as well as in WO2004/004762.

One problem with the ISCOM and ISCOM Matrix is their complex production technology. That also raises problems to use it as a carrier/delivery system e.g. to integrate molecules/compounds to be passenger or to achieve complimentary effects for pharmacological and vaccine effects or as a targeting device.

Vaccines are mostly based on whole microorganisms or subunits that promote immune responses, including both antibody and T cell responses against surface structures. Alternatively, the vaccine antigens are subunits, i.e. most often the surface proteins, but also internal/intracellular proteins or even non-structural proteins being expressed in cellular vectors. Surface proteins and carbohydrate antigens are often valued for their capacity to evoke antibody responses, not excluding that they also induce cell mediated including T-cell responses, however, mostly not cytotoxic T-cell responses. Internal and non-structural proteins are used as vaccine antigens to evoke T cell responses including cytotoxic T-cells, since antibodies do not interact with internal proteins of the infecting agents and can, therefore, not mediate immune protection at the time point of infection. In contrast cell mediated immunity including T-helper cells and cytotoxic T-cells can kill infected cells i.e. after the time point of infection. Formulations and products of the ISCOM technology are used to enhance the immunogenicity of the accessible antigens i.e. surface antigens and the antigens revealed by the disruption (internal antigens) of the agent from which and against which the vaccine is prepared[1] and WO2011/005183. Any vaccine antigen can also be produced by rDNA techniques and in many cases also synthetically produced as described by Lövgren & Morein[2]. The ISCOM technology is described in a number of patent applications, including US 2006/0121065 EP1539231A1, WO 2004/004762 and WO2005/002620).

Adjuvants in general are used to enhance level and quality of the immune responses of the antigens included in the vaccine formulation. However, there are a number of infectious agents that an unmet need is prevailing regarding protective vaccines and that (new) that immune protection is escaped by;

Escape mutants (human influenza virus, corona virus in chicken (infectious bronchitis virus [IBR]), hepatitis C virus (HCV)

Not revealing antigenic determinants
Inaccessible-hidden (*staphylococcus aureus* [SA], *streptococcus equi*)
Immune dominance by other antigenic determinants in the microorganism exemplified by influenza virus in man, parvovirus causing alution disease in mink, hepatitis C virus (HCV) in man.
Inducing immune responses that exacerbate disease (parvovirus [alution disease] mink)
Vaccines intended for species of pathogens having many to almost innumerable variants making it difficult/too costly alternatively making it more economical to produce a sufficiently covering vaccine e.g. HIV and Hepatitis C in man. It is also well-known that there are a number of vaccines that need several even as many as up to 23 vaccine components from the same number of strain variants e.g. carbohydrate variants (conjugate vaccines e.g. *Haemophilus influenzae, Meningococus miningitides, Streptococcus pneumonia, Streeptococcus pyogenes, Pneumococcus pneumonie* and also *Staphylococcus aureus*) having various capsule antigens.
Other unmet needs prevails for various Gramm+ cocci e.g. *Staphylococcus* spp in animals particularly a need is required for vaccines protecting against mastitis in ruminants, caused by against *S. aureus, Streptococcus* spp in horse (Str. Equi, Str. *Zooepidemicus*), in cattle (Str. *agalacti*, Str. *dysgalacti* and Str. *Uberis*)
Antigenic sin (FLU) or carrier induced epitope suppression antigen (CIES).
Fast replicating agents e.g. Human immune deficiency virus (HIV) complicates the escaping immune protective mechanisms of the host by new upcoming variants including those induced by vaccines.
DNA and RNA vaccines lack in many cases adjuvants Thus, there is an unmet need to increase the capacity of vaccines to meet upcoming situations that e.g. lead to epidemics and even more to pandemics or to improve the possibility to keep protective value of a vaccine by evading negative effects of escape mutation or to compensate immunity lost by escape by mutation, or to enhance immune protection to upcoming variants due to mutations during the infection. For that reason also new particulate vaccine adjuvants may be required with the flexibility to adapt its steering of the immune response to an immunological profile required for protection against a particular pathogen.

Cancer is treated in various ways including surgery, irradiation and by pharmaceuticals i.e. cytostatic drugs. The medical treatment generally by cytostatic drugs cause severe side effects like irradiation therapy often causing severe side effects. Thus, there is an unmet need to have a medical treatment that is well tolerated by the patients. International patent publication WO2008/063129 and Hu et al[3], describes nanoparticles comprising cholesterol, phosphatidylcholine and *Quillaja* saponin fractions ASAP (acyl-saponin, corresponding to QS 21 or QHC) or DSAP (desacyl-saponin, corresponding to QS 7 or QHA). These particles named KGI and BBE are described to kill cancer cells at 30 to 40 fold lower concentrations than they are killing normal cells of similar origin as described in the invention "Killcan, New Use" in the patent application PCT/SE 2007/050878 and WO2008/063129 and Hu et al[3]. These particles have similar production complexity as those described for ISCOM and ISCOM Matrix.

Many potential pharmaceuticals cannot be developed because there solubility in water could not be achieved including their use in the fields of vaccine/adjuvant and drug delivery including anticancer pharmaceuticals. If such potential pharmaceuticals were taken from shelf and rendered soluble in water some of those would enrich the medical market.

SUMMARY OF THE INVENTION

The present inventors have identified a need for a new form of nanoparticle to be used as anticancer pharmaceutical, carrier/delivery particle for pharmaceuticals and as adjuvant that can compensate for the shortcoming of commercially available adjuvant-vaccine formulations.

A problem with the ISCOM technology is the complex procedure to formulate the particles based on detergent solubilisation of the *Quillaja* components, cholesterol and the third component e.g. phosphatidyl choline e.g. using ultra filtration, tangential flew, dialysis or centrifugation techniques. All of those techniques as described by Lövgren & Morein[2], cause loss of material during the production process.

Moreover, the ISCOM technologies are not readily suitable for integration of other hydrophobic or amphipathic molecules since methods so far developed allow the strong tendency of such compounds to spontaneously form stable complexes (self-assembly) in water e.g. micelles not being integrated into the ISCOM formulation e.g. by hydrophobic interaction.

The present invention relates to a phospholipid-free nanoparticle comprising sterol and at least one saponin.

In contrast to the present invention, lipid containing particles such as liposomes, ISCOM, ISCOM MATRIX, posintros and various kinds of liposomes for the preparation and use in pharmaceuticals including adjuvant formulations to enhance the efficacy of vaccines and in vaccine formulations and formulations for treatment of cancer contains lipids like phospholipids e.g. phosphatidylserin and phosphatidylcholine, stearylamin etc.

The nanoparticles according to the invention may also be used as delivery systems for one or several compounds e.g. for pharmaceuticals including those used for treatment of cancer and nutrition related compounds where the additional substance(s) provide additional functions and complementary modes of action.

The advantage of the nanoparticles according to the invention merits them as replacements for the prior art formulations including a broadened application as adjuvants to cover new variants of a pathogen e.g. upcoming pandemics described above.

The present invention provides an easy production process with virtually no losses, due to the evaporation technology. That does not exclude the use of techniques as described for the production of ISCOMs or ISCOM Matrix (see above).

Aspects of the invention are described in the independent claims. Preferred embodiments are set forth in the dependent claims.

BRIEF DESCRIPTION OF THE DRAWINGS

FIG. 13A1. Immunization schedule
Experimental design (C56Bl6 mice, 6 mice/group, 200 μl/dose, s.c. two immunizations, 4 weeks apart)
Group 1 (Abisco Control): Influenza 1 μg+ISCOM −5 μg
Group 2 (G3-High Dose): Influenza 1 μg+G3-5 μg
Group 3 (G3-Midium Dose): Influenza 1 μg+G3-2.5 μg
Group 4 (G3-Low Dose): Influenza 1 μg+G3-1 μg
Group 5 (G3 with DT): Influenza 1 μg+G3-2.5 μg
Group 6 (Non-adjuvanted, Antigen Control): Influenza 1 μg
Group 7 (Non-immunized Control)
Evaluation
Blood for antibody responses. Spleen cells at necropsy for cell-mediated immunity including proliferation test, IL-4, IFN-gamma.

FIG. 13A2. HI antibody response of mouse serum measured at 3 weeks after the $1^{st}$ immunization FIG. 13A3. HI antibody response of mouse serum measured at 4 weeks after the $2^{nd}$ immunization FIG. 13A4. Cytokine responses of mouse spleen cells at 4 weeks after the $2^{nd}$ immunization FIG. 13B1 Survival rate recorded for 6 days post the challenge infection FIG. 13B2 Lung virus titers at day 4 and 6 after the challenge infection FIG. 13B3. HI antibody against the vaccine and the challenge starins of flu virus FIG. 13B4. Virus neutralization antibody against the vaccine and the challenge strains of flu virus. No response to the challenge virus A/PR/8/34 and significant response to the vaccine strain tested A/Cal/7/2009.

FIG. 13B5 The proportion of polymerase A $(PA)_{224-233}$ specific $CD8^+$ T cells FIG. 13B6 The proportion of nucleo protein $(NP)_{366-374}$ specific $CD8^+$ T cells FIG. 13B7 The proportion of IFNγ+ CD3+CD8+ cells representing cytotoxic T cells FIG. 14A. The G3/VLX40 formulation in the water solution (the right column) has high cancer cell (U937) killing effect. In contrast to VLX40 alone in the water solution (the left column) has low cancer cell killing effect indicating high solubility of G3/VLX40 formulation and low cancer cell killing effect of the VLX40-DMSO formulation FIG. 14B. VLX40 DMSO formulation as non-soluble sediment (left column) has high anticancer activity in the precipitates. In contrast the scanty precipitate of the G3-VLX40 (right column) formulation had low anticancer cell activity indicating that the anticancer cell activity essentially was located to the water phase.

FIG. 18:1. Cholesterol measurement and the output percentages calculation in different experiments. The bar above 20 is the average percentage FIG. 18:2A. A common basic structure reported for *Quillaja* saponin as described by Kensil et al[4] and used by Bankefors[5] in his Thesis.

FIG. 18:2B. Fatty Acid transfers to Cholesterol by LCAT. Lectin Cholesterol Acyltransferase LCAT transfers the free fatty acid from the phosphatidylcholine to the free hydroxyl group of cholesterol-generating cholesteryl ester and lysolecithin. W. David Nes et al 2011.[6]

FIG. 18:3. The structure of Cholesterol-*Quillaja* Saponin complex. The circled structure to the left shows illustrated ester bonding between the Carboxyl group in QA (R') that reacts with the free hydroxyl group in Cholesterol (R). The initial by hydrogen and Van Der Waals binding open for close monocular contact that can lead to ester bonding[6] and further on a strong hydrophobic interaction between terpene (*Quillaja*) and sterol (cholesterol) groups as illustrated above. Regardless fractions of *Quillaja*, all fractions including A and C have triterpene skeleton, glucuronic acid, galactose and xylose. The major variation is related to the acyl chain present on QHC but lacking on QHA circled in the figure.
Note the Xylose is linked to the glycoronic acid (arrow) explaining the blocking effect of Xylose.

FIG. 18:4 A. Analyses of G3 particles by transmission electron microscopy (160 k magnification) the red bar=100 nm. Electron micrograph of G3 particles following negative staining. G3 particles are typically rigid, hollow, spherical, approximately 20 nm in diameter.

FIG. 18:4 B. Analyses of G3 particles by transmission electron microscopy (220 k magnification). Electron micrograph of G3 particles following negative staining. G3 particles are typically rigid, hollow and spherical. To the left, shows illustrated structure of G3 particle.

FIG. 18:5. Complex micelles like formation by QS-21 and Cholesterol held together by hydrophilic and hydrophobic interactions.

FIG. 19:1. Oxidations of *quillaja* sugars on the QHC fraction by periodate treatment (See Material and Methods). The effect was tested on the U937 cancer cells and evaluated by Alamar Blue assay for survival index and compared with the non-modified QHC control. Oxidation abolished the anticancer effect on cells measured by ECM).

FIG. 19:2. The effect of oxidation of *quillaja* sugars on the QHC fraction by periodate treatment was tested on U937 for IL-8 production measured by ELISA after 48 hours of incubation and compared with a non-modulated QHC control. Oxidation abolishes IL8 production.

FIG. 19:3. The reduced QHC and untreated QHC in serial dilutions from 100 to 0.032 μg/mL were tested on U937 cells. Survival index was evaluated by Alamar Blue assay and compared with the non-modified QHC control.

FIG. 19:4. The reduced QHC and untreated QHC in serial dilutions from 100 to 0.032 μg/mL were tested on U937 cells. After 48 hour incubation at 37° C., supernatants were collected and IL-8 production was measured by ELISA.

FIG. 20:1. Cholesterol concentration in G3 formulation solutions

FIG. 20:2. The Carboxyl group in QA reacts with the free hydroxyl group in Cholesterol by hydrogen and Van Der Waals binding possibly leading to an ester bond and further on a strong hydrophobic interaction between terpen and sterol groups in QA and Cholesterol as illustrated above.

DEFINITIONS

Figure 1A:
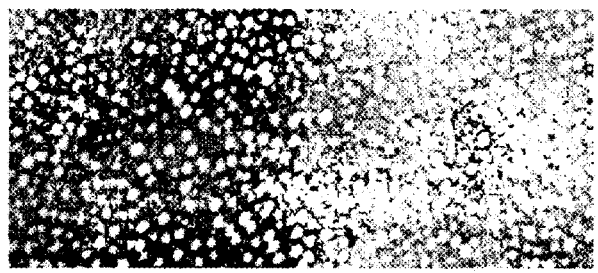
FIG. 1A. The electron microscopy (EM) shows nanoparticle comprising cholesterol, QHC and diterpenoid in a molar ratio of 1:1:0.5. The particles have a mean diameter of about 20 nm according to the invention. It is distinctly different from an ISCOM particle of about 40 nm as depicted in FIG. 1B. Particles according to the invention without the diterpenoid have the same morphology.

All terms and words in the present specification shall be construed as having the meaning usually given to them in the relevant art unless specifically indicated otherwise. For the sake of clarity, a few terms are defined below.

A vaccine formulation is a pharmaceutical formulation that is used prophylactically and improves/enhances protective immunity to/against one or more particular diseases. A therapeutic vaccine according to the invention can be used to cure disease when an antigen specific for a component connected to the disease is included in the formulation with the invention or, as is particular for cancer treatment, the antigen is present in the cancer/tumor. A vaccine includes an "antigen" that elicits an immune response in the treated subject and, optionally, a substance added to a vaccine to improve the immune response called an "adjuvant".

An "antigen" is thus the active specific part in a vaccine and may be the entire micro-organism, such as virus or bacteria, causing the disease that the vaccine is aimed at improving immunity to. It may also be a part of said micro-organism a subunit, such as a protein (a sub-unit) a part of a protein, a protein isolated from the pathogenic microorganism or produced by rDNA technique or synthetically produced then often called peptide. A peptide has fewer amino acids than a protein.

An "adjuvant" is a vaccine constituent that enhances the level and or the quality of the immune response to the antigen part of the prophylactic or therapeutic vaccine.

A nutrition related compound is any compound related to nutrient including vitamins health active substances taste improving compounds.

DETAILED DESCRIPTION OF THE INVENTION

The invention regards a nanoparticle comprising at least one sterol, e.g. cholesterol and a component from *Quillaja Saponaria* Molina (QuilQ) selected from *quillaja* saponin, characterized in that said nanoparticles do not comprise a phospholipid and in that the sterol molecule is bound by a hydrophobic bond between a hydroxyl group of the sterol and terpene moieties in a Quil A micelle and by an hydrophilic ester bond between a sterol OH$^-$ and COOH$^-$ or aldehyde groups in the QuilA micelle.

The nanoparticle may further have one or more of the following characteristics:
a particle diameter <40 nm. e.g. in the range of 10-40 nanometers, preferably 12-35 nanometers or 15-25 nanometers,
the particle is built up 6 nm hexagonal rings built up by cholesterol and *quillaja* molecules subunits,
the molar ratio of cholesterol vs *Quillaja* in the particle of 1 Mol cholesterol and 2 Moles of *Quillaja* saponin.
several particles are densely packed, well dispersed and colloidal in water.

The nanoparticles may be produced as described in claim 23.

The sterol may be selected from cholesterol, cholestanol, caprostanol, phytosterols, e.g. stigmasteroll sitosterol, mycosterols, e.g. ergosterol, preferably cholesterol and vitamin D3 or any hydrophobic compound the is exposed in water to react covalently with reactive group in the water soluble including suspension in water of a micelle.

According one embodiment the nanoparticles have the formula of claim 4, wherein each of R1 to R7 may designate glucose, fucose, apiose, arabinos, rhamnos, xylose and galactose, glycoronic acid, a bond or hydrogen atom and X represents a hydrogen atom, a bond or an acyl group.

The substituents may represent the following groups.

| | R1 | R2 | R3 | R4 | R5 | R6 | R7 | R8 | X |
|---|---|---|---|---|---|---|---|---|---|
| QHA | GlcA | Glc | Xyl/Api* | Fuc | Rha/Arab | Xyl | Api | — | H |
| QHC | GlcA | Glc | Xyl/Api | Fuc | Rha/Arab | Xyl | Api | Ara | Acyl |
| QS-21 | GlcA | Glc | Xyl/Api | Fuc | Rha/Arab | Xyl | Api | Ara | Acyl |

According to one embodiment the OH group of cholesterol is bound to a acyl group X of the saponin.

The particle is hold together by hydrophilic ligand binding, hydrogen binding, electrostatic-, ionic-ionic binding covalent bindings combined with hydrophobic bindings One or several molecules may be integrated into the particle by hydrophobic properties as described below. A hydrophilic ester bond is present between the sterol and the CHO-group at the 4-position of the triterpen ring (also numbered as C-23 of the skeleton).

According to one embodiment the sterol is cholesterol (3β)-cholest-5-en-3-ol of the formula:

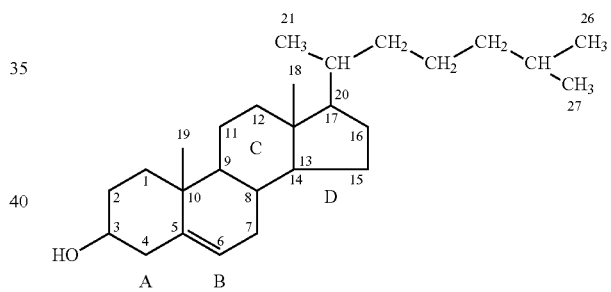

bound with its 3-OH group in the acyl bond, which preferably is an ester bond
R=Sterol skeleton
OR'=Terpen skeleton
Ester bond

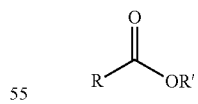

Figure 16:
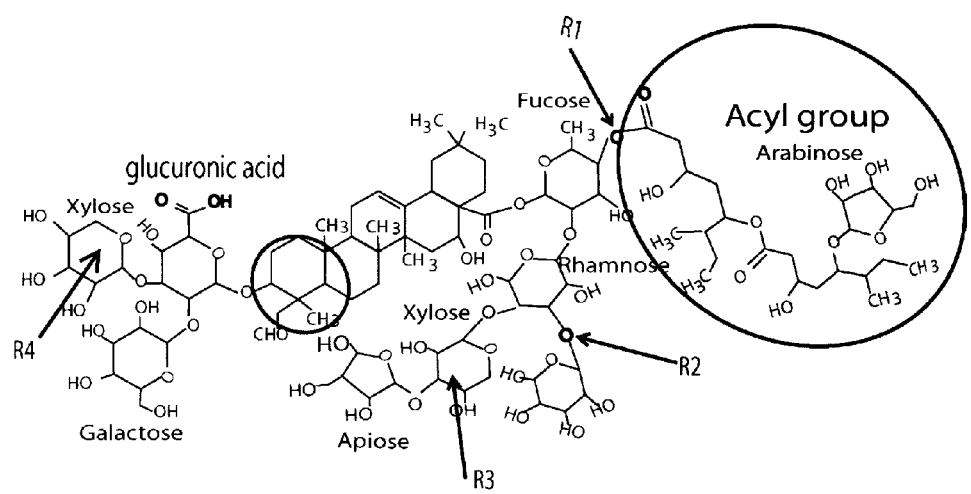
FIG. 16. The *quillaja* molecule has a triterpen skeleton, a back bone on which a number of hexose and pentose sugars are attached. One terpen ring (green ring) harbors an aldehyde group (CHO) in position 4 being the only group in the water phase. R1 to R4 are potential bindings sites on sugar moieties (see figure). For more details see text.
Figure 17:
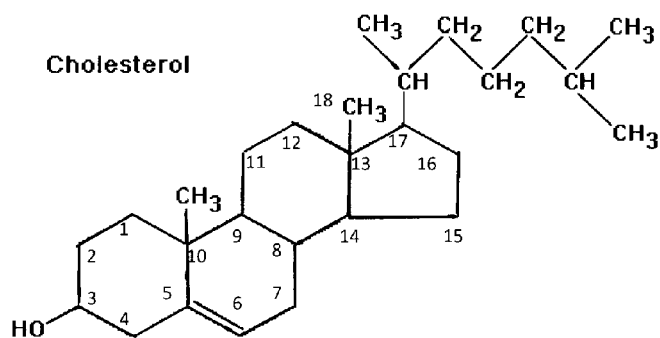
FIG. 17. Cholesterol formula with numbered carbon molecules. In position 3 is the only polar water soluble group that can react with hydrophilic bonds.

The resulting particle according to the innovation differs from ISCOMs with regard to size, wherein the particles according to the invention are below 40 nm, around ~20 nm whereas ISCOMs are ~40 nm. Thus, the nano particle of the invention may have a diameter in the range of 10-40 nanometers, preferably 12-35 nanometers or 15-25 nanometers. The size will to an extent dependent on the load of integrated other molecules than cholesterol and the *quillaja* molecule The *Quillaja* molecule has a triterpen skeleton a backbone on which a number of sugars i.e. hexos and pentos sugars attach. There are many variants depending on different triterpens i.e. the backbone and variants of sugar moieties, see "*Quillaja* extracts, Type 1 and Type 2", First draft prepared by Silvia Resnik© FAO 2004 Chemical and Technical Assessment (CTA), 61st JECFA. The essential difference of biological activity is the presence and lack of an acyl chain linked at R1 (marked in FIG. 16). The basic formula of the QA-molecule is depicted in FIG. 16, with the aldehyde group (CHO) in position 4 on the specific terpen ring. The CHO group has the only atoms facing into the water. The only atoms on the sterol, e.g. cholesterol (FIG. 17), that are polarized to be in a water phase, are the proton $H^+$ and $O^-$ supplying electrons of the hydroxyl moiety. They can react with the CHO group on terpen (see FIG. 18: 2A). Thus, the $OH^-$ group of cholesterol is polarized at an electron dense part round the $O^-$ atom and a proton ($H^+$) dense part promoting the reaction with the aldehyde group in the terpen ring. Thus, both the sterol of cholesterol and the triterpen skeleton have only one molecule group each in the water phase that can react with each other requiring a binding molecular group. Such a binding groups between rings tied by carbon molecules (C) are named carbonyl groups. Such carbonyl groups are e.g. ketone, ester, amide, acid anhydride or acyl halide. In FIG. 18:2A an ester binding is illustrated as a bond between the C position 3 in the sterol and C in position 4 of the specific terpen ring.

Terpen=R—C(4)-ester-C(3)-OR=Sterol

Other bindings are R1, R2, R3, R4, R5, R6, R7, R8 and X on sugar moieties see claim 4. Those bindings can strengthen the hydrophilic bindings in a first instance by carbonyl linking, but do not exclude or substitute the carbonyl binding of the terpen moiety to the sterol, which creates the molecular close vicinity of the sterol and terpens required to extract the sterol and incorporate that into the terpen hydrophobic centre of the *quillaja* micelle.

A sequence in the water phase of the *quillaja* micelle is that the hydrophilic surface of the micelle that is negatively charged interacting with $H^+$ ions in ligands including hydrogen bonds, ionic bonds i.e. electrostatic bonds facilitating the close vicinity of the hydroxyl group of cholesterol and the aldehyde group of the terpen. Thus, the sugars create an outer hydrophilic binding and the CHO and OH groups an inner hydrophilic binding making the close vicinity to create hydrophobic interaction between sterol and terpen composing the hydrophobic centre of a very stable micelle like construction. That construction can be used as a carrier for pharmaceuticals, hydrophobic molecules for food etc.

To note extra hydrophilic bindings at R1, R2, R3, R4, R5, R6, R7, R8 and X on the sugar moieties constituting the outer hydrophilic layer of the *quillaja* micelle will further strengthen the nano particle here described.

The strong bindings are not cross linking in the water phase which is essential because that may change the configuration and the biological effect and the possibility to the body to process the molecule.

A conjugation to R1, R2, R3, R4, R5, R6, R7, R8 and X might be useful for some other uses including medical uses i.e. as molecular carrier functions.

Only OH-group of the artificial membrane based on cholesterol is facing into water and can react with HO group the only hydrophilic group on the *quillaja* terpen. The close vicinity created between the sterol and terpen facilitates the hydrophobic interaction leading to the invention.

*Quillaja* saponin or any of its fractions with a common triterpenoid skeleton also named *Quillaja* acid may be used. There are so far 4 forms of *quillaja* acids described. *Quillaja* saponins are forming chains with a number of sugars either with an acyl group i.e. an acyl-saponin (ASAP) or without the acyl chain i.e. desacyl-saponin (DSAP) as described in e.g. Hu et al[3].

The saponine may be a crude or raw, or non-fractionated extract of Quil A comprising a mixture of saponins or a semi purified forms thereof such as *Quillaja* Powder Extract (Berghausen, USA), *Quillaja* Ultra Powder QP UF 300, *Quillaja* Ultra Powder QP UF 1000, VetSap or VaxSap (all four from Natural Responses, Chile) or from Prodalysa, Santiago, Chile. The purified saponin fractions C and B solitary or combined together with may be used. The B and C fractions are described in WO 96/11711, the B3, B4 and B4b fractions described in EP 0 436 620. The fractions QA1-22 described in EP 0 3632 279 B2, Q-VAC (Nor-Feed, AS Denmark), *Quillaja Saponaria* Molina Spikoside (Isconova AB, Uppsala Science Park, 751 83, Uppsala, Sweden).

The saponin may be hydrophilic. Theses desacylsaponins do not contain fatty acids i.e. the acyl group of FIG. 16, and may be selected from fractions 4, 5, 6, 7, 8, 9, 10, 11, 12, 13, 14 and 15 of Quil A, especially fractions 7, 8, 9, 10, 11, 12, 13 and 14 described in EP 0 3632 279 B2 and fraction A of Quil A or crude Quil A.

The saponin may be hydrophobic saponin and selected from saponins that do contain fatty acids e.g. in the 4-position in the triterpenoid aglycone of the saponins from *Quillaja Saponaria* Molina, acylsaponins such as fraction C and B of Quil A or fractions from the region between fractions A and B and fractions 15, 16, 17, 18, 19, 10 and 21 described in EP 0 3632 279 B2, especially fractions 17 and 18 are suitable here. Preferably *quillaja* saponin fraction QHA, QHB and/or QHC may be used.

The ratio between cholesterol and *quillaja* saponin may be from 1:10 to 10:1, preferably from 1:2 to 2:1.

The nanoparticles according the invention may further comprise at least one an amphipathic or hydrophobic or hydrophilic molecule, which may be selected from an antigen, an adjuvant, a targeting molecule, a pharmaceutical compound and a food related compounds. Examples of potential binding sites for hydrophilic molecules are the R1, R2, R3, R4, R5, R6, R7, R8 and X positions of claim 4.

The antigen may be any antigen with amphipathic or a hydrophobic groups as described in EPC-patent application 0 109 942, or rendered to have a hydrophobic region by rDNA expression and produced by cells or chemically synthesized. The adjuvant may be any adjuvant with amphipathic or hydrophobic groups such as those obtained from *Quillaja saponaria* Molina.

One or more compounds molecules may be incorporated into G3 for complementary functions e.g. as targeting device or as antigen or complementary antigens in the use of vaccines for immune modulatory functions described in EP 9600647-3 (PCT/SE97/00289 or as pharmaceutical including anticancer or nutritional effects. To be incorporated into G3 particles the molecules require hydrophobic domains or are electrostatic attached to the G3 particles. Compounds that do not have hydrophobic portions may be coupled to molecules having such molecules before or after incorporation into the G3 particle as described for a similar particle in EP 1800564.

Any adjuvant may be incorporated such as, natural or synthetic including synthetic or semi synthetic *quillaja* saponin or saponin fractions or derivates thereof from *Quillaja saponaria* Molina, lipid A or derivates or synthetic versions thereof, cell wall skeleton but not limited to mentioned adjuvant compounds. A Diterpenoid (DT) supplied by Javier Saints, Prodalysa, Santiago, Chile may be used as an adjuvant and a nutritional (from *stevia* a sweetening agent). The diterpenoid (DT) has been integrated into the nanoparticles according to the invention resulting in typical small nanoparticles of 17 nm.

Lipid-containing receptors that bind to cell-binding components, including cholera toxin's receptor, which is the ganglioside GM1, and focused blood group antigen may be used. The cell-binding components can also function as mucus targeting molecule. The technology for complexes comprising are described in e.g. WO97/30728 and can be applied to G3 particle both for anticancer treatment and for vaccine use. Any sub fragment of *Quillaja saponaria Molina* may be used solitary or in various combinations.

Receptors supplied with hydrophobic tail/region intended to capturing molecules to the invented particle to supply desired complementary properties e.g. different mode of cancer cell killing e.g. monoclonal antibodies that both target cancer cells and also have cell killing effect is one carrier-delivery option.

Components that may be integrated into the nanoparticle are food related compounds and pharmaceuticals including anticancer drugs including receptors for antibodies or monoclonal antibodies such as Fc receptors or the DD of Protein A of *Staphylococcus aureus* (WO2011/005183).

The carrier/delivery device of the invention may be used for any substances that are not soluble in water and which can be rendered soluble by incorporation into G3 particles.

The nano particles of the invention may incorporate antigens and/or passenger antigens and/or Diterpenoid (DT) for strengthening of the immune response.

The production method of nanoparticles disclosed by the present invention is simpler than for ISCOM and more suited to incorporate hydrophobic and amphipathic molecules. Thus, the inventive nanoparticle is a nanoparticle suited for delivery of vaccine antigens, drugs for anticancer treatment as well as for any kind of drug. The particle produced as described herein can also be supplemented with integrated amphipathic molecules (lipids such as stearylamine etc.) to be used for covalent linking other molecules e.g. drugs or vaccine antigens, or for electrostatic linking, lectin linking as described Morein et al[1] and in WO2004/004762. Approximately 40% of identified potential new drugs by pharmaceutical companies are poorly water soluble[7]. Low water solubility tends to the limited bioavailability and absorption of these agents[8]. The developments of a suitable oral formulation for some drugs have always problems which have very low water solubility. Examples of such drug are griseofulvin, phenytoin, digoxin, sulphathiazole and chloramphenicol.

The particle may further comprise cancer targeting molecules such as surface antigens from cancer cells, virus surface antigens and influenza antigens.

Surface molecules from microbial membranes may be incorporated by hydrophobic interaction as originally described by Morein et al[1] and in EP 242380. Other molecules e.g. produced by rDNA technology or synthetically produced can be incorporated as described in WO 2002/080981 and WO 2004/030696.

Such targeting molecules include envelop proteins from viruses such as influenza and respiratory syncytial viruses having affinity to respiratory tract e.g. to target forms of lung cancer, or CTA1DD being the A1 part of the A subunit of cholera toxin incorporated into KGI or BBE formulations as described by Lycke et al[9]. CTA1DD is rationally designed of three main components, each contributing complementary effects. CTA1 is the enzymatically active subunit of cholera toxin that is converted non-toxic by separation from the A2 and B subunits. Fused to DD from protein A from *Staphylococcus aureus* it targets B cells. More generally, mono and polyclonal antibodies can be incorporated into the particles as described in EP 0 109 942 B1, EP 0 242 380 B1 and EP 0 180 564 B1.

The invention also regards a composition comprising one or more nanoparticles. The composition may comprise different *quillaja* saponin fractions each incorporated in different nanoparticles.

Thus, two different saponin fractions may be complex bound in one G3 particle and the other one (the other ones) of the at least two different saponin fractions is (are) complex bound in another (other) physical different lipid containing particle(s).

The different saponins may be hydrophilic and hydrophobic saponins respectively. The particle may contain at least fraction C or at least fraction B or at least any fraction between fraction C and B of Quil A and at least one other fraction of Quil A. Thus one particle may comprise fraction C only; fraction C and at least one other fraction of Quil A; fraction C and one or more fractions of Quil A; fraction C and fraction A of Quil A: crude Quil A. The particle may also contain fraction B only; fraction B and at least one other fraction of Quit A; fraction B and one or more fractions of Quit A; fraction B and fraction A of Quit A. The above combinations of fractions may also be in different lipid particle or in the same lipid particle.

Thus, mixtures of lipid containing particles comprising hydrophilic and hydrophobic saponins in physically different particles may be used.

According to one embodiment the fraction A of Quil A may be integrated into a nano particle together with at least one other adjuvant with immunomodulating activity.

According another embodiment the at least one other adjuvant is present in free form or integrated into another separate nano particle for the preparation of an adjuvant composition.

The at least one other adjuvant may be a saponin such as a Quil A saponin.

Fraction A may facilitates the use of another adjuvant which when used by itself might be toxic in doses it is efficient and a synergistic effect including enhancement of immune responses and immunomodulating activity may be obtained.

A composition according to the invention may comprise the adjuvant fraction A from Quil A and the at least one other adjuvant in any weight ratios. Preferably fraction A of Quil A is from 2-99.9 weight %, preferably 5-90 weight % and especially 50-90 weight % counted on the total amount of adjuvants. For e.g. $Al(OH)_3$, oil adjuvants and block polymers the amount of fraction A, of Quil A may be substantially lower.

One preferred iscom composition comprises 50-99.9% of fragment A of Quil A and 0.1-50% of fragment C and/or fraction B and/or other fractions or derivatives of Quil A (hereinafter non-A Quil A fractions) counted on the total weight of fractions A and non-A Quil A fractions. Especially the composition comprises 70-99.9% of fragment A of Quil A and 0.1-30% of non-A Quil A fractions, preferably 75-99.9% of fragment A of Quil A and 0.1-25% of non-A Quil A fractions and especially 80-99.9% of fragment A of Quil A and 0.1-20% of non-A Quil A fractions counted on the total weight of fraction A and non-A Quil A fractions. Most preferred composition comprises 91-99.1% of fragment A of Quil A and 0.1-9% of non-A Quil A fractions counted on the total weight of fractions A and non-A Quil A fractions, especially 98.0-99.9% of fraction A and 0.1-2.0% of non-A Quil A fractions counted on the total weight of fractions A and non-A Quil A fractions.

According to one embodiment the nano particles comprise cholesterol and QS 7 and/or QS 21. According to one embodiment the nano particles comprise cholesterol and QS 7 and/or QS 21 and Diterpenoid (DT). The amount of QS 7 and QS 21, when both are present, may be the same as the weight % mentioned above for fraction A of Quil A and non-A Quil A fractions counted on the total weight of fractions A and non-A Quil A fractions, whereby the figures mentioned for fraction A of Quil A apply for QS 7 and the figures mentioned for non-A Quil A fractions apply for QS 21.

According to one embodiment, the molar ratio of cholesterol vs *Quillaja* in the particle is 0.2-2 mol cholesterol and 0.5-5 mols of *Quillaja* saponin. According to one embodiment, the molar ratio of cholesterol vs *Quillaja* in the particle is 0.5-1.5 mol cholesterol and 1-3 mols of *Quillaja* saponin. According to one embodiment, the molar ratio of cholesterol vs *Quillaja* in the particle is 1 mol cholesterol and 2 mols of Qyillaja saponin.

According to one embodiment, the molar ratio of cholesterol vs *Quillaja* in the particle is 1 mol cholesterol and 2 mols of *Quillaja* saponin and comprises QS 7 and QS 21 as saponin in any of the above mentioned weight ratios counted on the total weight of fractions QS 7 and QS 21, preferably 70-85% QS 7 and 15-30% QS 21.

According to one embodiment the nano-particles comprises 2-30% cholesterol, 15-30% QS 21, 50-85% QS 7 and 2-30% DT counted on the total weight of the particle.

According to one embodiment the nano-particles comprises 2-30% cholesterol, 15-85% crude Quil A and 2-30% DT counted on the total weight of the particle.

The nanoparticles and a composition comprising the nanoparticles may be used as a pharmaceutical optionally in a pharmaceutical composition further comprising pharmaceutically acceptable buffers, diluents excipients, additives, adjuvants and/or carriers.

Suitable pharmaceutically acceptable carriers and/or diluents include any and all conventional solvents, dispersion media, fillers, solid carriers, aqueous solutions, coatings, antibacterial and antifungal agents, isotonic and absorption delaying agents, and the like. The use of such media and agents for pharmaceutically active substances is well known in the art, and it is described, by way of example, in Remington's Pharmaceutical Sciences, 18th Edition, Mack Publishing Company, Pennsylvania, and USA. Except insofar as any conventional media or agent is incompatible with the active ingredient, use thereof in the pharmaceutical compositions of the present invention is contemplated. Supplementary active ingredients can also be incorporated into the compositions.

The invention also comprises a pharmaceutical composition further comprising at least one pharmaceutically active compound, such as anticancer drugs, platinum coordination compounds, taxane compounds, camptothecin compounds, anti-tumour vinca alkaloids, anti-tumour nucleoside derivatives, nitrogen mustard or nitrosourea alkylating agents, anti-tumour anthracycline derivatives, trastzumab and anti-tumour podophyllotoxin derivatives, *Quillaja saponaria* Molina and sub fragments thereof, receptors for antibodies or monoclonal antibodies such as Fc receptors or the DD of Protein A of *Staphylococcus aureus*, agents for treating cancer, such as agents selected from the group consisting of Cytarabin, Daunorubicin, Paclitaxel, Docetaxel, Cabazitaxel, Toricsel and Trabectidin, which active compound may be integrated into the nanoparticle or mixed with the composition.

The further anti-cancer agents are preferably selected from namely platinum coordination compounds, taxane compounds, camptothecin compounds, anti-tumour vinca alkaloids, anti-tumour nucleoside derivatives, nitrogen mustard or nitrosourea alkylating agents, anti-tumour anthracycline derivatives, trastzumab and anti-tumour podophyllotoxin derivatives.

The term "platinum coordination compound" is used herein to denote any tumour cell growth inhibiting platinum coordination compound which provides platinum in the form of an ion. Preferred platinum coordination compounds include cisplatin, carboplatin, chloro (diethylenetriamine)-platinum (II) chloride; dichloro (ethylenediamine)-platinum (II); diamine(1,1-cyclobutanedicarboxylato)-platinum (II) (carboplatin); spiroplatin; iproplatin; diamine(2-ethylmalonato)-platinum (II); (1,2-diaminocyclohexane)malonato-platinum (II); (4-carboxyphthalo) (1,2-diaminocyclohexane)platinum (II); (1,2-diaminocyclohexane)-(isocitrato) platinum (II); (1,2-diaminocyclohexane)-cis-(pyruvato) platinum (II); and (1,2-diaminocyclohexane)-oxalato-platinum (II); ormaplatin and tetraplatin.

Cisplatin is commercially available for example under the trade name Platinol from Bristol Myers Squibb Corporation as a powder for constitution with water, sterile saline or other suitable vehicle. Other platinum coordination compounds and their pharmaceutical compositions are commercially available and/or can be prepared by conventional techniques.

The taxane compound may be those sold under the trade name Taxol from Bristol Myers Squibb and docetaxel is available commercially under the trade name Taxotere from Rhone-Poulenc Rorer. Both compounds and other taxane compounds may be prepared in conventional manner for example as described in EP 253738, EP 253739 and WO 92/09589 or by processes analogous thereto. Carbazitaxel available from Sanofi Pasteur.

Camptothecin compounds include irinotecan and topotecan. Irinotecan is commercially available for example from Rhone-Poulenc Rorer under the trade name Campto and may be prepared for example as described in European patent specification No. 137145 or by processes analogous thereto. Topotecan is commercially available for example from SmithKline Beecham under the trade name Hycamtin and may be prepared for example as described in European patent specification No. 321122 or by processes analogous thereto. Other camptothecin compounds may be prepared in conventional manner for example by processes analogous to those described above for irinotecan and topotecan.

Anti-tumour vinca alkaloids include vinblastine, vincristine and vinorelbine referred to above. Vinblastine is commercially available for example as the sulphate salt for injection from Eli Lilly and Co under the trade name Velban, and may be prepared for example as described in German patent specification No. 2124023 or by processes analogous thereto. Vincristine is commercially available for example as the sulphate salt for injection from Eli Lilly and Co under the trade name Oncovin and may be prepared for example as described in the above German patent specification No. 2124023 or by processes analogous thereto. Vinorelbine is commercially available for example as the tartrate salt for injection from Glaxo Wellcome under the trade name Navelbine and may be prepared for example as described in U.S. Pat. No. 4,307,100, or by processes analogous thereto Other anti-tumour vinca alkaloids may be prepared in conventional manner for example by processes analogous to those described above for vinoblastine, vincristine and vinorelbine.

Anti-tumour nucleoside derivatives include 5-fluorouracil, gemcitabine and capecitabine referred to above. 5-Fluorouracil is widely available commercially, and may be prepared for example as described in U.S. Pat. No. 2,802,005. Gemcitabine is commercially available for example from Eli Lilly under the trade name Gemzar and may be prepared for example as described in European patent specification No. 122707 or by processes analogous thereto.

Capecitabine is commercially available for example from Hoffman-La Roche under the trade name Xeloda and may be prepared for example as described in European patent specification No. 698611 or by processes analogous thereto. Other anti-tumour nucleoside derivatives may be prepared in conventional manner for example by processes analogous to those described above for capecitabine and gemcitabine.

Nitrogen mustard compounds include cyclophosphamide and chlorambucil. Cyclophosphamide is commercially available for example from Bristol-Myers Squibb under the trade name Cytoxan and may be prepared for example as described in U.K. patent specification No. 1235022 or by processes analogous thereto. Chlorambucil is commercially available for example from Glaxo Welcome under the trade name Leukeran and may be prepared for example as described in U.S. Pat. No. 3,046,301, or by processes analogous thereto. Preferred nitrosourea compounds for use in accordance with the invention include carmustine and lomustine referred to above. Carmustine is commercially available for example from Bristol-Myers Squibb under the trade name BiCNU and may be prepared for example as described in European patent specification No. 902015, or by processes analogous thereto. Lomustine is commercially available for example from Bristol-Myers Squibb under the trade name CeeNU and may be prepared for example as described in U.S. Pat. No. 4,377,687, or by processes analogous thereto.

Anti-tumour anthracycline derivatives include daunorubicin, doxorubicin and idarubicin referred to above. Daunorubicin is commercially available for example as the hydrochloride salt from Bedford Laboratories under the trade name Cerubidine, and may be prepared for example as described in U.S. Pat. No. 4,020,270, or by processes analogous thereto.

Doxorubicin is commercially available for example as the hydrochloride salt from Astra, and may be prepared for example as described in U.S. Pat. No. 3,803,124 or by processes analogous thereto. Idarubicin is commercially available for example as the hydrochloride salt from Pharmacia & Upjohn under the trade name Idamycin, and may be prepared for example as described in U.S. Pat. No. 4,046,878 or by processes analogous thereto Other anti-tumour anthracycline derivatives may be prepared in conventional manner for example by processes analogous to those described above for daunorubicin, doxorubicin and idarubicin.

Trastzumab is commercially available from Genentech under the trade name Herceptin and may be obtained as described in U.S. Pat. No. 5,821,337 or PCT patent specifications WO 94/04679 and WO 92/22653.

Anti-tumour anti-tumour podophyllotoxin derivatives include etoposide and teniposide. Etoposide is commercially available for example from Bristol-Myers Squibb under the trade name VePesid, and may be prepared for example as described in European patent specification No. 111058, or by processes analogous thereto. Teniposide is commercially available for example from Bristol-Myers Squibb under the trade name Vumon and may be prepared for example as described in PCT patent specification No. WO 93/02094, or by processes analogous thereto. Other anti-tumour podophyllotoxin derivatives may be prepared in conventional manner for example by processes analogous to those described above for etoposide and teniposide.

Thuss, anticancer drugs may e.g. be chosen from 1. Polyfunctional alkylating agents: Nitrosoureas, Mustards (Nitrogen Mustards), Methanesulphonates (Busulphan), Ethylenimines 2. Other Alkylating Drugs: Procarbazine (Matulane), Dacarbazine (DTIC), Altretamine (Hexalen), Cisplatin (Platinol) 3. Antimetabolites: Antifolic acid compounds (Methotrexate), Amino acid Antagonists (Azaserine) 4. Purine antagonists: Mercaptopurine (6-MP), Thioguanine (6-TG), Fludarabine Phosphate, Cladribine (Leustatin), Pentostatin (Nipent) 5. Pyrimidine antagonists: Fluorouracil (5-FU), Cytarabine (ARA-C), Azacitidine 6. Plant alkaloids: Vinblastine (Velban), Vincristine (Oncovin), Etoposide (VP-16, VePe-sid), Teniposide (Vumon), Topotecan (Hycamtin), Irinotecan (Camptosar), Paclitaxel (Taxol), Docetaxel (Taxotere) 7. Antibiotics: Anthracyclines, Doxorubicin (Adriamycin, Rubex, Doxil), Daunorubicin (DaunoXome), Dactinomycin (Cosmegen), Idarubincin (Idamycin). Plicamycin (Mithramycin), Mitomycin (Mutamycin), Bleomycin (Blenoxane) 8. Monoclonal Antibodies, 9. Hormonal agents: Tamoxifen (Nolvadex), Flutamide (Eulexin), Gonadotropin-Releasing Hormone Agonists, (Leuprolide and Goserelin (Zoladex)), Aromatase Inhibitors, Aminoglutethimide, Anastrozole (Arimidex), 10. Miscellaneous anticancer drugs: Amsacrine, Hydroxyurea (Hydrea), Asparaginase (El-spar), Mitoxantrone (Novantrone), Mitotane, Retinoic Acid Derivatives, Bone Marrow Growth Factors, Amifostine Saponins in crude form or fractions thereof such as those mentioned above may also be used in free form, i.e. not integrated into lipid comprising particles, as anti-cancerous agents. These anticancer compounds may be mixed with, coupled on to or integrated into the lipid containing particles such as liposomes, iscom and/or iscom matrix and posintros.

It is suitable if they are hydrophobic when integrated. If not hydrophobic groups may be coupled on to them as described in EP 242380.

Non-hydrophobic compounds and especially proteins or peptides may be rendered hydrophobic by coupling hydrophobic groups to them.

The hydrophobic group that can be coupled to the non-hydrophobic compounds are straight, branched, saturated or unsaturated aliphatic chains, preferably having 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 carbon atoms, or hydrophobic amino acids or peptides or other hydrophobic structures such as steroids. The length of the hydrophobic structure is adapted to the size and nature of the protein. As an example, it can be mentioned that a peptide with 10-15 amino acids (foot-and-mouth disease virus) suitably is brought out with two tyrosines at the amino or carboxy terminal end. A protein with a molecular weight of 70,000 daltons demands about 20 hydrophobic amino acids. Testing is made empirically. Thus, one uses especially peptides with 1 to 20 amino acids, preferably 1, 2, 3, 4, 5 amino acids, especially chosen among Trp, Ile, Phe, Pro, Tyr, Leu, Val, especially Tyr; cholesterol derivatives such as choline acid, ursodesoxycholine acid.

These hydrophobic groups must be bonded to a group that can be coupled to the non-hydrophobic protein or compounds such as carboxyl-, amino-, disulphide-, hydroxyl-, sulohydryl- and carbonyl group, such as aldehyde groups.

As hydrophobic groups that can be coupled are selected preferably carboxyl, aldehyde, amino, hydroxyl, and disulphide derivatives of methan, ethane, propane, butane, hexane, heptane, octane and peptides containing Cys, Asp, Glu, Lys, preferably octanal and Tyr.Tyr.Tyr-Cys,-Asp or -Glu. The hydrophobic groups with a group that can be coupled must be dissolved in water with the aid of for example the solubilising agents and detergents mentioned above or hydrochloric acid, acetic acid 67% by volume acetic acid, caustic liquor, ammonia, depending on what substance is to be dissolved, pH is then adjusted to the neutral direction without the substance precipitating; here it is to make sure that there is not obtained a pH value that denaturates the protein to which the hydrophobic group is to be coupled. Lipid may enhance the solubilisation.

The hydrophobic molecule may be added to the non-hydrophobic compound in the molar ratio of 10:1 to 0.1:1, preferably 1:1.

Hydrophobic groups with a carboxyl group as coupling molecule can be coupled to the protein through water-soluble carbodiimides or composite anhydrides. In the first case the carboxyl group is activated at pH 5 with carbodiimide and mixed with the protein dissolved in buffer pH 8 with a high phosphate content. In the latter case the carboxy compound is reacted with isobutylchloroformate in the presence of triethylamine in dioxane or acetonitrile, and the resulting anhydride is added to the protein at pH 8 to 9. It is also possible to convert the carboxyl group with hydrazine to hydrazide which together with aldehydes and ketones in periodate-oxidized sugar units in the protein gives hydrazone bonds.

The amino groups with nitrous acid can at a low temperature be converted to diazonium salts, which gives azo bonds with Tyr, His and Lys. The hydroxyl groups with succinic anhydride can be converted to hemisuccinate derivatives which can be coupled as carboxyl groups. Aldehyde groups can be reacted with amino groups in the protein to a Schiff's base. Several coupling groups and methods are described[10-12].

The proteins, peptides or compounds so produced having received hydrophobic groups are then complex-bonded with glycoside, as described in a), but here the purification steps for removing cell fragments can be omitted.

Hydrophilic proteins having enclosed hydrophobic groups can be rendered hydrophobic by making the hydrophobic groups accessible by gently denaturating the proteins, i.e. with a low pH of about 2.5, 3M urea or at a high temperature above 70.degree. C. Such proteins may be immunoglobulins such as IgG, IgM, IgA, IgD and Ig E. The immunoglobulins can be used as antidiotypic antibodies. The proteins are obtained purified as proteins as described in (b) and then complex-bonded to glycoside as described in (a), the purification steps for removing cell fragments being omitted.

The hydrophobic or amphipatic molecule may also be chosen from phospholipids such as derivatives of glycerol phosphates such as derivatives of phosphatidic acids i.e. lecithin, cephalin, inositol phosphatides, spingosine derivatives with 14, 15, 16, 17, 18, 19 and 20 carbon atoms, phosphatidylethanolamine, phophatidylserine, phosphatidyl choline.

All above mentioned amphipathic and hydrophobic molecule, which may be selected from an antigen, an adjuvant, a targeting molecule, a pharmaceutical compound and a nutriment may be integrated into the nanoparticle or mixed therewith in a composition. The nano particle constituting an artificial membrane may contain two or more compounds to be included in the nano particle. Alternatively different compounds are incorporated into separate nano particles.

The pharmaceutical composition may be used as an adjuvant, e.g. for use in combination with a vaccine under development, for use in combination with a seasonal influenza virus vaccine, for use in combination with a pandemic influenza vaccine or for use in combination with an emergency vaccine, such as a vaccine against a biological weapon.

Thus, the invention also regards a pharmaceutical vaccine formulation comprising the G3 particles, especially as an adjuvant as mentioned above.

The invention also relates to a method for treating or preventing a disease caused or complicated by an organism, comprising administering to a subject a pharmaceutical vaccine formulation according to the invention to a person in need thereof.

Further, the invention regards a method for treatment of cancer, comprising administering to a patient in need thereof a pharmaceutically effective amount of nanoparticles or a composition according to the invention. According to one embodiment the said cancer is leukemia, lymphom, myelom, breast cancer, prostata cancer, renal cancer, pancreas cancer, ovarie cancer, brain cancer, cervix cancer, lung, cancer, liver, cancer, kidney cancel, oral cancer, blood cancer. The cancer may be situated in Adrenal gland Adrenal Gland Cancer (Adenocarcinoma of the Adrenal Gland, Adrenocorticol Carcinoma; Anus. Anal Cancer (Squamous Cell Carcinoma of the Anus); Bladder Bladder Cancer (Squamous Cell Carcinoma of the Bladder), Bladder Cancer (Transitional cell carcinoma of the Bladder); Blood, Disseminated Intravascular Coagulation, Hyponatraemia, Neutropaenic sepsis, Tumour Lysis Syndrome; Bone, Endochondroma (chondroma, Ollier's disease), Ewings Sarcoma, Osteosarcoma, (Osteogenic sarcoma), Metastases to the Bone, Bone Cancer (Chondrosarcoma of Cartilage); Bone Marrow, Chronic Myeloid Leukaemia, Multiple Myeloma, Promyelocytic Leukaemia (PML), Myelodysplastic syndrome (MDS), Chronic Lymphocytic Leukaemia, Acute Lymphoblastic Leukaemia (ALL), Acute Myeloid Leukaemia (AML); Brain, Brain Cancer (Glioblastoma Multiforme of the Brain), Brain tumour (Glioma of the Brain), Lymphoma of the Brain, Medulloblastoma/Primitive Neuroectodermal tumour (PNET) [Medulloblastoma/Primitive Neuroectodermal tumour (PNET)], Meningioma of the Brain, Neuroblastoma, Primitive neuroectodermal tumour of the brain (PNET), Brain Metastasis, Acoustic Neuroma, Brain Tumour (Astrocytoma of the Brain); Breast, Breast Cancer (Carcinoma of the Breast), Breast Cancer (Inflammatory Carcinoma of the Breast), Male Breast Cancer (Male Breast Carcinoma), Breast Cancer (Invasive Breast Carcinoma) [Invasive Breast Carcinoma (Breast Cancer)], Breast Cancer (Pre-Invasive Lobular Carcinoma; Lobular Carcinoma In Situ; LCIS) [Pre-Invasive Lobular Carcinoma (Lobular Carcinoma In Situ; LCIS; Breast Cancer)], Breast Cancer (Pre-Invasive Ductal Carcinoma; Ductal Carcinoma In Situ; DCIS) [Pre-Invasive Ductal Carcinoma (Ductal Carcinoma In Situ; DCIS; Breast Cancer)]; Caecum, Bowel Cancer (Adenocarcinoma of the Caecum); Cervix, Cervical Cancer (Squamous Cell Carcinoma of the Cervix); Colorectal, Colon Cancer (Adenocarcinoma of the Colon), Rectal Cancer (Adenocarcinoma of the Rectum)1, Head and Neck, Tonsil Cancer (Lymphoma of the Tonsil), Cancer of the larynx (Laryngeal cancer, Squamous Cell Carcinoma of the Larynx), Pharynx Cancer (Squamous Cell Carcinoma of the Pharynx), Tongue Cancer (Squamous Cell Carcinoma of the Tongue), Throat cancer (Squamous Cell Carcinoma of the Tonsil), Oral Cancer (Squamous Cell Carcinoma of the Floor of the Mouth); Kidney, Kidney Cancer (Renal Cell Carcinoma; RCC); Liver, Liver Cancer (Hepatocellular Carcinoma), Metastases to the Liver; Lung, Lung Cancer (Large Cell Carcinoma of the Lung), Pleural effusion, Lung Cancer (Adenocarcinoma of the Lung), Small Cell Lung Cancer (Carcinoma of the Lung), Non-Small Cell Lung Cancer (NSCLC), Malignant Mesothelioma of the Pleura, Lung Cancer (Squamous Cell Carcinoma of the Lung); Lymphatic System; Hodgkin's lymphoma, Hodgkin's Lymphoma; non-Hodgkin's lymphoma, Burkitt's lymphoma, Cerebral Lymphoma. Cutaneous T cell Lymphoma, Follicular lymphoma, Lymphoblastic lymphoma (non-Hodgkin's lymphoma), MALT lymphoma, Mantle cell lymphoma, Mediastinal (thymic) large B cell lymphoma. Nodal Marginal Zone B cell Lymphoma, Non-Hodgkin's Lymphoma, Peripheral T cell lymphoma, Small lymphocytic lymphoma, Diffuse large B cell lymphoma (DLBCL), Anaplastic Large Cell Lymphoma (ALCL); Muscle, Cancer of the Bile Duct (Cholangiocarcinoma Biliary Cancer), Leiomyosarcoma of Muscle, Rhabdomyosarcoma of Muscle, Soft tissue Sarcomas; Oesophagus, Oesophageal Cancer (Squamous Cell Carcinoma of the Oesophagus), Oesophageal Cancer (Adenocarcinoma of the Oesophagus); Ovary, Ovarian Cancer (Adenocarcinoma of the Ovary); Pancreas, Pancreatic Cancer (Adenocarcinoma of the Pancreas), Pancreatic Neuroendocrine Tumour (PNET); Penis, Cancer of the Penis (Squamous Cell Carcinoma of the Penis), Peyronie's Disease; Pituitary gland, Pituitary Gland Cancer (Carcinoma of the Pituitary gland), Syndrome of inappropriate antidiuretic hormone secretion (SIADH) [Syndrome of inappropriate antidiuretic hormone secretion (SIADH)]; Prostate, Prostate Cancer (Neuroendocrine Carcinoma of the Prostate), Prostate Cancer (Adenocarcinoma of the Prostate); Skin, Skin Cancer (Basal Cell Carcinoma of the Skin), Skin Cancer (Squamous Cell Carcinoma of the Skin), Merkel Cell Carcinoma (MCC), Skin Cancer (Malignant Skin Melanoma), Moles (Benign Pigmented Lesions, Benign Melanocytic Lesions, Melanocytic Naevi, Nevocytic Naevi); Small Intestine, Small Intestine Cancer (Lymphoma of the Small Intestine), Small Bowel Cancer (Adenocarcinoma of the Small Intestine); Spinal Cord, Glioma of the Spinal Cord, Meningioma of the Spinal Cord, Metastases of the Spinal Cord, Spinal Cord Astrocytoma (Tumour), Spinal Cord Cancer (Lymphoma of the Spinal Cord); Stomach, Zollinger-Ellison Syndrome (Gastrinoma), Lymphoma of the Stomach (Gastric Lymphoma), Stomach Cancer (Adenocarcinoma of the Stomach); Testicle. Testicular Cancer (Seminoma of the Testicle), Testicular Cancer (Teratoma of the Testicle); Thyroid, Thyroid Cancer (Follicular Cell of the Thyroid), Medullary Cell of the Thyroid, Papillary Cell of the Thyroid, Thyroid Cancer (Anaplastic of the Thyroid); Uterus, Gestational Trophoblastic Disease (Molar Pregnancy) [Molar Pregnancy (Gestational Trophoblastic Disease, GTD)], Uterine Cancer (Adenocarcinoma of the Endometrium); Vulva, Vulval Cancer (Squamous Cell Carcinoma of the Vulva); Other cancers, Tumour of unknown primary (TUP), Chronic Pain Syndrome, Carcinoid Tumour and Carcinoid Syndrome, Neuroendocrine Tumour; Other Cancer diseases, Anaemia of Chronic Disease, Cancer Pain, Failed Back Surgery Syndrome (FBSS), HIV AIDS (Human Immune Deficiency Virus & Acquired Immune Deficiency Syndrome), Kidney Disease—Chronic Renal Failure, Malnutrition, Ototoxicity, Petechiae skin purpura, Prostatic Intraepithelial Neoplasia (PIN).

Classification by tissue types are: Carcinoma, Sarcoma, Myeloma, Leukemia, Lymphoma, Mixed types.

The pharmaceutical compositions may be in the form of a sterile injectable aqueous or oleaginous suspension. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water. Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The solutions or suspensions could also comprise at least one of the following adjuvants: sterile diluents such as water for injection, saline, fixed oils, polyethylene glycols, glycerol, propylene glycol or other synthetic solvents, antibacterial agents such as benzyl alcohol or methyl paraben, antioxidants such as ascorbic acid or sodium bisulfite, chelating agents such as ethylene diamine tetraacetic acid, buffers such as acetates, citrates or phosphates, and agents for adjustment of the tonicity such as sodium chloride or dextrose. The parenteral preparation could be enclosed in ampoules, disposable syringes or multiple dosage vessels made of glass or plastic.

The compounds of general formula may be administered parenterally. The term parenteral as used herein includes subcutaneous injections, intravenous, intramuscular, intradermal injection of infusion techniques, electroporation (EP), for needle less injection—jet injection, gene gun, biljector as well as oral, aerosol administrations. For oral use e.g. protein A derived compound CTA1DD may be used as described by Eliasson et al.[13] having a property to targeting B-cells useful treating-cells for induction of mucosal immunity particularly in the intestinal tract but also potentially also for cancers particularly for B-cells lymphoma.

Generally, the lipid containing particles of this invention are administered in a pharmaceutically effective amount. The amount of the particles actually administered will be typically determined by a physician, in the light of the relevant circumstances, including the condition to be treated, the chosen route of administration, the actual compound administered, the age, weight, and response of the individual patient, the severity of the patient's symptoms, and the like.

The nanoparticle according to the invention may be used as an adjuvant in any vaccine against any microorganisms. I may be used on any animal such as birds, mammals such as humans, domestic animals such as cats, dogs, sheep, goat, pigs, cattle and horses. According to one embodiment the invention is used as adjuvant in a vaccine against streptococci in animals and influenza in horses.

Doses for human use may vary according to other compounds included. In view of duration of treatment the dose may range from <50 µg to 1 mg or more per day.

The invention also regards a method for assessing the applicability of the method for treatment of cancer according to the invention to an individual patient, comprising
  bringing cancer cells from said patient in contact in vitro with nanoparticles according to any one of claims 1-7 or a pharmaceutical composition according to claim 8 or 9;

measuring at least one effect indicative of therapeutic effect of said nanoparticles or pharmaceutical composition on said cancer cells;

wherein the method according to claim 10 or 11 is assessed as applicable to said individual patient if the nanoparticles or pharmaceutical composition shows a significant effect indicative of therapeutic effect on said cancer cells.

The indication of therapeutic effect can be read by down regulation of genes, which have importance in the cell cycle regulation as cycline dependent kinases (CDKs), cyclins or other molecules promoting passage over check points in the cell cycle and replication (CDK2, CDK6 and CyclineD1) or down regulation of thymindine kinase (TK) and up regulation of molecules facilitating the cell differentiation, differentiation markers such as IL-8, FOXC1, HDAC5, INHBA, CD209 and MAPK12 also indicating exit from the cell cycle. The regulation factors are examples and there are more i.e. the examples does not conclude limitations.

The invention also regards a method for producing phospholipid-free nanoparticles comprising the steps
a) providing a hydrophobic surface and/or or a hydrophilic surface in suspension of of liposomes, or any particulate cholesterol facing the OH group into an aqueous phase.
b) bringing the hydrophobic surface or the suspension of liposomes or any particulate cholesterol facing the OH group into an aqueous phase into contact with a solution of sterol, preferably cholesterol dissolved as monomers in an organic solvent or complexed with detergent;
c) removing the solvent or detergent forming a sterol membrane on the surface
d) providing a water solution of *quillaja* saponin micelles
e) adding the water solution comprising the saponin micelles to the sterol membrane, whereby a complex is formed between the saponines and the sterols and is suspended in the water solution.

The hydrophobic surface might be a surface in a jar, tub, several layer surfaces, beads, e.g. latex beads, nets or three dimensional nets or porous material. It might also be a liposome with the components integrated in the lipid membrane(s).

The liposome can be constructed according various techniques and with different compositions as described[14]. It might also be constructed as a virosome containing virus proteins integrated in the liposome membrane. The liposomes may be in a water solution. The devices may e.g. be packed in columns.

The saponins and sterols may be the ones mentioned above for the nanoparticles

The solvent may be any solvent as may be found on the site http://en.wikipedia.org/wiki/Organic solvents or detergent, preferably chloroform, ethanol or acetonirtril. The nature of the solvent is described in en.wikipedia.org/wiki/ organic solvents (Table 1). The selection of solvent is dependent on the nature of the molecule to dissolve. The different types of solvent are mainly classified according to polarity and non-polarity. Non-polar solvents are e.g. haxane, chlorform and diethyl ether. Those mentioned are useful because the can be avaporated having boiling points between 35 and 65 facilitating removal by evaporation. Polar aprotic solvents are often used for solubilisation of pharmaceutical molecules e.g. dimethyl sulfoxide, acetonitril. The latter is of interest because it has low boiling point. Polar protic solvents are also useful particularly in combination with other solvents. Ethanol, methanol have low boiling point and acetic acid has high boiling point. Low boiling point is particularly important for the evaporation technique. The solubilisation may be done with two or more solvents. The solvents mentioned are examples and there are many more having perhaps even more desired properties for the use in the innovation for forming G3 formulations. E.g. in example 14 DMSO has been used in combination with Chloroform.

Examples of usable are as non-ionic, ionic i.e. cationic or anionic or Zwitter-ionic detergent such as Zwittergent or detergent based on gallic acid which is used in excess. Typical examples of suitable non-ionic detergents are N-alkanoyl-N-alkyl-glucamines, polyglycol esters and polyglycol ethers with aliphatic or aralylphatic acids and alcohols. Examples of these are alkylpolyoxyethylene ethers with the general formula $C_nH_{2n+1}(OCH_2CH_2)x$ OH, shortened to Cn Ex; alkyl-phenyl polyoxyethylene ethers containing a phenyl ring between the alkyl group and the polyoxyethylene chain, abbreviated Cn phi.Ex, Triton X-100=tert$C_8E_96$ (octylphenolether of polyethylene oxide), acylpolyoxyethylene esters: acylpolyoxyethylene sorbitane esters, abbreviated Cn sorbitane Ex, e.g. Tween 20, Tween 80, .beta.-D-alkylglucosides, e.g. .beta.-D-octylglucoside. Typical examples of suitable ionic detergents are gallic acid detergents such as e.g. cholic acid, desoxycholate, cholate and CTAB (cetyl-triammonium bromide). Even conjugated detergents such as e.g. taurodeoxyoholate, glycodeoxycholate and glycocholate can be used. Other possible solubilizing agents are lysolecithin and synthetic lysophosphoilipids. Even mixtures of the above-mentioned detergents can be used. When using the dialysis method the detergents should be dialysable in not too long time.

Some surface active substances greatly facilitate matrix formation. These include the intrinsic biological membrane lipids with a polar head group and a non-polar aliphatic chain e.g. phosphatidyl choline (negatively charged) and phosphatidyl ethanolamine (positively charged).

According to one embodiment the detergent may be Triton-X-100, Tween-20, Nonidet, NP-40, deoxycholate, MEGA-10 and octylglycoside. MEGA-10 and octylglycoside can be removed by dialysis. For others other technologies can be used as mentioned e.g. the centrifugation method and column chromatography.

The soluble agent might be removed by evaporation using an organic solvent with low boiling point or by dialysis or by dialysis, chromatography, filtration or tangential flow as described in EPC-patent 0 109 942.

The water solution of saponin micelles is obtained by adding a freeze or spray dried powder as delivered from the producer. The saponin or saponin fraction is normally kept as stock solution e.g. 10 mg/ml water but not limited to that concentration and added to the water surrounding the lipid membrane at a final concentration above CMC i.e. critical micelle concentration e.g. 30 mg/liter exact figure is dependent on the *quillaja* product. The saponins are obtained as *Quillaja* Powder Extract and may be obtained from as crude *quillaja* extract (Berghausen, USA), *Quillaja* Ultra Powder QP UF 300, *Quillaja* Ultra Powder QP UF 1000 or Vax-Sap a non-fractionated *quillaja* saponn product, QHA and QHC fractions (all three from Natural Responses, Chile) or from Prodalysa, Santiago, Chile.

The invention is using a new production method wherein an artificial membrane of the sterol attached to a hydrophobic surface is produced in steps a-c). A water soluble micelle of a *quillaja* saponin product and a chemical (covalent) binding between the *quillaja* micelle and a component in the artificial membrane extracts the artificial membrane components into a water soluble complex as an innovative water soluble nanoparticulate complex i.e. G3. This complex is a held together by a chemical (covalent) linking keeping and binding the hydrophilic parts together in the water phase and hydrophobic interactions between components remains in the centre of the complex. The membrane is formed from an organic solution with a soluble agent that may be a detergent or an organic solvent.

The new process according to the invention starts with the creation of an artificial cholesterol membrane, which doesn't contain other molecules and is thus a very clean method. Cholesterol doesn't form natural membranes in cells. In nature a phospholipid or another lipid molecule is needed to form a membrane. In water e.g. liposome membranes also lipids are needed with larger hydrophilic moiety that is expanding into the water.

The inventors succeeded in creating a membrane of cholesterol only by anchoring the cholesterol molecules to a solid hydrophobic surface. That approach is facilitating the creation of a monolayer of cholesterol, orienting the OH group as an interphase directed into the aqueous phase facilitating and optimizing the interaction with the hydrophilic sugar moieties of the *quillaja* micelles.

Hydrophobic and amphipathic molecules to be incorporated into the artificial membrane, are solubilised with organic solvent or detergent together with the sterol in step b) and transferred to water phase by evaporation of the organic solvent. Dependent on the solvent it is removed by evaporation if the boiling point is below that of water or by dialyses or by similar techniques described for ISCOM formation. Thus, the removal of the solvent is not a part of the formation of the particle but for the formation of the artificial membrane that is not a part of the formation of the particles. Subsequent to the formation of the artificial membrane is completed there is water surrounding the artificial membrane. Into this water phase *quillaja* micelles suspended (dissolved) in water are added and the artificial membrane is extracted in the water phase and reorganization of the *quillaja* micelle to the new G3-formulation. The composition can readily be adjusted to completely dissolve the artificial membrane into a particulate suspension in water. The composition differs from a micelle from the construction point of view that a covalent linking is involved thus an innovative particle is formed.

In steps f) and g) the water soluble micelle form of the *quillaja* product is allowed to interact to get the final product into a water phase. The first interaction in this step is a covalent binding between the *quillaja* micelle and the sterol in the artificial membrane and the second interaction is between *quillaja* triterpenoid skeleton and the sterol. Under suitable proportions all components in the artificial membrane are incorporated into water soluble *quillaja* micelle forming a new nanoparticle that will vary in size from 17 nm up to 40 nm. A larger size is obtained if lipids e.g. a phospholipid are present in the artificial membrane. The examples 2, 4, 9, 14, 15 and 16 demonstrate that various kinds of lipophilic molecules have been incorporated according the invention including DT, busulfan, roscovitine, vivolux 40 and vitamine D3.

Iscom matrix may be produced with the new method by adding at least one phospholipide to the suspension comprising sterol in step b).

The phospholipide may be chosen from derivatives of glycerol phosphates such as derivatives of phosphatidic acids i.e. lecithin, cephalin, inositol phosphatides, spingosine derivatives with 14, 15, 16, 17, 18, 19 and 20 carbon atoms, phosphatidylethanolamine, phophatidylserine, phosphatidyl choline.

Hydrphobic components may incorporated in step b) i.e. in the artificial membrane that includes also lipids, sterols.

In step d) the saponin in the water soluble form i.e. micelle form is added to the water phase covering the artificial membrane The invented nanoparticle replaces the ISCOM matrix because it simpler and more economical to produce because the nanoparticle according to the invention is based on two components i.e. a *quillaja* saponin, cholesterol in contrast to the ISCOM particle formation includes three components i.e. a *quillaja* saponin, cholesterol and the third component a phospholipid e.g. phosphatidylcholine. The *quillaja* component(s) need not to be solubilized with detergent or with an organic solvent. The new production technique according to the invention is robust and the sensitive balance is overcome. Thus, the new method is more suitable than ISCOM matrix technologies for integration of a fourth, fifth or more i.e. other hydrophobic or amphipathic molecules since methods so far developed allow the strong tendency of such compounds to spontaneously form stable complexes (self-assembly) in water e.g. micelles and therefore not being integrated into the ISCOM matrix formulation e.g. by hydrophobic interaction. Thus, the ISCOM matrix technology has shortcomings to be developed as a general delivery system, but the invention does not have such shortcomings.

All publication mentioned herein are hereby incorporated as reference. The invention will now be described by the following non-limiting examples.

EXAMPLES

Materials and Methods

Chemicals and Compounds

Cholesterol (C8667), phosphatidylcholine (PC, P-5763), methanol (322415-1 L) and chloroform (288306) were all purchased from Sigma-Aldrich Sweden AB, Stockholm, Sweden. Fraction A (QHA) and Fraction C (QHC) of *Quaillaja* saponin are all purchased from ISCONOVA AB, Uppsala, Sweden. Diterpenoid (DT) i.e. *Stevia* was obtained from Prodalysa Ltda., Chile. Vitamin D3 was commercially obtained from Miva Nutri-molecular Research Limited, Shanghai, China.

QHC and Q-Sap (VaxSap) were purchased from Desert King international, CA, USA.

Isolute™ 1-g C18 (EC) solid-phase extraction (SPE) columns were purchased from International Sorbent Technology, Ltd., UK.

QS defined *Quillaja* saponin fractions prepared by Johan Bankefors at the Department of Chemistry, Swedish University of Agriculture Sciences, Uppsala, Sweden*

Cell Lines

The human macrophage (Mφ) cell line U937 (which is often used as a model cell line in biological and cancer research) and the human Acute Myeloid Leukemia (AML) cell lines HL-60 were grown in culture medium RPMI-1640. The human prostate adenocarcinoma, PC-3, cultured in a 50/50 mixture of HAM's F-12K and RPMI-1640. All the cells were kindly supplied by the division of clinical pharmacology, Uppsala University. All media were supplemented with 10% heat-inactivated fetal calf serum (FCS), 2 mM glutamine, 100 µg/ml streptomycin and 100 IE/ml penicillin (all from Sigma Aldrich Co, St Louis, Mo., USA). All cell lines were incubated at 37° C. in humidified air containing 5% $CO_2$.

Human Dendritic Cells (DC's)

Immature human DCs were purchased from 3H Biomedical, Uppsala, Sweden.

G3 Formulation

Dissolve VaxSap and cholesterol in Chloroform in concentration of 100 mg/ml. For formulating G3 particles with molar ratio of QS:Cholesterol 1:1, take 100 µl chloroform into an Eppendorf tube. Add 2 µl cholesterol and 500 µl $H_2O$ to the tube. Evaporate chloroform in the tube by injecting air with syringe and needle. A membrane of cholesterol will be visible on the inside wall of the tube. Discard the water and replace it with 1 ml PBS, pH 5.9-6. Add 10 µl VaxSap/QHC into the tube with PBS. Sonicate 1 hour at 37° C. and incubate overnight at 37° C. The theoretical final concentration will be 1 mg/ml of QS and 200 µg/ml of Cholesterol.

Ultra sonic method: was used to speed up the molecular movement to facilitate the hits between the cholesterol in the artificial membrane.

G3-D3 Formulation

Dissolve VaxSap, cholesterol and D3 in Chloroform in concentration of 100 mg/ml. For formulating G3-D3 particles with molar ratio of QS:Cholesterol:D3 1:0.5:0.5 take 100 µl chloroform into an Eppendorf tube. Add 1 µl cholesterol, 1 µl D3 and 500 µl $H_2O$ to the tube. Evaporate chloroform in the tube by injecting air with syringe and needle. A membrane of cholesterol-D3 will be visible on the inside wall of the tube. Replace the $H_2O$ with 1 ml PBS, PH 5.9-6. Add 10 µl VaxSap into the water. Sonicate 1 hour at 37° C. and incubate overnight at 37° C. The theoretical final concentration will be 1 mg/ml of QS. 100 µg/ml of Cholesterol and 100 µg/ml of D3.

Reduction of Aldehyde Group in Position C-23 on the Triterpen Skeleton of the *Quillaja* Molecule 5 mg of QH-C was dissolved in 10 mL ethanol (0.5 mg/mL) and added drop wise to a stirred suspension of sodium borohydride in ethanol (1 mg/mL, total volume of 5 mL). The reaction is stirred at room temperature for 4 h. Then the mixture was made acidic by the addition of 0.1M HCl and 100 mL water was added to the solution which was then applied to a SPE column. The saponins were first washed with aq 10% methanol (v/v) and then compounds were eluted with methanol and evaporated to dryness. The removal of the aldehyde group was confirmed by $^1$H-NMR, where the aldehyde signal at 9.46 ppm not could be detected after the reaction.

The read out was the particle formulation i.e. the extraction of the membrane into the *quillaja* micell, the anticancer cell killing effect tested on U937 cancer cells and the stimulation of IL-8 of the same cells (see Materials and Methods).

NMR was carried out at department of chemistry Swedish Agriculture University.

Oxidation of Sugar Molecules on Saponin

The oxidation with periodate was carried at the Department of Chemistry, Swedish University of Agriculture Sciences, Uppsala, Sweden: Basically the QHC fraction of *quillaja* saponin was treated with the concentrations 2.5 to 50 mM of sodium periodate in 50 mM sodium acetate buffer, pH 4.5 at time points from 1 hour up to 4.5 hours (see Example 20) hour in the dark at 4° C. The oxidation was stopped by adding ethylene glycol. The reagents were removed by dialyzes against $H_2O$ and kept lyophilized until used. The oxidized material were then dissolved in water at a concentration of 10 mg/ml and used in cells to measure biological activities (SI and IL-8 production).

Blocking G3 Formulation by Sugars

For formulating G3 particles with molar ratio of QS:Cholesterol 1:1, take 100 µl chloroform into an Eppendorf tube. Add 2 µl cholesterol and 500 µl $H_2O$ to the tube. Evaporate chloroform in the tube by injecting air with syringe and needle. A membrane of cholesterol will be visible on the inside wall of the tube. Discard the water and replace it with 1 ml PBS, pH 5.9-6. Add the sugar to tubes with Cholesterol membrane and incubate 1 hour at 37° C. Add 10 µl VaxSap/QHC into the tube. Perform Sonication 1 hour at 37° C. and incubate overnight at 37° C. The theoretical final concentration will be 1 mg/ml of QS but the Cholesterol concentration will differ depending on the blockage by sugar.

Measurement of Cell Metabolic Activity

The Alamar Blue assay was used essentially according recommendations from the supplier (Serotec Ltd, Oxford, UK). Briefly, the cells were adjusted to $1\times10^5$ cells/ml in cell culture medium and 200 µl/well cells in 96-well plates (Nunc, Roskilde, Denmark). Then various QS formulations or medium alone (as control) was added in triplicates and incubated 3 days at 37° C. in humidified atmosphere containing 5% $CO_2$. Alamar Blue was added to a final concentration of 10% to the wells after specified time points. The cell metabolic activity was subsequently measured up to 8 hrs. The OD values were read at 570 and 600 nm in a spectrophotometer (Labsystems Multiskan RC, type 351). Metabolic activity is expressed as percent of the cell control (survival index; SI) and IC50s were defined as the concentrations of the G3 formulations resulting in 50% metabolic inhibition compared to control.

Cholesterol Measurement

The Total Cholesterol Quantitation Kit (Abeam, ab65359) provides a simple method for sensitive quantification of free cholesterol, cholesteryl esters, or both. Cholesterol is then oxidized by cholesterol oxasetoyiel H□O□ that reacts with a sensitive cholesterol probe to produce color ($\lambda$max=570 m). The Cholesterol has been measured by adding the reactions mix contains Cholesterol buffer, probe, esterase and enzyme mix to the samples and then incubated the mixture in 37 C. for one hour followed the measurement I 96 well plate at 570 nm. For more information about the KIT: (www.abcam.com/ps/products/65/ab65359).

Transmission Electron Microscopy TEM Analysis

The G3 samples were loaded on Copper grid and dried for a few minutes. Then the samples were washed 3 times with MQ-H2O to take away the salts residues from PBS. The samples were then stained with saturated uranyl acetate in distilled water and left for 5 minutes then the micrographs were taken at 80 kV accelerating voltage.

In Vitro Assay Procedure

Cells in 96-well micro-titer plates at a cell density of 5,000-20,000 cells/well were exposed to serial diluted G3, KGI and *Quillaja* saponin products containing the same amounts of QHC at 37 C. in humidified atmosphere containing 5% CO2 for 72 hours. For U937 cells, one set of, the cells were used directly for the fluorometric microculture cytotoxicity assay (FMCA) to measure cell killing effect of the formulations. For the other set of the cells, the supernatant was collected 150 µl/well for cytokine IL-8 determination.

Measurement of Cancer Cell Killing Effect

The FMCA method is based on measurement of fluorescence generated from hydrolysis of fluorescein diacetate (FDA) to fluorescein by cells with intact plasma membranes. After above mentioned incubation for 3 days, the medium was removed by aspiration. After one wash with PBS, 100 µl/well of FDA dissolved in a physiological buffer (10

μg/ml) was added. The plates were incubated for 45 minutes and the generated fluorescence from each well was measured in a 96-well scanning fluorometer. The fluorescence is proportional to the number of intact cells in the well. Quality criteria for a successful analysis included a fluorescence signal in the control wells of more than five times of the mean blank value, a mean co-efficient of variation (CV) in the control wells of less than 30%.

Cytokine IL-8 Determination for U937 Cells Stimulated with G3 Formulations

ELISA for the detection of human IL-8 was carried out according to the manufacturer's instruction (Human IL-8 ELISA, catalogue No. S8000C, R&D system, Minneapolis, Minn. 55413, USA). Briefly, 50 μl reconstituted standards of human IL-8 and the supernatants were added to each well in triplicate wells and mixed well by gently tapping the plates several times. The plates were then covered with adhesive plate covers and incubated for one hour at room temperature (RT, 20-25° C.). After the incubation, the plates were washed 3 times with Wash Buffer and 50 μl/well of the Biotinylated Antibody Reagent (anti-human IL-8) was added. The plates were covered again with adhesive plate covers and incubated for one hour at RT. After being washed 3 times with Wash Buffer, 100 μl/well of Streptavidin-HRP Solution was applied. The plates were covered with the adhesive plate covers again and incubated for 30 minutes at RT. The contents in the plates were discarded and the plates were washed 3 times with Wash Buffer. 100 μl of TMB Substrate Solution was dispensed into each well. The enzymatic colour reaction was allowed to develop at RT in the dark for 30 minutes. The reaction was stopped by adding 100 μl/well of Stop Solution. The absorbance was read on an ELISA plate reader at 450 nm and 550 nm. Subtract 550 nm from 450 nm values to correct for optical imperfections in the micro plates. The standard curve was then generated and used to calculate the amount of human IL-8 in the unknown samples. The standard curve was created by plotting the average absorbance obtained for each standard concentration on the vertical (Y) axis vs. the corresponding concentration (pg/ml) on the horizontal (X) axis.

Cytokine IL-12 Gene Expression of Human Monocytes Stimulated by G3 Formulation

The cytokine IL-12 gene expression of treated DCs by G3, DT, G3 with DT incorporated were compared with the cell control by gene arrays. Briefly, normal human monocytes were exposed to 10 μg/ml of G3, 100 μg/ml of DT and the combination of these two in the same particles with the same concentrations for 6 hours, then RNA was isolated according to the manufactures manual (QIAGEN RNeasy Minikit). RNA expression analysis was done at "Uppsala Array Platform. Clinical Chemistry and Pharmacology, Uppsala University Hospital Uppsala-Sweden" by converting the RNA samples to labelled eDNA via reverse transcription and comparing the quantitative data from the various samples with untreated cells (Ambion WT Expression Kit).

Thymidine Kinase (TK) Activity

The TK activity was determined with a kit obtained from Biovica (Uppsala, Sweden). Briefly, after exposing to KGI or G3 formulations at various time points, 100 μl cell suspension at a concentration of $0.1-1 \times 10^6$ cells/ml was transferred to Eppendorf tubes and centrifuged at 200 g for 10 minutes. The cell pellet was re-suspended in 100 μl cold PBS and freeze/thawed 2-3 times. After centrifugation at maximum speed for five minutes, then the cells were collected. The inter-cellular TK activity was measured according to the manufacturer's protocol.

Detection of Vitamin D3

Samples with cholecalciferol (vitamin D3) incorporated in G3 particles were analysed at a University Hospital Laboratory on a Liaison automatic instrument. Although the assay (DiaSorin Liaison) is designed to measure 25-HO-D3 it has about one percent cross-reactivity with non-hydroxylated vitamin D3.

Influenza Virus Strains and Vaccine

The human influenza virus A/California/07/2009 (H1N1), A Perth/16/2009 (H3N2) and B/Brisbane/60/2008(B) as a non-adjuvanted vaccine was used as antigen in the preparation of the vaccines, the serological tests and in the re-stimulation of lymphocytes. The virus was cultured on VERO cells and split with deoxycolate. It was kindly supplied by the manufacturer. After harvest, the viruses were purified, inactivated, split and re-suspended at a concentration of 30 μg protein/ml. The dose contained 1 μg virus antigen and various amount of adjuvant as indicated in FIG. 1.

Vaccination

C56Bl6 mice hosted at the animal facility, University Hospital, Karolinska Institute, Stockholm, were immunized subcutaneously in the neck twice. For details, see example 12.

Haemagglutination (HA) Test

Chicken erythrocytes (RBCs) collected in citrate solution were washed 3 times using 0.01M phosphate buffered saline (PBS) pH 7.2 and re-suspended at a concentration of 0.5% in PBS containing 0.05% bovine serum albumin (BSA). The HA test was performed in U-type microplates at 4° C. for 1 hour.

Haemagglutination Inhibition (HI) Test

Serum samples were incubated at rum temperature (RT°) together with a 30% suspension of chicken RBCs for 1 hour (h). After absorption, the mixtures were centrifuged at 500×g for 10 min and the supernatants collected. The final serum dilution was 1:5. The HI test was carried out using V-type microplates and 16 HA-units/50 μl. Serum samples, 25 μl were 2 folds diluted using an equal amount of PBS—BSA. The diluted sera were incubated at RT° for 1 h together with 25 μl of virus suspension after which the mixtures were incubated at 4° C. for 1 h. The highest serum dilution inhibiting 100% the Haemagglutination was considered as the antibody titer for the sample.

Preparation of Lymphocytes

The spleen-lymphocytes (splenocytes) were obtained as aseptically as possible. Immunized and non-immunized mice were bled and sacrificed by cervical dislocation at 3 weeks post revaccination. Spleens were removed and thereafter carefully teased, passed through a sterile stainless steel mesh and flushed with EMEM with Tricine using a pipette. The cells were washed twice using EMEM with Tricine means centrifugation at 500×g with. Then, the pellets were re-suspended in F-DMEM medium supplemented with 1% fetal calf serum (FCS), 10 μg gentamicin/ml, 2 mMl L-glutamine, 3.81 g Hepes/L and $5 \times 10^{-5}$M β-mercaptoethanol (culture medium). The cells viability was assayed by Trypan blue dye exclusion test.

Enzyme-Linked Immunospot Assay (ELISPOT)

The enumeration of cytokine secreting splenocytes was carried out using commercial ELISPOT-kits for INF-γ, IL-2 or IL-4. The kits were purchased from Mabtech, Stockholm, Sweden. The ELISPOT plates were used following the instructions recommended by Mabtech.

For each cytokine, splenocytes at a concentration of $2 \times 10^5$ per 100 μl culture medium were pipette into 8 different wells. Four replicates received 50 μl culture medium containing 4.5 μg haemagglutinin of influenza virus antigen. The resting four wells received 100 μl of culture medium only. Plates were incubated at 37° C. in humidified boxes for 18 h after which the cells were discarded and the wells washed. Spots were developed following the procedure described by Mabtech. In short, plates were incubated for 2 h at RT° with 100 μl biotinylated monoclonal antibodies (MoAb) anti IFN-γ, IL-2 or IL-4. Then, the plates were carefully rinsed and thereafter incubated for 1 h at RT° with HRPO conjugated Strepavidin. After another wash cycle, the plates were incubated with the substrate at RT° for approximately 15 min or until distinct spot emerged. Washing the plates with tap water stopped the reactions. Finally, the plates were allowed to dry and thereafter the number of spots was counted using an ELISPOT counter.

Data analysis and statistics.

Dose-response data were analyzed using calculated SI values and the software program GraphPadPrism4 (Graph-Pad Software Inc., San Diego, Calif., USA). Data are presented as mean values±SE. Statistical inferences between several means were performed by one-way ANOVA with Tukey's multiple comparison post test of group means and for comparison of two means, by Student's t-test, in Graph-PadPrism.

Part I. Formulation and Characterization

Example 1

Experiment 1A

Formation of G3 Particles

The basic structure of the G3 particle is a two component structure. The formulation i.e. the production of the particle is based on a step wise procedure. In the first step all hydrophobic and amphipathic components are assembled to be included in the final G3 particle. The second step encompasses extraction of the lipophilic components in the lipid membrane to be incorporated into the water soluble *quillaja* particle (suspension) i.e. an innovative manner and new concept for formulation of a colloidal particle, the G3 particle. The crucial event is a binding in the water phase between the aldehyde group (HO) on the triterpen of *quillaja* molecule is destroyed no binding occurs determined by failure of G3 formation and also on the effect to kill cancer cells or stimulate cells to produce cytokines in this case measured by IL-8 production (see example QQ).

In this example, the formulation of the G3 nanoparticles is described. In experimental set up step 2, A and B, (see below) the influence of the proportions of cholesterol vs QHC fraction (from ISCONOVA AB, Uppsala, Sweden, see WO2008/063129) of *Quillaja* saponin has been explored. In C the effect of adding a phospholipid is explored with regard to particle formulation.

Experimental Set-Up

In step 1 an artificial cholesterol membrane is formed requiring a solubilisation in detergent or organic solvent. In this experiment we have used chloroform (288306, Sigma-Aldrich Sweden AB, Stockholm, Sweden) as the solvent for cholesterol (C8667, Sigma-Aldrich Sweden AB, Stockholm, Sweden) to generate a stock solution of 100 mg of cholesterol/ml. In an Eppendorf tube, 2 μl of cholesterol from the stock solution diluted in 50 μl chloroform was added, subsequently ½ ml of water was layered on the top of the cholesterol solution. The chloroform was evaporated by a stream of air created with a syringe with a needle. A visible layer of cholesterol was seen on the wall of the tube. The cholesterol membrane was also formulated to contain phosphatidyl choline (P-5763 is from Sigma-Aldrich Sweden AB, Stockholm, Sweden) (PC) in a ratio of 1 mole cholesterol and 1 mole PC.

Alternative ways to create the artificial membrane are the use of any kind of hydrophobic surface e.g. beads where latex beads is one example, hydrophobic nets, filters etc attaching the hydrophobic components intended to be incorporate into the G3 particle.

In Step 2

The ½ ml of water was replaced by 1 ml of fresh water containing 10 μl of the QHC stock solution (100 mg/ml in water), followed by incubation over night at 37° C. The membrane disappeared from the wall and a clear water solution is seen. Three formulations i.e. A, B and C were prepared:

Formulations
  A. Two μl of cholesterol stock solution and processed as described step 1 and 10 μl of the QHC in step 2 were used to generate this G3 formulation, which gave a molar ratio of 1:1
  B. Another molar ratio was also used i.e. 2 mole of cholesterol vs. 1 mole of QHC. Otherwise, the experiment was the same as for A
  C. A ratio of 1 mole cholesterol and 1 mole phosphatidylcholine were used to form the membrane in step 1. In step 2, two mole of QHC was used.

Results

A. After evaporation, a 17 nm particle having a uniform size was achieved characterized by electron microscopy (EM) see FIG. 1A and by gradient centrifugation. The G3 suspension is visualized as a clear solution.

B. After evaporation, particles of a slightly wider size range were observed in EM with a medium diameter of about 17 nm (not shown), i.e. 17 nm particles were also created with the ratio of 2 mole of cholesterol and 1 mole of *Quillaja* saponin.

C. The product had morphology like that of ISCOM particles with a diameter of about 40 nm (FIG. 1B) Thus, the morphology is completely different with the inclusion of phosphatidylcholine from that of the nanoparticles according to the G3 invention without the phosphatidylcholine. It can also be concluded that the nanoparticles according to the invention is an excellent basis for integration of phospholipids including phosphatidylcholine being essential for ISCOM formulation as claimed by Lövgren & Morein[2].

Conclusion and Discussion

The molar ratio of 1 cholesterol/1 *Quillaja* molecule form small (17 nm) nano-particles. The higher ratio of cholesterol i.e. molar ratio of 2 cholesterol vs 1 *Quillaja* or more, then larger particles appear. To note, by inclusion of other lipophilic components in step 1, the size of the particle will vary, i.e. the loading of the particle influences the size. In this case, the range of size was recorded between 17 and 40 nm, but that is not the limitation of the range. Especially important is that in EM no aggregation of the particles was seen rather the particles were well dispersed from each other. The recovery rate of QHC in these G3 formulations was all 100%. Alternative ways to create the artificial membrane are the use of any kind of hydrophobic surface e.g. beads where latex beads is one example, hydrophobic nets, filters etc. attaching the hydrophobic components intended to incorporate into the G3 particle.

An essential and new concept to render lipophilic substances water soluble is created with this two-step procedure. There are various ways of forming lipid membrane e.g. liposomes that have no solid hydrophobic support, but are in free suspension in a water phase. The second step extracts the membrane into the water phase regardless of how the membrane is anchored to a surface or not anchored as a liposome in a water phase. In all these cases the membrane is extracted into the water soluble G3 particle. The crucial part is the binding in the water phase between the aldehyde group and the only water accessible OH-group of cholesterol.

After destruction of the aldehyde group of the *Quillaja* (QHC) in the water phase (see Ex 1 B) no G3 particles are formed and the created membrane according to Step 1 is not extracted from the wall and the water phase. Moreover, the biological functions such as anticancer cell killing and the stimulation of IL-8 are abolished.

To note, the procedure for forming nano-particles according to the invention is robust and much simpler than now used methods e.g. to make ISCOM formulations (Lövgren & Morein, see above). Above all, with the evaporation method there is hardly any loss of material used for the particle formulation i.e. *Quillaja* saponin in the referred case QHC and cholesterol. Moreover, no phospholipid is required, further reducing the production costs. Interestingly, the nanoparticles according to the invention can be used as a base for forming ISCOMs. It can also be concluded from this example that an ISCOM requires a phospholipid to obtain the morphology that characterized the ISCOM particle.

If detergent is used for solubilisation the removal of solubilizing agent e.g. the detergent has to be done as described by Lövgren & Morein[2] e.g. by dialyses, column chromatography, ultracentrifugation or tangential flow. Using such methods it may be more practical to use beads (e.g. latex beads) with a hydrophobic surface. Thus, the two step procedure is an innovative robust method to formulating nanoparticles.

Amphipathic molecules form micelle particles in water above the critical micellar concentration (CMC). Below CMC the micelle disintegrates. By injection into an individual the concentration decreases and the micelle disintegrates and cannot be seen by EM resulting in poor bioavailability of the components in the micelle. By forming e.g. *Quillaja* saponin into G3 particles this phenomena is abolished.

Moreover, this method that in step 1 formulates a membrane is a general method for incorporating lipophilic molecules into the water soluble G3 particle in step 2.

Experiment 1B

Materials

The methanol (LiChrosolvl) was obtained from Sigma-Aldrich (Seelze, Germany). The water was produced in-house in a Milli-Q system (Millipore Corp., Molsheim, France). Isolute™ 1-g C18 (EC) solid-phase extraction (SPE) columns were purchased from International Sorbent Technology, Ltd., UK.

In example 1 experiment A It is shown that *quillaja* micelles in the water phase interact with cholesterol in the artificial membrane created in experiment A. The only polar group on cholesterol is a hydroxyl group that can react with the *quillaja* molecule in a water solution. This experiment explores whether the aldehyde is involved in particle formation and the biological activities cancer cell killing and IL8 production. The aldehyde group in position C-23 on the triterpen skeleton of the *quillaja* molecule was destroyed by reduction and analysed. The read out was the particle formulation i.e. the extraction of the membrane into the *quillaja* micelle, the anticancer cell killing effect tested on U937 cancer cells and the stimulation of IL-8 production of the same cells (see Materials and Methods).

Five mg of QH-C was dissolved in 10 mL ethanol (0.5 mg/mL) and added drop wise to a stirred suspension of sodium borohydride in ethanol (1 mg/mL, total volume of 5 mL). The reaction is stirred at room temperature for 4 h. Then the mixture was made acidic by the addition of 0.1M HCl and 100 mL water was added to the solution, which were then applied to a SPE column. The saponin was first washed with 10% methanol in water (v/v) and then compounds were eluted with methanol and evaporated to dryness. The removal of the aldehyde group was confirmed by $^1$H-NMR, where the aldehyde signal at 9.46 ppm could not be detected after the reaction.

Results

The visible artificial membrane as described in Experiment A (Example 1) was not affected by the addition of QHC in the water phase as described in example A i.e. the membrane was still visible (not shown). The anticancer cell effect was totally abolished (FIG. 1C) and the IL-8 production was also totally abolished (not shown).

Discussion and Conclusion

To show the interaction between cholesterol membrane and *quillaja* an artificial membrane has to be formed in this case anchored on a hydrophobic surface where the membrane is visualized. The only polar group on cholesterol is a hydroxyl group phasing into the water phase. The hypothesis was that the aldehyde group in the triterpen would be reactive and it was therefore destroyed by reduction as described in Materials and Methods. The *quillaja* (QHC) molecule with reduced aldehyde did not extract and integrate the membrane into forming a G3 particle with the QHC molecule. QHC in its original form kills cancer cells (Fig x) and stimulate IL-8 production but these effects were abolished after reduction of the aldehyde group. Thus, it is convincingly shown that the aldehyde group is responsible for binding to the only water accessible group i.e. the OH group on cholesterol. A second binding is by the hydrophobic interaction between the sterol and the *quillaja* terpen. That is proven by the fact that other molecules in the artificial membrane such as, phophatidyl choline (Ex 1), Diterpen (Ex 2), the anti-cancer drug VLX 40 (ex 14), the anticancer drug Roscovitine (Ex 15 and the vitamin D3 (ex 16) became integrated into the G3 particle. These molecules must therefore, directly or indirectly be bound by hydrophobic forces cholesterol and subsequently to the *quillaja* molecule forming G3.

The two bonds i.e. the hydrophobic and the hydrophilic bindings render a stable particle that is not dissolved by CMC or by methanol or by ethanol (not shown). In contrast the *quillaja* including QHC are disintegrated by a CMC as 3 mg/liter and they are soluble in methanol and ethanol.

Example 2

This example shows that a molecule with amphipathic properties can be incorporated into the G3 particles according to the technology described in Example 1. To note DT is naturally soluble in water as a micelle being disintegrated after administration due to dilution to below CMC at the site of injection and subsequently after the transportation from the site. It has, therefore, poor bioavailability. Consequently a stable complex in G3 is important.

Experimental Set-Up

The experiment set-up is essentially the same as for Example 1, apart from that an amphipathic molecule diterpenoid (DT) was also solubilized at the same time with cholesterol in chloroform and the artificial membrane was formed with DT as described for Example 1. The DT molecule together cholesterol was extracted and integrated with Quil A fraction C (QHC) to forming the G3 particle in step 2 as described in example 1 i.e. 1 µl DT (100 µg/ml in 99% ethanol as the stock solution) was solubilized in chloroform at a molar ratio of 1 cholesterol:0.5 DT described for step 1 in example 1. In step 2, molar ratio of QHC in the water phase to cholesterol in the lipid membrane was 1 to 1 and the G3 formulation was completed as described in example 1.

Results

The G3 particle with incorporated DT has the same morphology as the G3 particle without DT depicted in FIG. 1A. In step 1 a membrane was visualized on the walls of the tube that disappeared in step 2. The water solution from step 2 is clear to slightly opalescent and no sediment was detected.

Conclusion

The amphipathic molecule diterpenoid (DT) in the micelle form was successfully dissolved with cholesterol in chloroform and a membrane was formed as described in Ex 1 step 1. In step 2 this membrane was integrated into the G3 nanoparticles according to the invention, resulting in typical G3 nanoparticles of 17 nm. Thus, the capacity to use the G3 nanoparticles according to the invention as a carrier/delivery system for an amphipathic molecule is shown. Amphipathic molecules with required configuration form micelles that mostly are instable after administration into individuals because the CMC is too high to keep the micelle formation resulting in disintegration and low bioavailability. In examples 4 and, it is shown that this G3-DT particle is biology active. Further studies will be performed during the Paris Convention priority year to further prove the immune enhancing capacity and usefulness of the nanoparticles according to the invention as delivery particles and for enhancing biological effects by interaction with cells e.g. via binding in the aqueous phase to the cells membranes. For more information see Hu et al[3], incorporated herein by reference. By incorporation of other molecules with complementary properties including the immune enhancing and the cancer cell killing effects will potentially be substantially broadened.

Example 3

The capacity of G3 to kill cancer cells were tested in vitro on the U937 model representing a lymphoid tumour cell.

Experimental Set-Up

G3 particles were formulated with various weight or molar ratios between cholesterol and QHC as described in Materials and Methods. The various formulations were incubated and the cancer cell killing effect was measured after staining and reading by the FMCA method as described in Materials and Methods.

Result's

G3 particles formed with the ratio of 1 cholesterol vs 5 QHC according to the weight i.e. 1 cholesterol vs 1 QHC according to the molarity, as described in Ex 1 and concluded from morphology according to the EM results (see Ex1 and FIG. 1A.). The cancer cell killing effect and IL-8 inducing capacities measured on U937 by the G3 particle was of the same magnitude as that of the KGI particle (FIG. 2 and FIG. 3), indicating that the active component QHC was preserved when incorporated in the G3 formulation.

Discussion and Conclusion

The cancer cell killing effect according to the invention is as potent as that of KGI. In fact the production method of the invention is very mild to the *quillaja* component since those are not is exposed to any solvent except the original water phase. The production method of G3 is from that point fundamentally different from that of KGI where the *quillaja* component has been exposed to the solvent e.g. detergent. KGI with the same active groups has previously been known to kill U937 cancer cells (PCT/SE 2007/050878).

Example 4

This example shows that the amphipathic molecule DT can be incorporated into the G3 particles according to technology as described in Examples 1 and 2.

DT is a diterpen, a stevioside produced from *Stevia rebaudiana* bertoni[15]. We have used DT because it has a number of interesting medical including immunological properties as published[16]. One problem with this compound is that it has low bioavailability in vivo as we have experienced requiring a stable delivery system e.g. in a nanoparticle.

The capacity of DT to induce the cancer cell U937 to produce IL-8 was done to explore immunological effect but even more importantly to demonstrate with this cytokine that DT may lead the cancer to differentiation being important to ceasing the uncontrolled cancer cell proliferation. Furthermore, the capacity of DT to induce human dendritic cells (DC) cytokines including IL-12 was tested. These tests were carried out to emphasize that DT has an important complementary immunological effect to Quil A and it is, therefore, useful to be incorporated in the G3 particles. DT was supplied by Prodalysa LTDA, Santiago, Chile. Here we used DC prepared as described in Material and Methods.

Experimental Set-Up

The U937 cells were incubated with KGI or G3 formulations starting from 100 µg/ml followed by 5-fold dilutions for 6 steps for 48 hours at 37° C. Then, the supernatant was collected and used for IL-8 detection as described in Materials and Methods For the measurement of gene expression, human DCs were incubated with BBE, KGI, DT (a formulation originating from *Stevia*) and DT in combinations with BBE or KGI (FIG. 4A) as well as G3 with or without *Stevia* incorporated (FIG. 4B) for 6 hours. The expression of various cytokine genes from the treated DCs was carried out by mRNA array analysis as described in Materials and Methods.

Results

Figure 3:
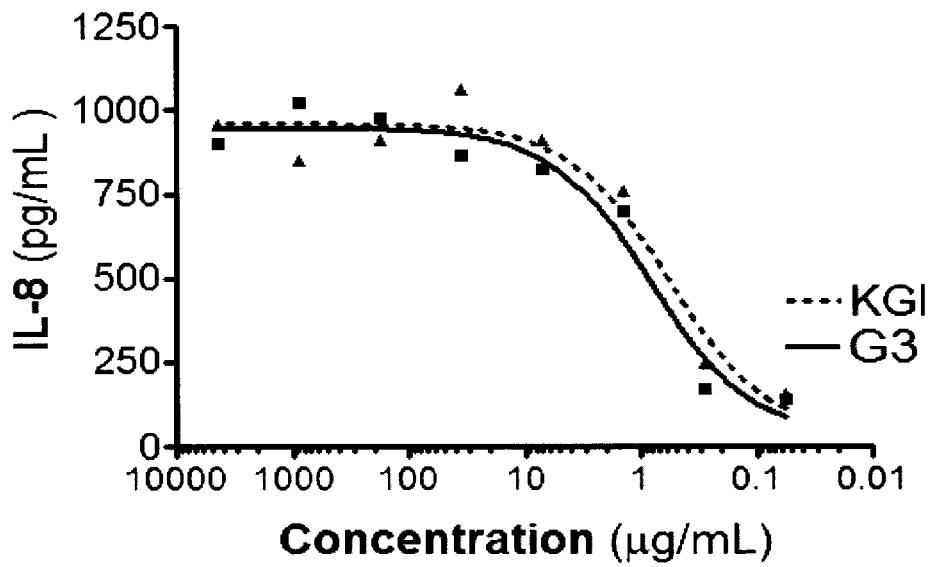
FIG. 3. Comparison of by G3 and KGI to induce U937 tumour cells to produce IL-8 showing that both particles have similar capacity to induce cytokine production in cancer cells indicating differentiation (P>0.05).

G3 particles induced U937 cancer cells to produce a similar level of IL-8 production to that induced by KGI (FIG. 3). IL-8 is a differentiation marker of the cancer cell.

Figure 4A:
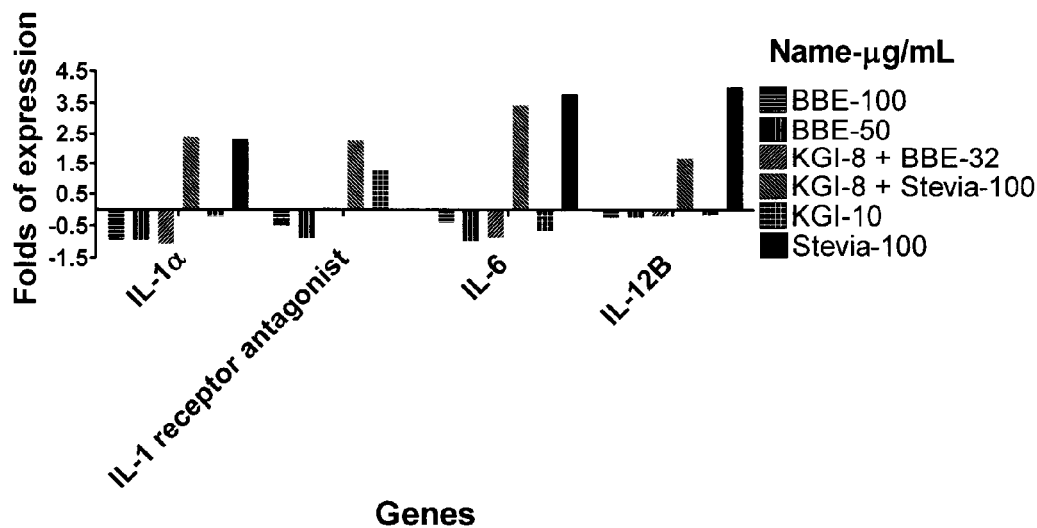
FIG. 4A. DT induced high levels of IL-12, IL1β and IL-6 expression than those induced by the ISCOM like formulations such as KGI, BBE and KGI+BBE.
Figure 4B:
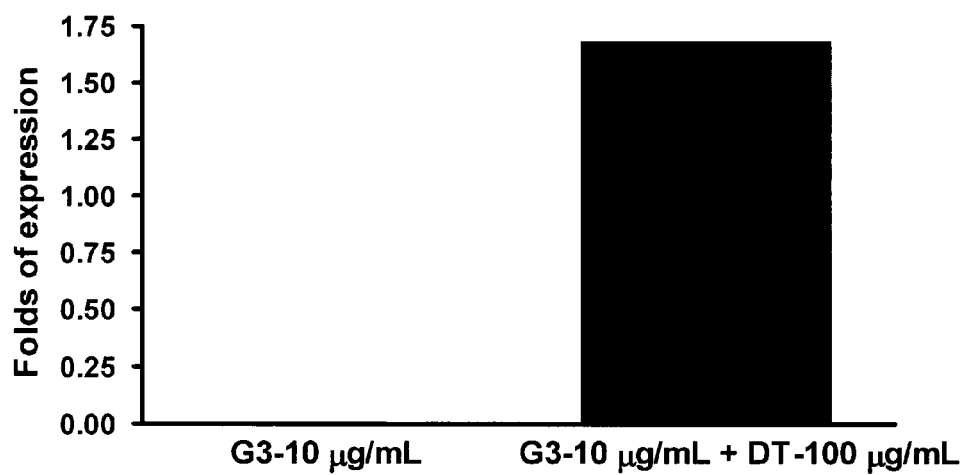
FIG. 4B. DT, when incorporated into G3, up-regulate cytokine IL-12 gene expression of normal human DCs.

FIG. 4A shows that DT induced high levels of IL-12, IL1β and IL-6, higher than those induced by the ISCOM like formulations KGI and BBE The G3 particles with DT incorporated induced high level of IL-12, while the G3 formulation without DT incorporated did not induce detectable level of IL-12 (FIG. 4B).

Discussion and Conclusion

DT has complementary properties to G3. The capacity to induce the U937 cancer cells to produce IL-8 indicates immune enhancement. More importantly, G3 standalone can differentiate and lead the cancer cell to cease proliferation like KGI as we have shown (manuscript in preparation to be supplemented). Complementary effect to the G3 alone is the notion that DT potently induces IL-12 being important for induction of a Th1 type of immune response including the production of IFN-γ, which also has anticancer effect for certain tumours. From immunological point of view. IL-12 is important for rejection of tumours if there are tumour antigens recognized by the immune system. IL-12 is also important for the immune defense against virus infections. It is of particular interest to note that DT, when incorporated into G3 that is serving as a carrier/delivery particle preserves the stability of DT in a potent and increased bioavailable form after administration. To note, DT stand alone is in a micelle form in water that disintegrate after administered into the body of an individual because the dilution at the site of administration and subsequently hampered transportation from that site. The G3 particle is held together by other forces and does not disintegrate e.g. after injection that has been recorded by EM studies (not published). This example emphasizes that the G3 invention serves as carrier for amphipathic molecules.

Part II. G3 as an Anticancer Drug

Example 5

Inhibition of thymidine kinase (TK) activity by G3 particles is an essential property to prevent uncontrolled replication of cancer cells and for the subsequent steps to steer the cell to a programmed cell death i.e. apoptosis. Moreover, cease of replication is essential for differentiation important both for adjuvant activity of vaccines and for ceasing malign disorders due to uncontrolled cell replication.

To explore one mechanism of G3 particle to inhibiting the cancer cell replication was evaluated by measuring the inhibition of TK enzymatic activity on U937 cells. Using inhibition of the TK enzyme activity for showing inhibition of cancer cell replication can also be used as a diagnostic tool to evaluate whether the G3 particles will be useful for therapy by analysing samples from patients to be treated with drugs containing G3 i.e. personalized diagnostic.

Experimental Lay-Out

U937 cells were exposed to the same amounts of active substance in G3 or KGI. At various time points, the treated cells were collected and intra-cellular TK activities were measured as described in Materials and Methods.

Results

Figure 5:
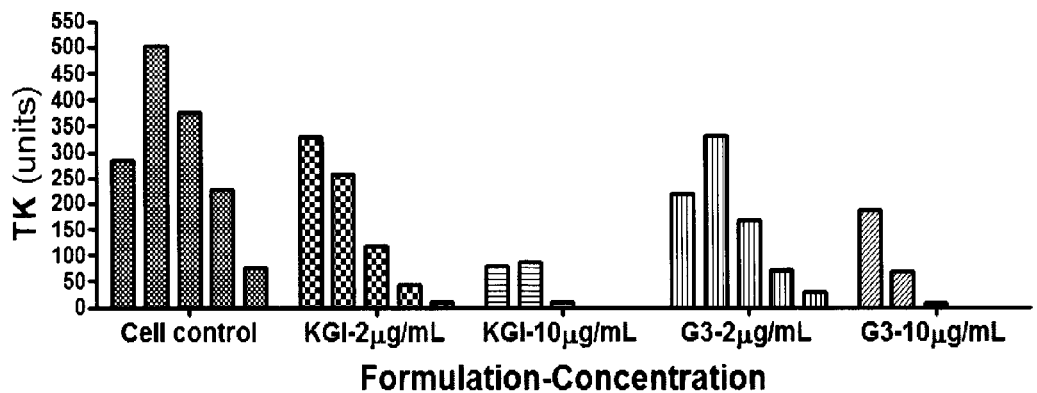
FIG. 5. G3 particles influence intra-cellular TK production of U937 cells at a similar magnitude to that of KGI particles (the bars in each formulation-concentration combination indicates time points of 24, 48, 72, 96 and 120 hours from the left to the right).

G3 particles inhibit virtually the same magnitude of intra-cellular TK activities as that of KGI (FIG. 5).

Conclusion

The inhibition of the TK activity causes the cancer cell to ceasing the replication being essential for DNA duplication. The inhibition of TK activity on the cellular level can therefore be used to measure the sensitivity of cancer cell from the patients to the drug, i.e. the G3 particles, paving the way to personalized medicine. To our knowledge, TK activity has been used as a non-specific test for the detection of increased serum TK in cancer patients. By applying it directly on cancer cells from patients to be treated the decision can be made whether to use G3 for the treatment.

Example 6

This example shows G3 and G3 with DT (G3-DT) kills the non-solid tumour human Acute Myeloid Leukemia (AML) cells more efficiently than the active component QHC (QHC) in G3 in a non-particulate form.

Experimental Set-Up

The nanoparticles G3 and G3-DT formulated as described in Ex 1 and 2 were compared with the active component QHC form for the cancer cell killing effect. The samples were 5-fold serial diluted in 6 steps starting from 100 μg/ml, and incubated for 3 days with HL-60 AML cells. Then the cells were stained and read by the FMCA method.

Result

Figure 6:
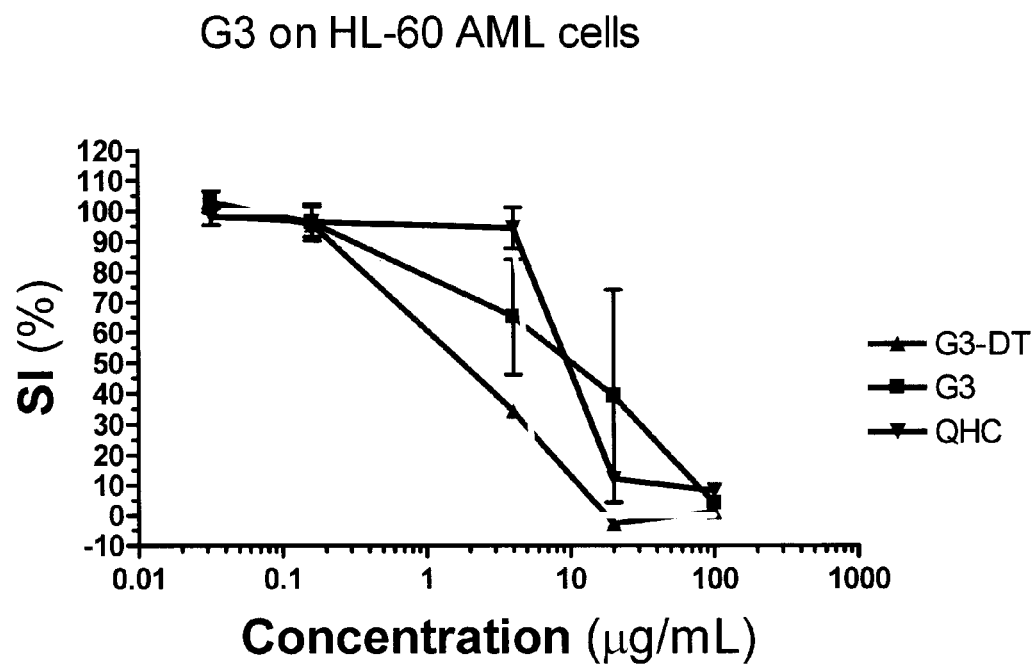
FIG. 6. The titration curves of G3, G3 with DT incorporated (G3-DT) and non-particulate QHC read on HL-60 AML cells FIG. 7. The stand alone and combination effects of G3 and cytarabine on HL-60 AML cells FIG. 8. G3 enhances the killing capacity of daunorubicin on HL-60 AML cancer cells FIG. 9. The titration curves of G3, G3 with DT incorporated (G3-DT) and QHC on PC-3 prostate cancer cells FIG. 10. The stand alone and combination effects of G3 and docetaxel on PC-3 prostate cancer cells.

G3 ($IC_{50}$=3.144 μg/ml) and G3-DT ($IC_{50}$=3.12 μg/ml) inhibited the growth of the AML cells more efficiently than QHC (IC50=8.473 μg/ml) (FIG. 6).

Conclusions and Discussions

Essentially, both G3 and G3-DT have stronger cancer cell killing effect compared to QHC. DT alone has no cancer cell killing effect (not shown). The non-particulate QHC causes local reaction that is abolished by the particulate forms. More importantly, incorporation of DT into the G3 particles leads to the induction of IL-12 cytokine response, which is crucial for anti-viral and anti-tumour immune responses.

Example 7

Cytarabine is a commercially available cytostatic drug used for treatment of Acute Myeloid Leukemia (AML). This example was set up to explore the capacity of G3 to enhance the cancer cell killing effect of cytarabine.

Experimental Set-Up

Figure 7:
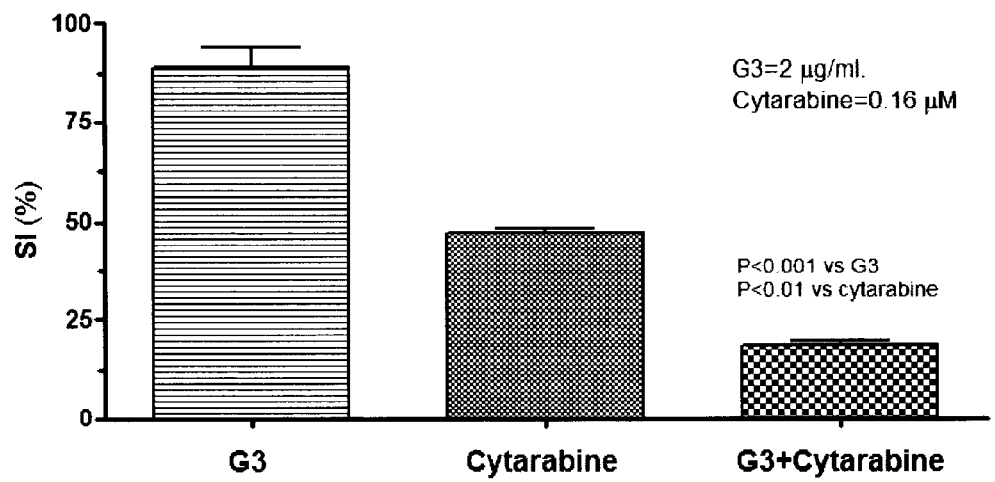

HL-60 AML cells were exposed for 3 days at predetermined concentrations of G3 and cytarabine separately and in combination of these two as shown on FIG. 7. Then the cells were stained and read for cancer cell killing effect by the FMCA method.

Result

After incubation for 3 days, G3 or cytarabine alone at the selected concentrations killed less than 5% and 55% the cells respectively. When they were combined, the killing rate was elevated significantly ($P<0.01$) to about 75% (FIG. 7).

Conclusions and Discussions

The G3 particles significantly enhance the killing effect of cytarabine on HL-60 AML cells. Treatment with the cytostatic drug cytarabine causes side effects with discomfort for patients. Since G3 particles are virtually non-toxic, the combination treatment with G3 and cytarabine would also have prospect for increased efficacy and reduce the side effect by lowering the dose of cytarabine. Moreover, the treatment period may be increased facilitating improved treatment.

Example 8

This example demonstrates that G3 has added cancer cell killing effect on the commercial cytostatic cancer drug daunorubicin on the non-solid tumour human Acute Myeloid Leukemia (AML) cells.

Experimental Set-Up

Figure 8:
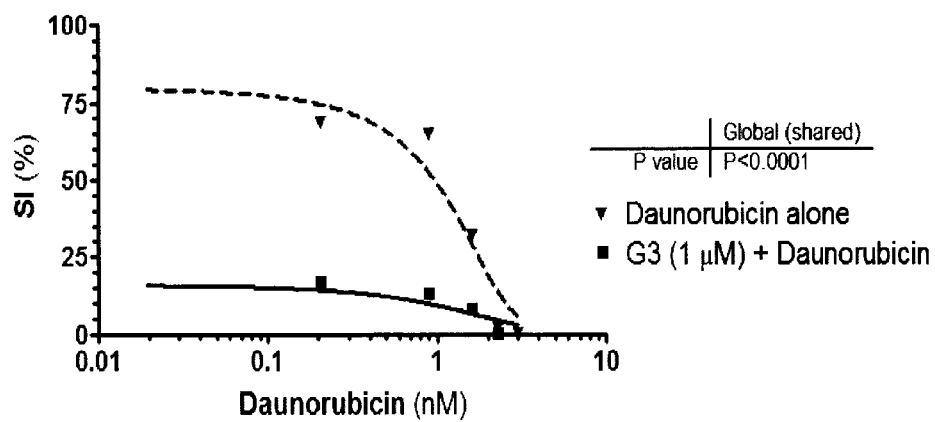

HL-60 AML cells were exposed to a fixed concentration (1 μM) of G3 combined with increasing concentrations of daunorubicin starting from 1000 nM, and incubated for 3 days. Then the cells were stained and read by the FMCA method.
Result
G3 enhances significantly (P<0.0001) the cancer cell killing effect of daunorubicin compared to daunorubicin stand alone (FIG. 8). The implication is that the dose of daunorubicin can be considerably reduced.
Conclusions and Discussions
The G3 particles enhance synergistically the killing effect of daunorubicin on HL-60 AML cells. Since G3 particles are virtually non-toxic, it is likely the dose of the cytostatic drug daunorubicin would be considerably reduced in a combination therapy with G3 implicating better treatment effect, and because of lowered side effect the treatment can be continued for longer periods in patient sensitive to daunorubicin.

Example 9

This example was designed to compare the effects of G3 and G3 with incorporated DT (G3-DT) on solid tumours exemplified by human prostate cancer cells PC-3.

Experimental Set-Up

Figure 9:
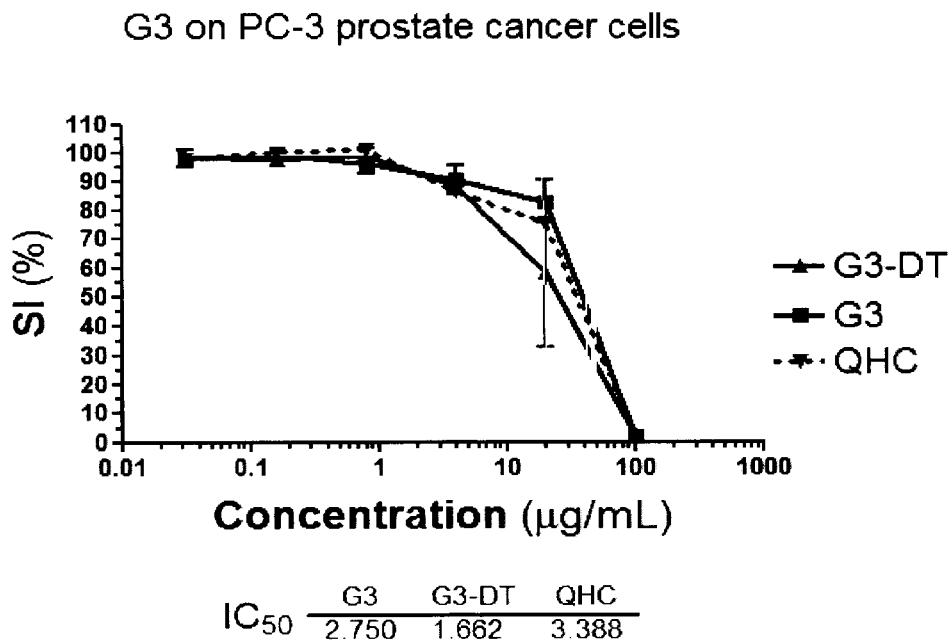

G3 and G3-DT were compared with non-particulate QHC. The samples were 5-fold serially diluted in 6 steps starting from the concentration of 100 μg/ml, and incubated with PC-3 prostate cancer cells for 3 days. Then the cells were stained and read by the FMCA method.
Result
The G3 particles ($IC_{50}$=2.75 μg/ml), and the G3-DT ($IC_{50}$=1.662 μg/ml) inhibited the growth of the prostate cancer cells more potently than the same active component QHC alone ($IC_{50}$=3.388 μg/ml) (FIG. 9)
Conclusions and Discussions
G3 in this example had a better killing effect on the PC-3 prostate cancer cells as that of QHC. By incorporation of DT into the particle i.e. G3-DT, the cancer cell killing effect of G3 is enhanced. The DT alone has no cancer cell killing effect. Its added effect here in killing PC-3 cancer cells implicates enhancement of the G3 effect maybe also reduction of the side effects if any. To note the QHC in non-particulate form is comparatively efficient in vitro, but in vivo QHC remains at the site of injection resulting in low bioavailability and local side effects.

Example 10

This example demonstrates that the combination effect between G3 and a commercial drug docetaxel on the prostate cancer cells PC-3 from a solid tumour.

Experimental Set-Up

Figure 10:
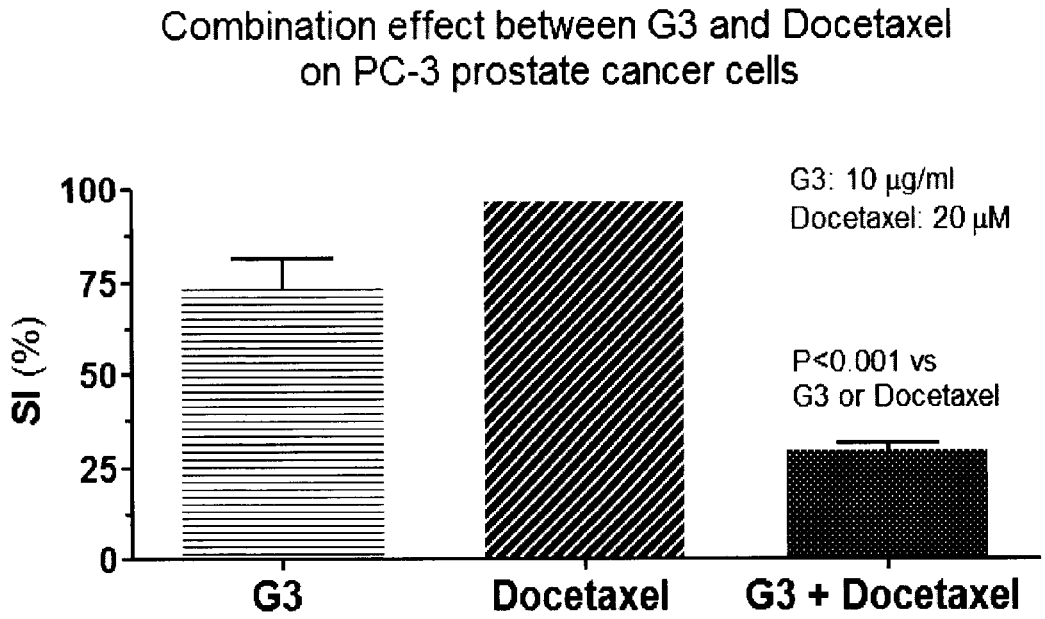

PC-3 cells were exposed for 3 days at pre-determined concentrations of G3 and docetaxel separately and in combination as shown on the graph. Then the cells were stained and the cancer cell killing effect was read by the FMCA method.
Result
The cancer cell killing effect of G3 or docetaxel alone at the selected concentrations killed slightly more than 35% and 2% of the PC-3 cells respectively. When these two drugs were combined, the killing rate was significantly elevated (P<0.01) to about 75%. (FIG. 10).
Conclusions and Discussions
The G3 particles significantly enhance the cancer cell killing effect of the cytostatic docetaxel on the prostate PC-3 cancer cells implicating increased efficacy and reduced dosing of the cytostatic drug with reduced side effect in view of the fact that G3 particles are virtually non-toxic.

Example 11

This example was designed to explore combination effect between G3 and a recent and under patent covered cytostatic commercial drug cabazitaxel on the solid tumour human prostate cancer PC-3 cells.

Experimental Set-Up

Figure 11:
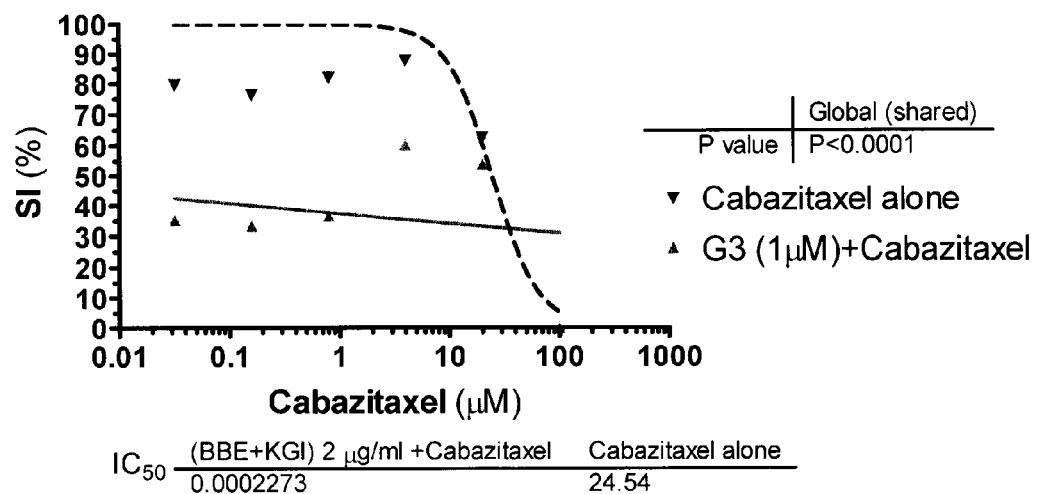
FIG. 11. G3 enhances the killing effect of cabazitaxel on PC-3 prostate cancer cells FIG. 12. G3 formulated with QHA kills ACHN kidney cancer cells more efficiently than that of G3 formulated with QHC.

PC-3 prostate cancer cells were exposed to a fixed concentration (1 μM) of G3 combined with increasing concentrations of cabazitaxel starting from 100 μM, and incubated for 3 days. Then the cells were stained and read by the FMCA method.
Result
Cabazitaxel alone killed the PC-3 cancer cells with an $IC_{50}$=25.54 μM. When Cabazitaxel was combined with G3, the cancer cell killing effect was significantly ($IC_{50}$=0.00023 μM, P<0001) enhanced (FIG. 11).
Conclusions and Discussions
The G3 particles significantly and synergistically enhance the killing effect of cabazitaxel on PC-3 prostate cancer cells implicating prospects for better efficacy, reduced side effect and possibility for prolonged treatment in view of the fact that G3 particles are virtually non-toxic.

Example 12

This example was designed to explore the capacity of G3 particles formulated with another important *Quillaja* saponin fraction QHA in killing solid tumours exemplified here with ACHN kidney cancer cell line since it was observed before that Duecom particles (China Patent 200780043107) formulated with this fraction had a stronger killing capacity than Duecom particles formulated with fraction C (QHC).

Experimental Lay-Out

Figure 12:
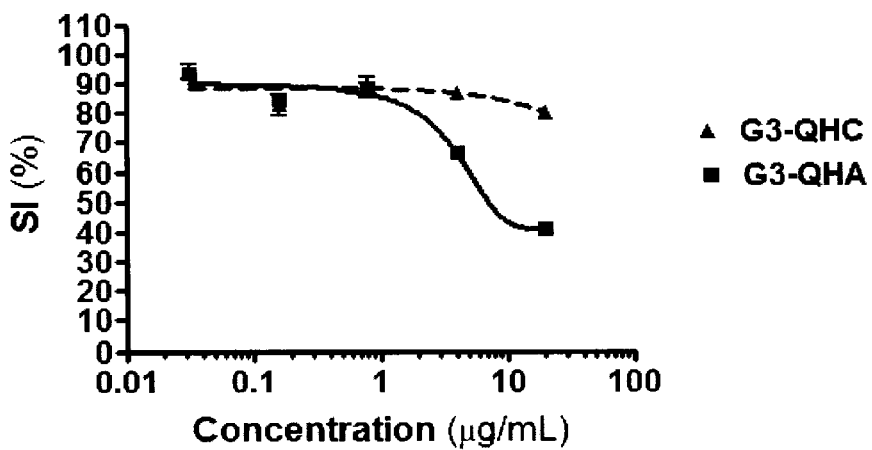

G3 formulated with QHA and QHC were diluted 5-folds, 6 steps from 100 μg/ml down to 0.032 μg/ml and incubated with ACHN renal carcinoma cells at 37° C. for 3 days. The cell survival was determined by the FMCA method.
Result
G3 formulated with QHA kills significantly (P<0.01) more ACHN kidney cancer cells than that of G3 formulated with QHC (FIG. 12).
Conclusions and Discussions
This result is virtually identical to the previous observation with Duecom particles formulated with QHA and QHC i.e. that formulations with QHC is selectively killing more non-solid tumour cells while formulations with QHA is preferably killing more solid than non-solid tumours. This tumour type specific killing property with G3 formulations could be harnessed as for Duecom particles to avoid killing normal cells in another category.

Part III. G3 as Adjuvant

Example 13

Animal trial of G3 particle as an adjuvant against split influenza virus

Experiment A

The adjuvant effect of G3 in comparison to ISCOMs was evaluated in an animal trial on C57BL/6 mice. The disintegrated and inactivated influenza virus was used as the model antigen in the experiment.

Experimental Layout

Six mice per group, immunized twice 4 weeks apart, blood samples were taken at 3 weeks after the first immunization and 4 weeks after the second immunization. At the necropsy i.e. 3 week after the second immunization, spleen cells were analysed for cytokine production as described in materials and methods. To facilitate the understanding, grouping of the animals is shown in FIG. 13A1.

Result
 The G3 and ISCOM induced in dose dependent manner detectable levels of HI antibody after the $1^{st}$ immunization. After the $2^{nd}$ immunization, the level of HI antibody increased considerably (a clear boost effect) also in a dose dependent manner for the G3 adjuvanted formulations. The ISCOM, G3 and G3 with DT incorporated adjuvanted formulations induced considerably higher levels of HI antibody than the non-adjuvanted commercial vaccine, i.e. similar or higher levels of HI responses were recorded between animals immunized with G3 and ISCOM formulations at two time points after the $1^{st}$ (FIG. 13A2) and the $2^{nd}$ (FIG. 13A3) immunizations.
 Similar or even higher levels of IFN-γ and IL-4 responses were detected in spleen cells after in vitro re-stimulation with the split virus in animals immunized with vaccines adjuvnted with G3 and ISCOM formulations at the necropsy, 4 weeks after the $2^{nd}$ immunization (FIG. 13A4).

Experiment 13B

In this experiment, 3 different flu antigens (see below) were admixed with G3 or G3/DT particles and administered subcutaneously to C57BL/6J mice twice, 4 weeks apart. Challenge infection was carried 4 weeks after the $2^{nd}$ immunization. Weight lose and survival rate were recorded daily for 6 days after challenge infection.

The G3 and G3/DT formulations were produced by MoreinX as described in Materials and Methods. The mouse stain used was C57BL/6J (see Materials and Methods). The vaccination experiment was carried out at Viroscience lab, Erasmus MC, Rotterdam, the Netherlands, which is an international influenza virus reference laboratorium.

Evaluation G3 and G3/DT in Mouse Model
 C57BL/6J mice (female, 6-8 weeks old, n=7-14 mice/group)
 Vaccine
  Seasonal trivalent split virion influenza vaccine (2012/2013, VAXIGRIP®)
   A/California/7/2009 (H1N1 pdm09) (5 µg/mice)
   A/Victoria/361/2011 (H3N2) (5 µg/mice)
   B/Wisconsin/1/2010 (FluB) (5 µg/mice)
 Adjuvants
  63/DT (5 µg/mice)
  G3 (5 µg/mice)
  PBS
 Challenge virus (antigenically distinct)
  A/PR/8/34 lethal dose
Evaluation G3 and G3/DT in Mouse Model

| | VACCINE | ADJUVANT | INFECTION |
|---|---|---|---|
| 1. | Split whole viron | G3DT | |
| 2. | Split whole viron | G3 | |
| 3. | Split whole viron | PBS | |
| | | | A/PR/8/34 |
| 4. | PBS | G3DT | |
| 5. | PBS | G3 | |
| 6. | PBS | PBS | |
| 7. | PBS | + PBS → PBS | |

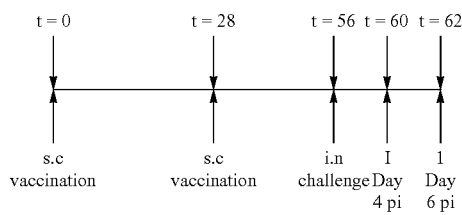

Results

After two immunizations and challenge infection (see above), the survival was recorded daily for 6 days as in FIG. 13B1. Only animals immunized with G3/DT adjuvanted vaccine were protected including all animals in the group against the hetrologous virus (A/PR/8/34) challenge infection.

The body weight in the G3/DT vaccinated group decreased for 4 days and increased sharply thereafter.

Figure 2:
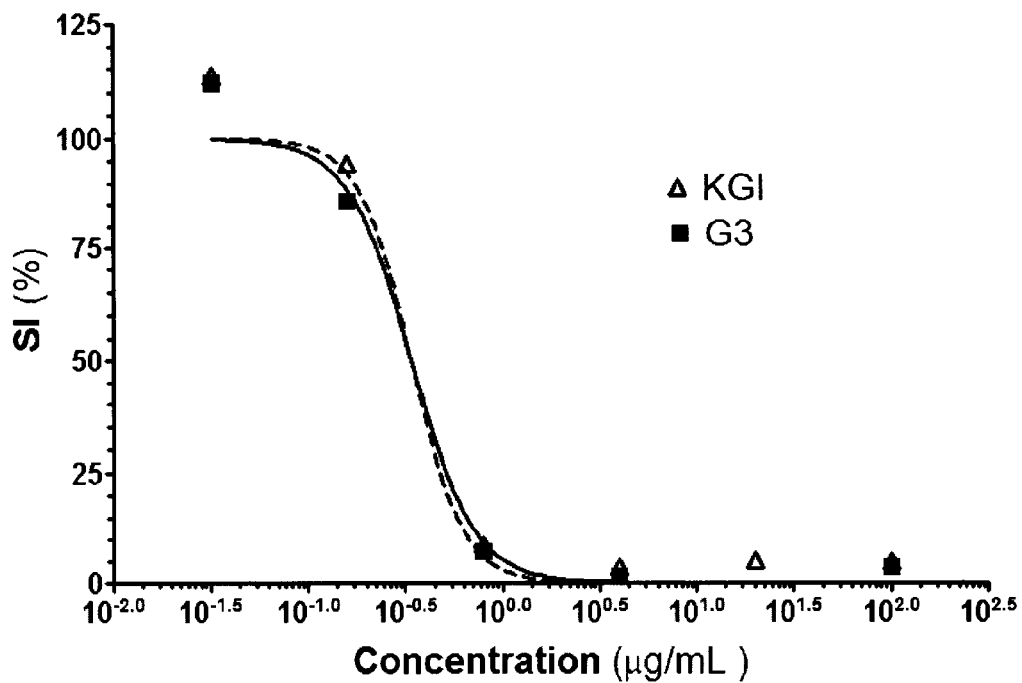
FIG. 2. Comparison of cancer cell killing capacity between G3 and KGI nanoparticles both containing QHC tested on U937 cells. G3 and KG1 have virtually the same anti-cancer cell killing effect on the model tumour cells (P=0.8422).
Figure 14A:
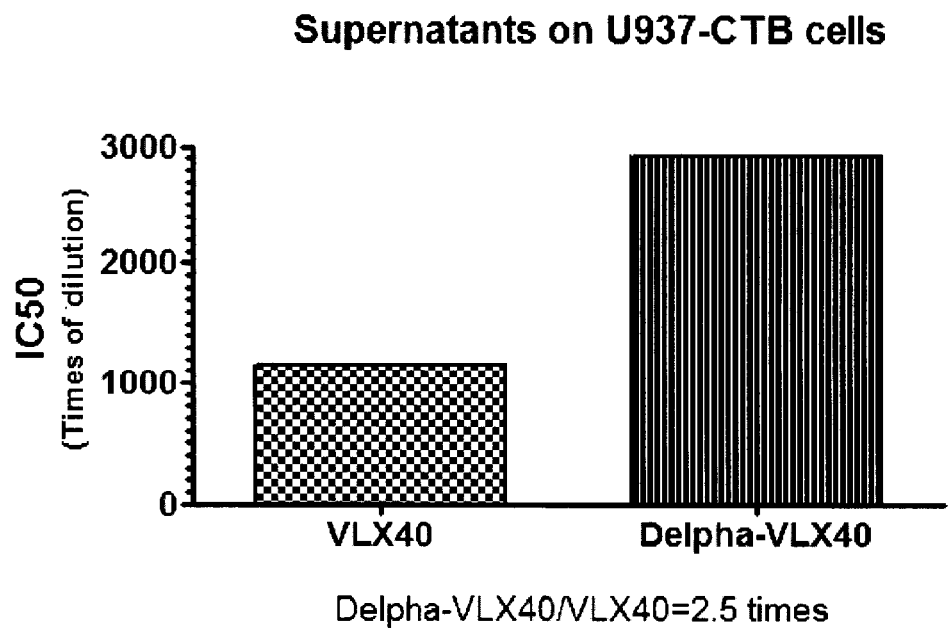
Figure 14B:
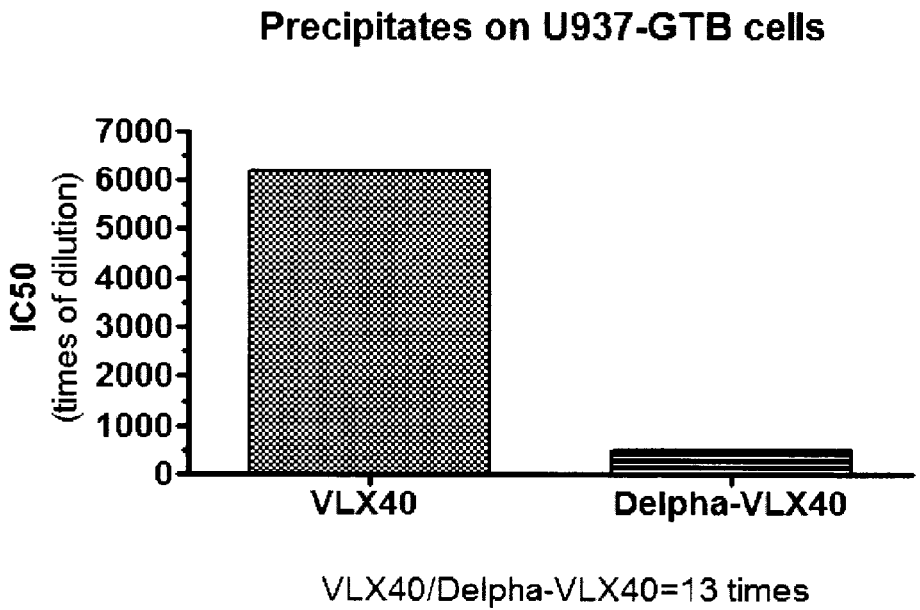

Four days after the challenge infection, the virus load was significantly lower in vaccinated animals than the non-vaccinated animals. 6 days after the challenge infection, drastic reduction of the virus load was recorded only in the animals immunized with G3/DT adjuvanted vaccine (see FIG. 14B2).

The antibody responses measured by hemoglutini inhibition (H1) and by virus neutralization (VN) were both high in groups of animals immunized with G3 and G3/DT adjuvanted vaccines, significantly higher than the commercial vaccine against the homologous virus. No vaccine induced H1 or VN antibody responses against the hetologous challenge virus showing that the challenge virus lacked epitopes connected with immune protection (FIGS. 13B3 and B4). Thus, it cannot be expected that the antibody response should confere immune protection against the hetologous challenge virus.

The T cell responses induced by various vaccine formulations and the controls (listed in FIGS. 13B5, 6 and 7) were measured by in vitro stimulation of spleen cells collected 6 days after the challenge infection (see Materials and Methods). The stimulation antigens were the peptides polymerase A $(PA)_{224-233}$ and the nucleo protein $(NP)_{366-374}$, used for the determination of the proportion of responsive $CD8^+$ T cells as indicated in the figures, i.e. these peptides are recognized as conserved Tcells epitopes.

G3/DT adjuvanted vaccine formulation induced superior immune responses than the G3 adjuvanted formulation and the commercial vaccine as shown in FIGS. 13B: 5, 6 and 7.

G3/DT adjuvanted vaccine formulation induced significantly higher T cell responses than the other vaccine formulations measured by the proportion of positive T cells against $NP_{366-374}$ peptide. Less prominent response was recorded against $PA_{224-733}$ peptide. (FIGS. 13B: 5&6) G3/DT adjuvanted vaccine induced a potent IFNγ response (FIG. 13B7), which was measured in $CD3^+CD8^+$ cells after restimulation with $NP_{366-374}$ peptide.

Discussion

In experiment A, both antibody-mediated and cell-mediated immunities induced by G3, G3/DT and ISCOM formulations were qualitatively and qualitatively similar. Experiment B confirmed the results from experiment A. In addition, exp 13B shows that G3 and G3/DT induced similar magnitude of neutralizing antibodies being significantly higher than that induced by the commercial vaccine. However, none of the vaccines elicited detectable antibodies to the challenge virus showing that the virus strains used in the vaccines tested in this experiment had antigenic antibody determinants considered to convey immune protection by commercial vaccines based on antibody measured by HI or virus neutralization. Thus, the immune protection was conveyed by the T-cell responses including cytotoxic T-cells and interferon-γ that the DT component strongly induced as shown in this experiment, thereby this component is contributing to a new adjuvant with property to broaden immune response to influenza virus and other pathogens where T-cell responses can have such effect including T-cell responses that are not seen in the vaccines used on the market.

G3/DT adjuvanted vaccine formulation induced superior-cell immune responses than the G3 adjuvanted formulation and the commercial vaccine as shown in FIGS. 13B: 5, 6 and 7.

Protection against the hetologeos virus A/PR/8/34 infection was only induced by G3/DT adjuvanted vaccine, which could be attributed to the induction of anamnestic virus-specific CD8+ T cell responses, which were not observed with the other vaccine formulations.

Conclusion

The G3/DT invention introduces a new adjuvant that enhances immunity protecting against infection with viruses that lacks antigenic determinants compatible with the vaccine antigens including escape variants of influenza virus lacking protective antibody determinants. Such immune protection can be conferred over T cell epitopes, e.g. in the nucleo protein. Moreover, the protection was accompanied by a drastically reduced virus load in the lungs soon after the challenge infection.

Besides enhancing a potent antibody response improving that arm of the immune system over present available commercial vaccines, the G3/DT adjuvant broadens immune protection based on T cell immunity, implicating an innovative adjuvant formulation applicable for infectious agents evading immunity and that conveniently can be added to the present vaccines on the market.

Part IV. G3 as a Drug Delivery System

Example 14

VLX40 was considered to be a promising drug for treating cancer. The research to market ceased because VLX40 could not be formulated to be suitable for administration to animals in preclinical tests and consequently not for subsequent tests in patients. The reason was that VLX40 could not be rendered soluble in water, which is necessary to be taken up after parenteral or oral modes of administration by the body. This experiment was designed to find out if the G3 technology could solve the problem and make VLX40 water soluble.

Experimental Set-Up

- VLX 40 was first dissolved in an organic solvent DMSO to yield a concentration of 20 mM (5.8664 mg/ml, the highest concentration recommended) and designated as the stock solution.
- VLX40 at a concentration of 100 μg/ml was used as a control for VLX40 in water i.e. as a virtually non-water soluble formulation.
- 8.5 μl of the VLX40 stock solution was mixed with 50 μl chloroform in an Ependorf tube containing 500 μl water to form an artificial lipid membrane (see Example 1). In the second step, the 10 μl of Quil A (100 mg/ml in water as the stock solution) was added and incubated overnight at 37° C. This is the G3-VLX40 formulation, essentially formed in the same way as described in Example 1.
- The VLX40-DMSO control (2) and the G3-VLX40 suspension/solution (3) were collected and tested on U937-GTB cells after being serially diluted from the same concentration as above, and IC50s were calculated from the regression curves.

Results

The stock solution (1) added to water gave rise to a visible sediment or precipitate i.e. as expected from previous experiments. Thus, VLX40 could not be dissolved in water from the control tube (2). The formulation of G3-VLX40 particles (3) was confirmed by electron microscopy of the clear solution/suspension. There was no precipitate or only very scanty precipitate from the tube containing the G3-VLX40 formulation.

The various formulations were tested for function i.e. in a bioassay for the cancer cell killing effect of U937 cells (see Materials and Methods). The water phase of the VLX40/DMSO (2) had low anticancer effect (expressed as IC 50), meaning that just a very small fraction of VLX 40/DMSO mixture is dissolved in water (FIG. 14 A).

In contrast, the water phase of the G3 VLX-40 particle formulation (3) had high anticancer cell activity as shown in FIG. 14A.

The sedimented non-soluble part was also tested in vitro for the cancer cell killing effect. High cancer cell killing effect was recorded with VLX 40/DMSO (2) in the water-insoluble precipitate, the scanty water-insoluble precipitate of G3-VLX 40-formulation had a low cancer cell killing effect (FIG. 14B).

These experiments has been repeated 3 times.

Conclusion and Discussion

About 50-100 micrograms VLX 40 was dissolved with 2 mg G3 measured as the *Quillaja* component in a volume of 1 ml of water. It should be noted that the concentration of G3 particles can be increased by increasing the concentration of the G3 particles, for example 10 mg/ml of the G3 formulation can be in a clear solution. We can also change the composition of the G3 particles to facilitate the incorporation of larger amount VLX 40. This example clearly demonstrates that the G3 particle is filling an unsolved demand to facilitate formulation of drugs for clinical use that without the G3 technology could not reach the patient because the drugs could not be made water soluble with the existing technologies.

Example 15

This example demonstrates that G3 particle, as a drug delivery system, can incorporate readily another two non-water soluble anticancer drugs busulfan and roscovitine, making them water soluble.

Experimental Set-Up

Two µl busulfan (50 mg/ml in DMSO) or 1 µl roscovitine (100 mg/ml in chloroform) together with 2 µl cholesterol (100 mg/ml in chloroform) were used to form the lipid membrane with busulfan or rocovitine respectively, using the way method as described for step 1 in Example 1. Then 10 µl QHC (100 mg/ml in water) was added as for step 2 in Example 1 to give a molar ratio of QHC:cholesterol:busulfan/roscovitine=1:1:0.5.

Results

For both compounds i.e. busulfan and roscovitine, clear solutions were visualized i.e. sediment or cloudiness in the water phase caused by the insoluble drugs were eliminated by incorporating them into the water soluble G3 particles.

Discussion

This example, similar to example 13, shows once again that the capacity of G3 as a general platform for making non-water soluble lipophilic drugs/molecules water soluble by incorporating them into the G3 particles. Considering that about 40% of the anticancer drug candidates are not water soluble, therefore, cannot be further developed into commercial products, therefore, our invention can drastically improve the situation.

Example 16

In this example, we have explored whether a lipophilic vitamin i.e. vitamin D3 can be integrated into the G3 nanoparticle in order to make it water soluble. It was dissolved in chloroform and incorporated into the G3 particle as described in example 1 and for more details see Materials and Methods.

Experimental Set-Up

First, 50% cholesterol and 50% vitamin D3 were used to form the lipid membrane. Quil A was added into the water phase to generate the G3 particles (for details, please refer to Example 1). 100% Cholesterol and 100% Vitamin D3 in water were used as the controls. Samples with vitamin D3 incorporated in G3 particles were analysed at the Uppsala University Hospital Laboratory on a DiaSorin Liaison automatic instrument.

Results

The water phase recovered in step 2 was a clear solution and no sediment could be detected. More vitamin D3 was detected in the G3-vitamin D3 formulation based on non-fractionated *quillaja* (950 nmol/L) than in the *quillaja* QHC fraction formulation i.e. 55 nmol/L. In a dilution experiment the concentration of vitamin D3 was linear in the read out showing that there was a homogenous suspension of particles i.e. no aggregation being in agreement with other G3 particles as seen in FIG. 1. In comparison, only trace amount of Vitamin D3 was detected in the vitamin D3 control and no vitamin D3 was present in the cholesterol control.

Conclusion and Discussion

Vitamin D3 is an essential vitamin that is poorly taken up by the body in the lipid form by oral or parenteral routes. Thus, a water soluble form will facilitate its uptake by those routes. We show in this experiment that vitamin D3 is incorporated into the G3 nanoparticle with the non-fractionated as well as QHC fraction of *quillaja* saponin. Importantly, the linear read out of the dilution experiment shows a homogenous desperation of the particles that has been revealed by electron microscopy for G3 particles in general (see FIG. 1). For food the non-fractionated *quillaja* saponin is well accepted and used e.g. in beverages including beer and also other types of food. Therefore, the more economical alternative for the formulation of G3 for delivery of this vitamin is a non-fractionated *quillaja* as base for the G3 formulation. In this experiment more D3 was incorporated into the G3 with non-fractionated *quillaja* saponin than in the G3 particle with the QHC saponin fraction.

Example 17

In this example, we studied the stability of G3 particles stored at 4° C. for 15 months, which is crucial data for biological products.

Experimental Set-Up

Visual examination for its physical characteristics. Two G3 batches were formulated one 15 months and the other one week ago. Both were tested on HL-60 AML cancer cells regarding their cell killing and IL-8 inducing capacities as stated in the previous examples and as described in Materials and Methods.

Results

No physical differences between these two G3 preparations were recorded i.e. both are transparent and no sedimentations were observed.

Figure 15A:
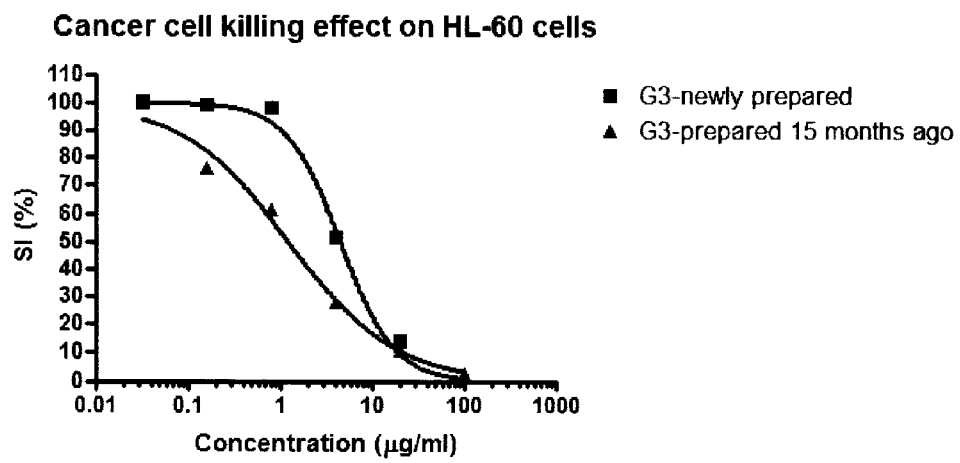
FIG. 15A. Stability test evaluated by the cancer killing effect.

The capacity of the G3 particles prepared 15 month ago has similar levels of cancer cells killing capacity as that of the newly prepared G3 particles on HL-60 AML cancer cells (FIG. 15A).

Figure 15B:
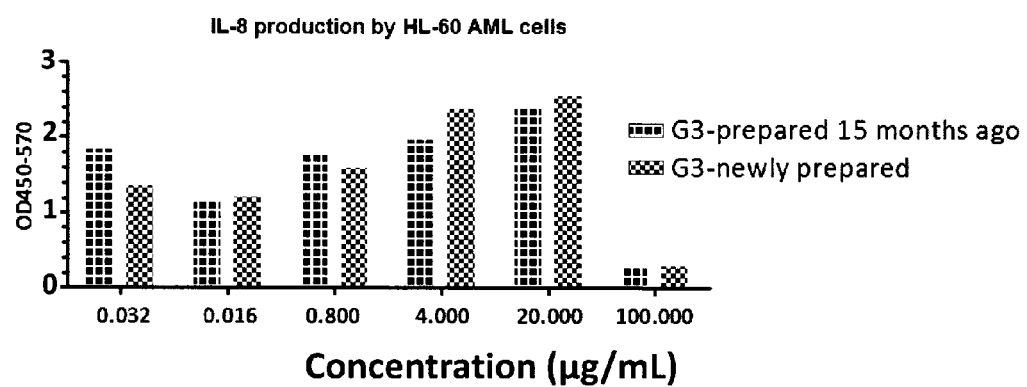
FIG. 15B. Stability test evaluated by the production of IL-8.

The capacity of G3 prepared 15 month ago and that of recently prepared G3 in stimulating HL-60 cells to produce IL-8 are virtually identical (FIG. 15B).

Example 18

Cholesterol Incorporation into G3 Particles

In the following three examples the formation of G3 will be described based on:
  Composition i.e. of the two basic components Cholesterol and *Quillaja* Saponin.
  Cholesterol-*Quillaja* saponin molecular interactions.
  Size and morphology determined by transmission electron microscopy.

The G3 particle consists of *Quillaja* Saponin and cholesterol that are formulated as described in patent application P13-0327SE. This example informs about the rate of incorporation of cholesterol from the artificial cholesterol membrane into the *Quillaja* micelle to form the G3 nanoparticle. The method of incorporation is described in Materials and methods along three steps including solubilization of cholesterol, formation of the membrane and extraction of cholesterol to the water phase and eventually incorporated into the *Quillaja* micelle forming the G3 particle. The G3 nanoparticles were harvested and prepared for measuring the cholesterol in ELISA as described in Materials and Methods according to manufacturer's description.

Results

The Cholesterol content was estimated by ELISA as described in Materials and Methods and the proportion of cholesterol in the G3 particle is shown in Tables 2A and B and FIG. 18:1. Totally from 19 samples the mean weight percent it is found that about 45% of the cholesterol attached to the wall by hydrophobic interaction was incorporated into the G3 nanoparticle. The molar ratio of *Quillaja* vs cholesterol in the suspension is 2 Mol *Quillaja* Saponin and 1 Mole of cholesterol.

The Chemical Structure of G3 Particles

This example studies the structure and the interaction of cholesterol and *quillaja* saponin. In nature, Cholesterol alone doesn't form natural membrane in cells. In water a phospholipid or another lipid molecule is needed to form a membrane e.g. a liposome with larger hydrophilic moiety that is expanding into the water. We solved that part by anchoring the cholesterol molecules to a solid hydrophobic surface. The first contact of *quillaja* micelles occurs with the proton in the 3-position of cholesterol forming hydrogen bonds with $COOH^-$ QA sugar moieties. To note in the natural membranes Cholesterol is forming ester bonds with aldehyde groups or $COOH^-$ groups of e.g. phosphatidylcholine bonds[6]. That is can we mimic the natural membrane? In the *quillaja* molecules there are both an aldehyde group in the position 4 of the triterpen skeleton and $COOH^-$ groups that potentially are forming ester bonds forming strong enough to extract the cholesterol from the hydrophobic anchoring. For more information and analyses see FIGS. 18:2 and 18:3.

Transmission Electron Microscopy (TEM)

Transmission Electron Microscopy (TEM) is a vital characterization tool for directly imaging nanomaterial to obtain quantitative measures of particle and/or grain size, size distribution, and morphology.

The G3 is a spherical nanoparticle described to have diameter of 20 nm (see patent application WO 2013/051994 A) being confirmed in FIG. 18:4. In contrast to the ISCOM having three basic components, the G3 nanoparticle is based on two components being cholesterol and *Quillaja* Saponin with the content on molar basis of 2 *Quillaja* Saponin to 1 cholesterol (see Table 18:1). Electron microscopy was carried out as described in Materials and Methods.

Results

In FIGS. 18:4, the morphology is depicted showing densely packed well dispersed particles and the dispergation is essential for its medical use e.g. in vaccines. Confirming previous studies the particles have a diameter of 17 to 22 nm (88%). (See Table 3 and FIG. 18:4A). In FIG. 18:4 B, the sub-structural morphology is described showing that the G3 particle is built up by 6 nm hexagonal rings of Cholesterol and *Quillaja* molecules subunits. See also the illustration in FIG. 18:5.

Discussion

Figure 1B:
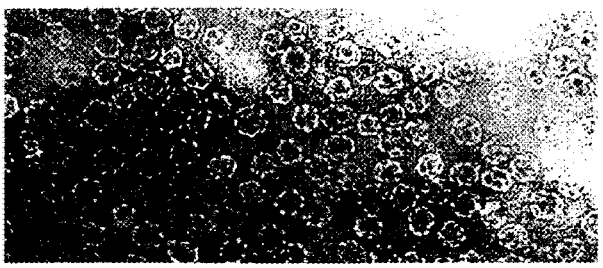
FIG. 1B. The electron microscopy shows an ISCOM like particle comprising cholesterol, QHC and phosphatidylcholin in a molar ratio: 1:1:0.5. The particles is prepared as described using a technology similar to that described in Example 1 according design C in Example 1 having a diameter of about 40 nm i.e. using the evaporation method. The morphology and size are distinctly different from those of a nanoparticle according to the invention as depicted in FIG. 1A.
Figure 1C:
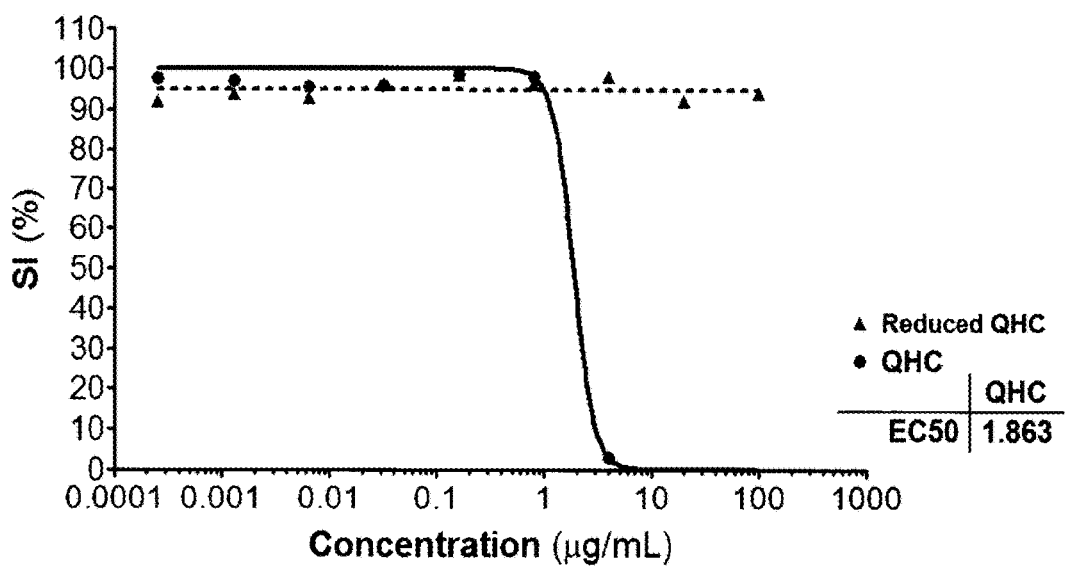
FIG. 1C. Reduced QHC (dotted line) shows no killing effect of U937 cancer cells at the concentrations (up to 100 μg/ml) tested on U937 cells, stained with the AlamarBlue method. In contrast not reduced QHC (solid line) killed cancer cells.

G3 nanoparticles formation process will not lead to any denatured *Quillaja* Saponin because the QA has only been in water or buffered water solutions. Therefore, the active groups of *Quillaja* Saponin remains not denatured as non-formulated or non-particulate Saponin fractions as defined by Kerstin et al[17]. ISCOM nanoparticles has a size of around 40 $nm^3$, while the G3 particles is smaller and has a diameter around 20 nm according to our calculation on >3500 particles. The morphology as seen in FIG. 18:4B is composed by 72 subunits by the rough estimation that could be done and considerably different from the Iscom morphology as seen in FIG. 1B. The structure of G3 is different form Iscom for various reasons e.g. in view of the opportunity of cholesterol to interact with phosphatidylcholine in the Iscom as the case is in the mammalian cells where cholesterol naturally interacts with phosphatidylcholine groups see review[6].

The basic compositions of G3 components are *Quillaja* Saponin and Cholesterol with a 2:1 molar ratio calculated from the amount of QA and Cholesterol levels in complex in the G3 suspension (see Table 2A and B).

*Quillaja* as described by Bankefors[5] (Thesis, FIG. 6, page 18) contains two oligosaccharide chains A: C-3 oligosaccharide chain and B: C-28 oligosaccharide chain attached to a hydrophobic backbone (aglycone) that can contain any of six aglycones (Thesis, FIG. 6, page 18). Bankefors also describes this molecule can be fragmented.

Monosaccharaides in the oligosaccharide chains are listed in Bankefors thesis FIG. 3 on pages 13-15 where also the general *quillaja* structure is depicted. QHC as referred in this patent contains the fatty acid linked by an acyl group to fucose to the *quillaja* molecule.

The lack of the fatty acid yields QHA as described in this application. FIG. 18:2A depicts a general *quillaja* molecule as used in various publications including a table of examples of substituted monosaccharaides (R)[4]. C-3 oligosaccharide chain contains a glucuronic acid (GlcA) with a reactive $COOH^-$ to which Xylose is linked explaining that it is competing/blocking the binding of GlcA to cholesterol polarized proton by hydrogen binding. An alternative in the position of Xylose is another pentos i.e apiose and that should block in the way as described for Xylose. The question is if hydrogen and Van der Wahl bonds are strong enough to extract the cholesterol from its membrane on the solid phase.

In nature, above all in the mammalian cells, Cholesterol is known to exert strong interaction with phosphatidylcholine involving molecular bindings to carboxyl and aldehyde groups FIGS. 18:2B and 18:5 (W. David Nes et al 2011[6]). The interaction by QA-cholesterol is strong by the well exposed molecular groups on cholesterol (OH) to the *quillaja* sugar carboxyl moiety, but also the aldehyde group is reacting as seen in example likely resulting in carbonyl bindings preferentially ester bounding (FIGS. 18:2&3 & 18:5). In example 20 the biological effects of G3 on cancer cell killing and immune stimulation by the terpene aldehyde and the sugars are described being in accord with strong chemical interactions. The interaction between the terpen aldehyde group and the QA micelle is supported by the finding that the reduction of the aldehyde group abolishes the cancer cell killing effect (example 19, FIG. 19:3) requiring a molecular interaction.

G3 is stable for up to 2 years essentially due to the strong molecular bounding between the QA and cholesterol. This long lasting stability is critical for medical use. Whether the stability of Iscoms could be explained or partly explained by the molecular bindings to phosphatidylcholine could not be excluded until experimentally verified.

The cholesterol membrane is also essential for incorporating other hydrophobic or amphipathic molecules as drug or proteins as shown in example 1 formulating it as an efficient carrier/delivery particle.

In conclusion, Formulated *Quillaja* Saponin to G3 represents potential a new drug and drug delivery for various uses including vaccine and cancer treatment.

Example 19

Modification of *Quillaja* Saponin

Oxidation of *Quillaja* Sugars (Hexose and Pentose Rings)

Reduction of Aldehyde Group by Borohydride Treatment

The *Quillaja* molecule is surrounded by sugars being hexose or pentose rings (Se example 18) that are strongly bioactive. It is expected that these sugars will interact with cells via lectin receptors that by definition are ligands to sugar moieties.

The aldehyde's importance may relate to the binding to cell surface and immune cell activation[18].

This example was designed to explore whether the modification of the sugar moieties hexose and pentose rings by oxidation with periodate and reduction of the aldehyde group in position C-23 on the triterpen skeleton of the *quillaja* molecule by borohydride would affect:

The *quillaja* (QA) sugars are essential as ligands to lectin cell receptors starting the biological responses. Here we analyze the effects of modulation of QA sugars by periodate treatment considering the induction of IL-8 as an immune modulation (adjuvant) marker and the cancer cell (U937) killing effect assayed by the Alamar blue assay (se Materials and Methods).

The reactive aldehyde group on the *quillaja* triterpen skeleton is said to be of importance and even required for the adjuvant activity[19]. Here we analyze the effects of reducing the aldehyde by borohydride treatment (see Materials and Methods) for cancer cell killing and IL-8 production i.e. adjuvant effect[19].

These effects have not been tested before on the QA assembled into a particulate form, which is being done here both after the above sugar and reduction modifications Results Oxidation of Sugar Moieties on QA The *quillaja* fraction QHC was modulated (oxidized) by periodate treatment for the time periods indicated as described in Materials and Methods.

| | Modulation time (hour) |
|---|---|
| 1. | 1 |
| 2. | 2.5 |
| 3. | 4 |
| 4. | 5 |

QHC treated with periodate for 1 hour killed the U937 cancer cells (FIG. 19:1) measured by the Alamar Blue Method (see Materials and Methods). QHC oxidized for more than one hour did not kill U937 cancer cells.

Periodate treatment abolished at all time points the cancer cells to produce IL-8 (see modulation time and FIG. 19:2).

Reduction of the Aldehyde Group in Position C-23 on QA

The aldehyde group of QHC saponin fraction was reduced by borohydride treatment as described in Materials and Methods and analyzed for IL-8 production.

The reduction of the aldehyde moiety with borohydride as described in Materials and Methods totally abolished the capacity of QHC to kill U937 cancer cells in comparison to the non-modified QHC.

The borohydride reduction did not negatively affect the U937 cancer cells to produce IL-8, it even enhanced this production compared to the non-treated controls (FIG. 19:4).

That was possibly due to higher cell survival rate in comparison to the cells incubated with non-reduced QHC. I.e. the depressed active level of anticancer cell killing actively by programmed cell death[3,20] (implicating more cells are actively producing IL-8 (See example 3).

Discussion

The sugar moieties of the *quillaja* saponin are essential for the biological effects that are exerted over sugar binding proteins in the plasma membrane i.e. over lectins on the cell surface. The sugar hexose and pentose rings are opened by oxidation resulting in an aldehyde formation.

This example shows that modification of the hexose and pentose sugar structures by periodate oxidation abolish the immunological adjuvant effect recorded by the reduced IL-8 cytokine production. That was expected since the sugar modification affects most certainly the initial receptor mechanism occurring over lectins in the cell membranes including those in the outer plasma membrane. The oxidation also abolished the cancer cell killing effect at reasonable concentration of QHC in the assay confirming an essential role of the lectin-sugar interactions in the initiation of cancer killing effects. The subsequent path and signal ways might still be active even for immune development as suggested by the subsequent cytokine production and the anti cancer cell effects that is continued along the line of Berenjian et al[20].

Reduction by borohydride affected the aldehyde moiety at the position C-23 on the triterpen skeleton as confirmed by NMR. That abolished completely the cancer cell killing capacity, but surprisingly not the immune enhancing effect clearly informing that two receptor mechanisms are prevailing. One is initiated by the sugar-lectin interaction i.e. in an aqueous medium and another one is using a hydrophobic start point (in a lipid membrane) by a sterol and terpen interaction that is essential for the cancer killing effect. Most unexpected is the phenomenon that by abolishing the active cancer cell killing effect an immune enhancing mechanism is promoted. That proves first of all that the cancer cell killing is not a cytostatic effect but a stimulatory pathway initiated in the hydrophobic area in the cell membrane different from the aqueous start via lectins. We hereby prove a new way of medical anticancer therapy that is not a mode of cytostatic treatment but based on guiding cells along their natural path eventually leading to their programmed natural death (apoptosis) as described by Hu et al[3]. Thus, both a programmed adjuvant-vaccine effect needs not be dependent on unavoidable side effects but by a positive steering of immune compatible cells. That mode can also be used to steer cancer cells to ceased replication (as normal immune cells) and lead to the silent and natural programmed death i.e. apoptosis. Thus, the present invention also opens for anti-cancer treatment that can increase the patient comfort considerably. Both in cancer treatment and in enhancing immune responses this ceased cell replication[20] precedes the differentiation. With G3 in the present invention both these goals are achieved.

Conclusion

Thus, this invention reveals two receptor mechanisms and signal ways are initiated by the *quillaja* saponin. One initiated via the lectins in the plasma membrane of the cells and the other one in the cell membrane by a terpen sterol interaction. The involvement of the terpen is proven by the fact that a targeting of the aldehyde in the terpen skeleton abolished anti-cancer cell activity. There are certainly further linking to lipids e.g. phosphatidylcholine[21-23]. It has not before been possible to discriminate by cancer killing and immune stimulating effects by the G3 particle. That is of considerable importance considering the dual effect on e.g. cancer treatment that benefits from anticancer effect by cancer cell death but also from simultaneously, preceding or subsequent stimulation of immune responses with known or unknown cancer antigens. Furthermore, by promoting the innate immune system an arm of cancer treatment is recruited as is already used in anticancer therapy by e.g. the involvement of IFN γ as already used in immune therapy of cancer. The dual effect explains the well-accepted effect on normal cells by the differentiation mechanism as elucidated[3,20].

The Iscom was prepared with three components including phospholipids and all three components were considered essential for the function, structure and stability of structure as claimed by Copland et al[24]. She never had a reason to consider removal of the PC component. Until proven otherwise that opinion prevails for rational reason because all components have clear-cut biological activities that was taken into consideration by Copland and others excluding to disregard PC. The phospholipids are active having important biological functions in various areas including Phosphatidylcholine (PC) that is a major constituent of cell membranes. It is said to be transported between membranes within the cell by phosphatidylcholine transfer protein (PCTP)[21-23]. Thus, it is not self-evident for a person skilled in the art to omit PC or to realize that a cholesterol *quillaja* product should be effective in view of all the important biological effects by e.g. phosphatidylcholine. Thus there is reason why PC was not taken away.

Example 20

Example 19 shows that the sugars on *Quillaja Saponaria Molina* (QA) formulations are essential for adjuvant activity, most likely or certainly via lectins on the cell surface i.e. sugar lectin bindings. The aldehyde group is less important for enhancing immune modulation, but required for cancer cell killing.

In this example (experiment 20:1), we compare the capacity of *Quillaja* saponin (QA) to interact and extract cholesterol from the membrane phase to the aqueous phase by participation of QA-sugars in the formation of G3 particles. We have used a blocking technique as a tool to explore the direct interaction of the superficial sugar layer covering the *Quillaja* saponin (QA) molecule with the cholesterol having the apolar OH group in the aqueous phase. This interaction is very specific between two molecular groups i.e. the cholesterol OH group and a QA group (COOH—) in the sugar moiety supplying negatively charge. There are several sugars on the QA molecule with potential to participating in this activity i.e. The monosaccharaides Glucose, N-acetyl-D-Galactosamine. L-Xylose and D-Xylose are those used in the attempts to block the G3 formation by interfering with the cholesterol via OH group and the monosaccharide moieties of QA.

In experiment 20:II, we look for another interaction i.e. on a cellular level that differs fundamentally from that dealt with in experiment 20:I in the way that cells have a complex structure of envelope proteins besides various lipids and lipoproteins. In this case the many lectin proteins are the essential cellular actors (less specific or more broadly reacting) by binding to sugars by definition and the interaction of those with the cells in creating immune responses and programmed cancer cell killing. The sugar blocking effect during G3 formation is analyzed in this experiment.

Results

The QA monosaccharaides Glucose, N-acetyl-D-Galactosamine, L-Xylose and D-Xylose are used in the attempts to block cholesterol extraction and the G3 formation.

In experiment 20:I the formation of G3 particles was determined by measuring the cholesterol being extracted from the membrane phase forming G3 particles required to dissolve the cholesterol in the aqueous phase. The initial linking occurs in the lipid aqueous inter-phase. It is in the inter-phase where blocking can occur by the sugar added to the aqueous phase.

The extracted cholesterol requires for the G3 formation to be dissolved (suspended) and it is measured by ELISA (see Material and Methods) in the aqueous phase. The *Quillaja* Saponin (QA) molecule contains several sugar moieties including 1 glucose, 2 D-xylose, 1 galactose, 1 rhamnose, 1 fucose, 1 apiose etc as shown in FIG. 18:3. The sugar composition between different QA molecules differs. The sugars were applied 1 hour before adding the QA micelles allowing interaction in the presence of the sugars thereby having opportunity for blocking under optimal conditions.

Cholesterol Content in G3 Suspensions

The monosaccharaides used for binding would potentially block extraction of cholesterol from the membrane phase to aqueous phase thereby inhibiting incorporation into the G3 particle. The cholesterol included in newly formed G3 is measured by ELISA and calculated (see Material and Methods).

Table 4 shows the cholesterol concentrations in the G3 suspension i.e. in the aqueous phase as the percentage of the input (starting material) of cholesterol (0.2 mg/ml). The not extracted cholesterol stays on the wall. Only D-Xylose showed a lowered value (37.5%) i.e. inhibition, being a reduction of 12% compared to the sample incubated without D-Xylose (QA+Chol-mem 42.5%) shown in Table 4 which is a representative of three experiments. Not explained are the increased incorporation values for L-xylose and to a less increased incorporation values for the mixture L-& D-xylose.

The Influence of QA Monosaccharaides on Cancer Cell Killing.

The interaction of QA sugars with the cell surface is different from that with the simple cholesterol membrane. The cell membrane is presenting a complex surface with large number of proteins binding sugars i.e. lectins. In this experiment the sugars were used to block incorporation of cholesterol by adding the sugars into the aqueous medium with suspended *quillaja* micelles facing the cholesterol membrane and that would interfere with the formation of G3 particles. Thus, QA sugars used in this experiment are those used in experiment 20:1 and the resulting G3 particles were applied 1 hour before the QA micelles were added to the aqueous medium. The read out was the survival rate measured by survival index (SI) as described in Materials and Methods. Since a blocking effect is preventing cholesterol to interact optimally with QA micelles in the formation of the G3 a blocking effect of G3 formation makes more available free QA causing increased lyses and necrosis i.e. toxic reactions causing cell death that is read as low survival and a low SI value. Extracted cholesterol is soluble by integration and forming G3 particles resulting in higher SI. The results are shown in Table 4.

The general feature is that G3 particles produced in the presence of high concentrations of blocking QA sugars increased the cancer cell killing i.e. that effect being more prominent by increasing concentrations of sugar implying that the higher concentrations tested read lowered SI by interfering with the cholesterol integration into G3 thereby facilitating the toxic effect of "free QA". For details see Table 5.

The Effect of Sugar Blocking During G3 Formation on Cancer Cell Killing

G3 particles formulated in the presence or absence of sugars are tested on U937-1 cells in serial dilution starting from *Quillaja* saponin concentration of 100-0.032 μg/ml. Free form of QA is used as positive control. The cell metabolism activity is analyzed by Alamar Blue at 570 and 600 nm. The results are shown in Tables 5 and 6, and the general feature is that all sugars render G3 that are more killing the cancer cells implicating a disturbed assembly of G3 particles.

Discussion

Present invention relies on an artificial cholesterol membrane i.e. it doesn't contain other molecules i.e. a very clean model. Cholesterol doesn't form natural membrane in cells. In water a phospholipid or another lipid molecule is needed to form a membrane, e.g. a liposome, with larger hydrophilic moiety that is expanding into the water. We solved that part by anchoring the cholesterol molecules to a solid hydrophobic surface. That approach is innovative facilitating a monolayer of cholesterol stand alone, orienting the OH group as an interphase directed into the aqueous phase facilitating, optimizing the interaction with the hydrophilic sugar moieties of the *quillaja* micelles. We know that the *Quillaja* micelles can interact with cholesterol from cells membrane, mediated by sugar moieties. Here we test monosaccharaides of QA per se to block extraction of cholesterol by measuring the level of cholesterol in the aqueous phase i.e. solubilized by integration into G3 particles. Only xylose but not the other monosaccharaides tested was found to block increased levels of cholesterol to be incorporated into the G3 formulation. That can be explained by the fact that xylose is the only sugar tested that is bound to Glucoronic acid that can interact with the cholesterol as described above. The first contact of *Quillaja* micelles occurs with the proton in the 3-position of cholesterol forming hydrogen bonds with COOH⁻ QA sugar moieties. To note, in the natural membranes cholesterol is forming ester bonds with aldehyde groups or COOH⁻ groups of e.g. phosphatidylcholine bonds[6]. In the *Quillaja* molecules there are also both an aldehyde group in the position (23) of the triterpen skeleton and COOH⁻ groups forming potentially ester bonds strong enough to extract the cholesterol from the hydrophobic anchoring. For more information and analyses see FIG. 20:2.

In experiment 2, the interaction of the sugars in the G3 particle formation is studied on the cellular level. In contrast to the cholesterol membrane, the cell membrane is in complex with thousands proteins and a high number of sugar binding proteins defined as lectins. It is not likely that all those lectins are real receptors enhancing signals to modulating immune responses. There are needs for additional selection mechanisms for specific receptor activities.

The cancer cell killing effect of G3 particles formulated in the presence of various sugars at different concentrations was evaluated in order to verify the sugar blocking effect. The blocking effect was calculated as the percent of reduction in EC50 values in comparison to that of the G3 formulated without addition of any sugars. To note, the higher percentage reduction i.e. lower EC50 values represent increased killing capacity. All these sugars at the concentrations tested show various degrees of blocking effect seen here as both IC50 and percent of reduction in the value. The highest reduction i.e. blocking (70.3%) and the lowest blocking (4.8%) were achieved with 0.1 mM mixture of L- and D-xylose and 0.05 mM glucose respectively. This experiment indirectly confirming the role played by the sugars in initiating the interaction between *Quillaja* saponin and the cells in line with the results in Example 19, in which QA-sugars were removed via oxidation leading to the total abolition of the cell killing as well as the immune modulating effects.

Conclusion and Discussion

According to the result, G3 can be stored at 4° C. without changing its physical characteristics and without losing its cancer cell killing and immunostimulating capacities for the period of 15 months tested.

Tables

TABLE 1

Properties table of solvents:

| Solvent | Chemical formula | Boiling point | δP Polar | δH Hydrogen bonding |
|---|---|---|---|---|
| Chloroform | CHCl3 | 61° C. | 3.1 | 5.7 |
| Dimethyl sulfoxide (DMSO) | CH3—S(=O)—CH3 | 189° C. | 16.4 | 10.2 |
| Ethanol | CH3—CH2—OH | 79° C. | 8.8 | 19.4 |
| Methanol | CH3—OH | 65° C. | 12.3 | 22.3 |
| u-Butanol | CH3—CH2—CH2—CH2—OH | 118° C. | 5.7 | 15.8 |
| Isopropanol | CH3—CH(—OH)—CH3 | 82° C. | 6.1 | 16.4 |
| n-Propanol | CH3—CH2—CH2—OH | 97° C. | 6.8 | 17.4 |
| Water | H—O—H | 100° C. | 16.0 | 42.3 |

TABLE 2A

Shows the percentage and molar ratios between cholesterol and Saponin in 10 different experiment and the results shows that the average of output cholesterol was 46% of total Input. The Molar ratio of Saponin:Cholesterol is as the calculation shows 49%: 2:1.

| Date | Total Volume | Total Cholesterol (Input) | Cholesterol in prod (Output) | Out/Input precentage | Saponin mM | Saponin/ Cholesterol |
|---|---|---|---|---|---|---|
| 14 Nov | 50 ml | 0.2 mg/ml (0.5 mM) | 0.09 mg/ml (0.23 mM) | 45% | 0.5 mM | 46% |
| 14 Nov | 50 ml | 0.2 mg/ml (0.5 mM) | 0.1 mg/ml (0.26 mM) | 50% | 0.5 mM | 52% |
| 14 Nov | 50 ml | 0.2 mg/ml (0.5 mM) | 0.12 mg/ml (0.31 mM) | 60% | 0.5 mM | 62% |
| 14-nov | 1.0 ml | 0.2 mg/ml (0.5 mM) | 0.08 mg/ml (0.21 mM) | 40% | 0.5 mM | 42% |
| 14-nov | 1.0 ml | 0.2 mg/ml (0.5 mM) | 0.1 mg/ml (0.26 mM) | 50% | 0.5 mM | 52% |
| 14-nov | 1.0 ml | 0.2 mg/ml (0.5 mM) | 0.09 mg/ml (0.23 mM) | 45% | 0.5 mM | 46% |
| 14-nov | 1.0 ml | 0.2 mg/ml (0.5 mM) | 0.09 mg/ml (0.23 mM) | 45% | 0.5 mM | 46% |
| 14-nov | 1.0 ml | 0.2 mg/ml (0.5 mM) | 0.11 mg/ml (0.28 mM) | 55% | 0.5 mM | 56% |
| 5 Dec | 100 ml | 0.2 mg/ml (0.5 mM) | 0.09 mg/ml (0.23 mM) | 45% | 0.5 mM | 46% |
| 5 Dec | 100 ml | 0.2 mg/ml (0.5 mM) | 0.08 mg/ml (0.21 mM) | 40% | 0.5 mM | 42% |

TABLE 2B

Shows the percentage and molar ratios between cholesterol and Saponin in 9 different experiments the results shows that the average of output cholesterol was 49% of total Input. The Molar ratio of Saponin:Cholesterol is as the calculation shows 51%: 2:1.

| Date | Total Volume | Total Cholesterol (Input) | Cholesterol in prod (Output) | Saponin mM | Cholesterol Input/output procentage | Saponin/Cholesterol |
|---|---|---|---|---|---|---|
| 25-okt | 50 ml | 0.2 mg/ml (0.5 mM) | 0.1 mg/ml (0.26 mM) | 0.5 mM | 50% | 52% |
| 25-okt | 50 ml | 0.2 mg/ml (0.5 mM) | 0.12 mg/ml (0.31 mM) | 0.5 mM | 60% | 62% |
| 14-nov | 1.0 ml | 0.2 mg/ml (0.5 mM) | 0.08 mg/ml (0.21 mM) | 0.5 mM | 40% | 42% |
| 14-nov | 1.0 ml | 0.2 mg/ml (0.5 mM) | 0.1 mg/ml (0.26 mM) | 0.5 mM | 50% | 52% |
| 14-nov | 1.0 ml | 0.2 mg/ml (0.5 mM) | 0.09 mg/ml (0.23 mM) | 0.5 mM | 45% | 46% |
| 14-nov | 1.0 ml | 0.2 mg/ml (0.5 mM) | 0.09 mg/ml (0.23 mM) | 0.5 mM | 45% | 46% |
| 14-nov | 1.0 ml | 0.2 mg/ml (0.5 mM) | 0.11 mg/ml (0.28 mM) | 0.5 mM | 55% | 56% |
| 1 Dec | 1.0 ml | 0.2 mg/ml (0.5 mM) | 0.1 mg/ml (0.26 mM) | 0.5 mM | 50% | 52% |
| 1 Dec | 1.0 ml | 0.2 mg/ml (0.5 mM) | 0.1 mg/ml (0.26 mM) | 0.5 mM | 50% | 52% |

TABLE 3

TEM analysis of G3 particles

| Total calculated particles | Calculated particles with size 17-22 nm | Calculated particles with size 25-30 nm | Calculated particles with size 30-35 nm |
|---|---|---|---|
| 3581 | 3177 | 322 | 82 |
| 100% | 88% | 9.00% | 3% |

TABLE 4

Cholesterol extracted by Quillaja saponin (QA) from the wall-anchored cholesterol membrane. The input of cholesterol was 0.2 mg

| Sample | Cholesterol μg/μl | % of the input |
|---|---|---|
| 1  1 mg/ml QA + Chol-men | 0.085 | 42.5 |
| 2  1 mg/ml QA + Chol-mem + 5 mM Glucose | 0.087 | 43.5 |
| 3  1 mg/ml QA + Chol-mem + 5 mM Galactosamine | 0.09 | 45 |
| 4  1 mg/ml QA + Chol-mem + 10 mM D-Xylose | 0.075 | 37.5 |
| 5  1 mg/ml QA + Chol-mem + 10 mM L-Xylose | 0.123 | 61.5 |
| 6  1 mg/ml QA + Chol-mem + 10 mM D and L-Xylose | 0.107 | 53.5 |

TABLE 5

G3 particles produced in the presence of Glucose or Galactosamine were tested for killing capacity on U937 cells expressed as EC50*(μg/mL) and percent of reduction**

| Sugar | 0.05 mM | 0.5 mM | 5 mM |
|---|---|---|---|
| Glucose | 0.5458 (4.8%) | 0.3052 (46.8%) | 0.2215 (61.4%) |
| Galactosamine | 0.3668 (36.0%) | 0.3891 (32.1%) | 0.2136 (32.1%) |

EC50 of standard G3 formulation (i.e. produced without blocking sugars) = 0.5734.
*half maximal effective concentration
**compared to the standard G3 formulation

TABLE 6

G3 particles produced in the presence of L-Xylose, D-Xylose or the mixture of these two sugars were tested for killing capacity on U937 cells expressed as EC50*(μg/mL) and percent of reduction**

| Sugar | 0.1 mM | 1 mM | 10 mM |
|---|---|---|---|
| L-Xylose | 0.2513 (56.2%) | 0.3627 (36.7%) | 0.2277 (60.3%) |
| D-Xylose | 0.3296 (42.5%) | 0.3406 (40.6%) | 0.2503 (56.3%) |
| Mixture of L-& D-Xylose | 0.1702 (70.3%) | 0.1786 (68.9%) | 0.2786 (51.4%) |

EC50 of standard G3 formulation (i.e. produced without blocking sugars) = 0.5734.
*half maximal effective concentration
**compared to the standard G3 formulation

REFERENCES

1. Bror Morein, Kefei Hu, Karin Lovgren, D'Hondt E. New ISCOMs meet unsettled vaccine demands in Vaccine Adjuvants and Delivery Systems. 2007 (Ed. by Singh M. A John Wiley & Sons, Inc., Publication, Hoboken, N.J.): 191-222.
2. Lövgren-Bengtsson K, Morein B. The ISCOM Technology in Methods in Molecular Medicine. 2000; 42 (Vaccine adjuvants: Preparation Methods and Research Protocols, Edited by D.T.O O'Hagen, Humana Press, Inc., Titawa, N.J.):239-258.
3. Hu K, Berenjian S, Larsson R, et al. Nanoparticulate Quillaja saponin induces apoptosis in human leukemia cell lines with a high therapeutic index. *International journal of nanomedicine.* 2010; 5:51-62.
4. Kensil C R. Modified saponins isolated from Quillaja Saponaria. 1995.
5. Bankefors J. Methods for structural characterisation of Quillaja Saponins by Electrospray Ionisation Ion Trap Multiple-Stage Mass Spectrometry 2008.
6. Nes W D. Biosynthesis of cholesterol and other sterols. *Chemical reviews.* Oct. 12, 2011; 111(10):6423-6451.
7. Lipinski C. Poor aqueous solubility—an industry wide problem in drug discovery. *Am. Pharm.* 2002; Rev. 582-85.
8. Tycho Heimbach, David Fleisher, Kaddoumi A. Overcoming Poor Aqueous Solubility of Drugs for Oral Delivery. *Prodrugs-Biotechnology: Pharmaceutical Aspects.* 2007; V: pp 157-215
9. Lycke N. From toxin to adjuvant: the rational design of a vaccine adjuvant vector, CTA1-DD/ISCOM. *Cellular microbiology. January* 2004; 6(1):23-32.
10. Blair A H, Ghose T I. Linkage of cytotoxic agents to immunoglobulins. *Journal of immunological methods.* Apr. 29, 1983; 59(2):129-143.

11. Davis M T, Preston J F. A simple modified carbodiimide method for conjugation of small-molecular-weight compounds to immunoglobulin G with minimal protein cross-linking. *Analytical biochemistry*. Sep. 15, 1981; 116(2): 402-407.

12. Ghose T I, Blair A H, Kulkarni P N. Preparation of antibody-linked cytotoxic agents. *Methods in enzymology*. 1983; 93:280-333.

13. Eliasson D G, El Bakkouri K, Schon K, et al. CTA1-M2e-DD: a novel mucosal adjuvant targeted influenza vaccine. *Vaccine*. Feb. 26, 2008; 26(9):1243-1252.

14. Riaz M. Liposomes preparation methods. *Pakistan journal of pharmaceutical sciences*. January 1996; 9(1):65-77.

15. Esmat Abou-Arab, Abou-Arab A, Abu-Salem M F. Physico-chmical assessment of natural sweeteners steviosides produced from *Stevia rebaudiana* bertoni. *African Journal of Food Science*. 2010; Vol 4 (5) 269-281.

16. Boonkaewwan C, Toskulkao C, Vongsakul M. Anti-Inflammatory and Immunomodulatory Activities of Stevioside and Its Metabolite Steviol on THP-1 Cells. *Journal of agricultural and food chemistry*. Feb. 8, 2006; 54(3):785-789.

17. Kersten G F, Spiekstra A, Beuvery E C, Crommelin D J. On the structure of immune-stimulating saponin-lipid complexes (iscoms). *Biochimica et biophysica acta*. Feb. 25, 1991; 1062(2):165-171.

18. Rappuoli R, Gregorio E D. *Novel Immunologic Adjuvants*. 2011; Chap 5, Page 55-66.

19. Soltysik S, Wu J Y, Recchia J, et al. Structure/function studies of QS-21 adjuvant: assessment of triterpene aldehyde and glucuronic acid roles in adjuvant function. *Vaccine*. 1995; 13(15):1403-1410.

20. Berenjian S, Hu K. Abedi-Valugerdi M. Hassan M, Bashir Hassan S, Morein B. The nanoparticulate *Quillaja* saponin KGI exerts anti-proliferative effects by down-regulation of cell cycle molecules in U937 and HL-60 human leukemia cells. *Leukemia & lymphoma*. Dec. 2, 2013.

21. Hoffmann P R. Kench J A, Vondracek A. et al. Interaction between phosphatidylserine and the phosphatidylserine receptor inhibits immune responses in vivo. *Journal of immunology*. Feb. 1, 2005; 174(3):1393-1404.

22. Kanno K. Wu M K, Agate D S, et al. Interacting proteins dictate function of the minimal START domain phosphatidylcholine transfer protein/StarD2. *The Journal of biological chemistry*. Oct. 19, 2007; 282(42):30728-30736.

23. Wirtz K W. Phospholipid transfer proteins. *Annual review of biochemistry*. 1991; 60:73-99.

24. Copland M J, Rades T, Davies N M. Hydration of lipid films with an aqueous solution of Quil A: a simple method for the preparation of immune-stimulating complexes. *International journal of pharmaceutics*. Mar. 10, 2000; 196(2):135-139.

The invention claimed is:

1. A nanoparticle composed of two components and lacking phospholipid, the nanoparticle formed from a sterol membrane and a *quillaja* saponin micelle in an aqueous solution and having a particle diameter in the range of 12-35 nanometers.

2. The nanoparticle according to claim 1, wherein sterol molecules of the sterol membrane are bound by a hydrophobic bond between a hydroxyl group of the sterol molecules and terpene moieties in the *quillaja* saponin micelle and by a hydrophilic hydrogen bond between a OH in the sterol molecules and a COOH$^-$ group or an aldehyde group in the *quillaja* saponin micelle.

3. The nanoparticle according to claim 1, wherein the sterol is cholesterol.

4. The nanoparticle according to claim 1, further having one or more of the following characteristics:
a particle diameter in the range of 15-25 nanometers,
the particle is built of 6 nm hexagonal rings built up by sterol and *quillaja* molecule subunits,
the molar ratio of sterol versus *quillaja* saponin in the particle is 1:2 to 2:1, or
several particles are densely packed, well dispersed and colloidal in water.

5. The nanoparticle according to claim 4 having a particle diameter in the range of 17-20 nanometers.

6. The nanoparticle according to claim 1, wherein the nanoparticle comprises saponin selected from raw saponin, non-fractioned saponin, and fractions of saponin which contain fatty acids.

7. The nanoparticle according to claim 6, wherein the fractions of saponin which contain fatty acids are selected from saponin fractions 15-22, saponin fraction B, saponin fraction C, and mixtures thereof.

8. The nanoparticle according to claim 1, wherein the nanoparticle comprises a fraction of saponin that does not comprise fatty acids.

9. The nanoparticle according to claim 1, wherein the nanoparticle comprises deacylsaponins.

10. The nanoparticle according to claim 1, wherein the nanoparticle comprises saponin fractions 7-14, saponin fraction A, or a mixture thereof.

11. The nanoparticles according to claim 1, wherein the weight ratio between sterol and *quillaja* saponin is from 1:2 to 2:1.

12. The nanoparticle according to claim 1, further comprising at least one amphipathic molecule or a hydrophobic molecule.

13. The nanoparticle according to claim 12, wherein the amphipathic molecule or hydrophobic molecule is selected from an antigen, an adjuvant, a targeting molecule, and a pharmaceutical compound.

14. The nanoparticle according to claim 12, wherein the amphipathic molecule or the hydrophobic molecule is selected from the group consisting of diterpen (DT), VLX40, Busulfan, roscovitine, and vitamin $D_3$.

15. A composition comprising a first nanoparticles according to claim 1, the first nanoparticle comprising a first *quillaja* saponin fraction, and a second nanoparticle according to claim 1, the second nanoparticle comprising a second *quillaja* saponin fraction, wherein the first *quillaja* saponin fraction and the second *quillaja* saponin fraction are different.

16. The composition according to claim 15, wherein the first *quillaja* saponin fraction and the second *quillaja* saponin fraction are each independently selected from the group consisting of: crude Quil A, fraction A of Quil A, fraction C of Quil A, fraction B of Quil A, any fraction between fraction C and fraction B of Quil A, fraction C and one or more other fractions of Quil A; fraction C and fraction A of Quil A, fraction B and one or more other fractions of Quil A; and fraction B and fraction A of Quil A.

17. A pharmaceutical composition comprising: (i) the nanoparticle according to claim 1; and (ii) an acceptable buffer, diluent, excipient, adjuvant, carrier, or combination thereof.

18. A pharmaceutical composition according to claim 17, further comprising at least one pharmaceutically active compound selected from the group consisting of anticancer drugs, and receptors for antibodies or monoclonal antibodies selected from a Fc receptor or a DD of Protein A of *Staphylococcus Aureus*.

19. An adjuvant composition comprising: (i) the nanoparticle according to claim 1; and (ii) an acceptable buffer, diluent, excipient, carrier, or combination thereof.

20. The adjuvant composition according to claim 19 further comprising diterpen (DT).

21. A vaccine composition comprising the adjuvant composition of claim 19.

22. A vaccine composition comprising the adjuvant composition of claim 20.

23. A vaccine composition according to claim 21 further comprising a structural protein of an influenza virus strain.

24. A vaccine composition according to claim 22 further comprising a structural protein of an influenza virus strain.

25. A pharmaceutical composition according to claim 18, wherein the anticancer drug is selected from the group consisting of platinum coordination compounds, taxane compounds, camptothecin compounds, anti-tumour vinca alkaloids, anti-tumour nucleoside derivatives, nitrogen mustard or nitrosourea alkylating agents, anti-tumour anthracycline derivatives, trastzumab and anti-tumour podophyllotoxin derivatives, antimetabolites, inhibitor of mammalian target of rapamycin (mTOR), Cytarabine, Daunorubicin, Paclitaxel, Docetaxel, Cabazitaxel, Torisel, and Trabectedin.

* * * * *